United States Patent
Ichikawa et al.

(10) Patent No.: US 9,375,434 B2
(45) Date of Patent: Jun. 28, 2016

(54) ANTITUMOR EFFECT POTENTIATOR COMPOSED OF IMIDAZOOXAZINE COMPOUND

(71) Applicant: Taiho Pharmaceutical Co., Ltd., Chiyoda-ku, Tokyo (JP)

(72) Inventors: Koji Ichikawa, Tsukuba (JP); Megumu Okada, Tsukuba (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/407,745

(22) PCT Filed: Jul. 1, 2013

(86) PCT No.: PCT/JP2013/068054
§ 371 (c)(1),
(2) Date: Dec. 12, 2014

(87) PCT Pub. No.: WO2014/007217
PCT Pub. Date: Jan. 9, 2014

(65) Prior Publication Data
US 2015/0164909 A1    Jun. 18, 2015

(30) Foreign Application Priority Data

Jul. 2, 2012 (JP) .................................. 2012-148850
Sep. 28, 2012 (JP) .................................. 2012-215902

(51) Int. Cl.
*C07D 498/14* (2006.01)
*C07D 498/04* (2006.01)
*A61K 31/5365* (2006.01)
*A61K 31/5383* (2006.01)
(Continued)

(52) U.S. Cl.
CPC ........... *A61K 31/5383* (2013.01); *A61K 31/337* (2013.01); *A61K 45/06* (2013.01); *C07D 498/04* (2013.01); *C07D 498/14* (2013.01); *A61K 2039/505* (2013.01)

(58) Field of Classification Search
CPC . C07D 498/04; C07D 498/14; A61K 31/5365
USPC ......................................... 544/89; 514/230.2
See application file for complete search history.

(56) References Cited

U.S. PATENT DOCUMENTS 8,772,283 B2 *  7/2014  Nakamura et al. ......... 514/230.2
2010/0069629 A1   3/2010  Shimma et al.
(Continued)

FOREIGN PATENT DOCUMENTS

JP       2010535847 A    11/2010
RU         2448109 C2     4/2012
(Continued)

OTHER PUBLICATIONS

Hirai et al., "MK-2206, an Allosteric Akt Inhibitor, Enhances Antitumor Efficacy by Standard Chemotherapeeutic Agents or Molecular Targeted Drugs in vitro and in vivo", Molecular Cancer Therapeutics, 2010, vol. 9, No. 7, pp. 1956-1967.
LoPiccolo eta l., "Targeting the PI3K/Akt/mTOR pathway:Effective combinations and clinical considerations", Drug Resistance Updates, 2008, vol. 11, pp. 32-50.
Manning et al, "AKT/PKB Signaling: Navigating Downstream", Cell, 2007, vol. 129, pp. 1261-1274.
Markman et al., "Status of PI3K inhibition and biomarker development in cancer therapeutics", Annals of Oncology, 2010, vol. 21, No. 4, pp. 683-691.
International Search Report cited in PCT/JP2013/068054 dated Jul. 10, 2013, 6 pages.
Bertelsen et al., "Molecular analysis of the PI3K-AKT pathway in uterine cervical neoplasia: Frequent PIK3CA amplificatoin and AKT phosphorylation", Int. J. Cancer: 118, 1877-1883 (2006).
Boyault et al., "Transcriptome Classification of HCC is Related to Gene Alterations and to New Therapeutic Targets", Hepatology, 2007, 45, 42-52.
(Continued)

*Primary Examiner* — Kahsay Habte
(74) *Attorney, Agent, or Firm* — Rothwell, Figg, Ernst & Manbeck, P.C.

(57) ABSTRACT

An antitumor effect potentiator for potentiating one or more other antitumor agents, comprising, as an active ingredient, an imidazooxazine compound represented by Formula (I), or a pharmaceutically acceptable salt thereof,

[Chem. 1]

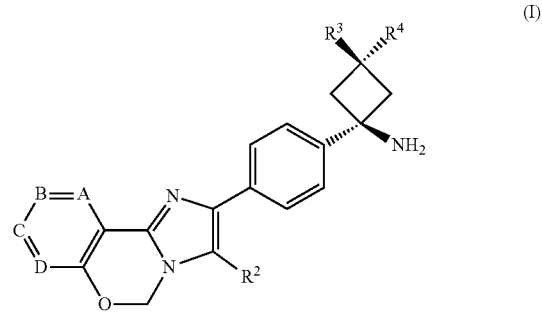

(I)

wherein A, B, C, and D represent C—$R^{1a}$, C—$R^{1b}$, C—$R^{1c}$, and C—$R^{1d}$, respectively, or one or two of A, B, C, and D represent an N atom;
at least two of $R^{1a}$, $R^{1b}$, $R^{1c}$, and $R^{1d}$ represent hydrogen, and the other(s) represent(s) halogen; cyano; $C_{1-6}$ alkyl that may have hydroxyl group(s) as substituent(s); $C_{1-6}$ alkoxy; carbonyl having, as a substituent, hydroxyl, amino, optionally substituted mono- or di-($C_{1-6}$ alkyl) amino, or mono- or di-($C_{1-6}$ alkoxy)amino; or an unsaturated heterocyclic group;
$R^2$ represents phenyl, pyridyl, or thienyl;
$R^3$ represents hydrogen, methyl, ethyl, or cyclopropyl; and
$R^4$ represents hydrogen or hydroxy.

12 Claims, 18 Drawing Sheets

(51) Int. Cl.
    *A61K 31/337*     (2006.01)
    *A61K 45/06*     (2006.01)
    *A61K 39/00*     (2006.01)

(56) References Cited

U.S. PATENT DOCUMENTS

| | | |
|---|---|---|
| 2011/0319354 A1 | 12/2011 | Layton et al. |
| 2014/0005185 A1 | 1/2014 | Nakamura et al. |

FOREIGN PATENT DOCUMENTS

| | | |
|---|---|---|
| WO | 2009021990 A1 | 2/2009 |
| WO | 2009148916 A1 | 12/2009 |
| WO | 2012137870 A1 | 10/2012 |
| WO | WO 2012137870 A1 * | 10/2012 |

OTHER PUBLICATIONS

Catasus et al., "Expression profiling of 22 genes involved in the PI3K-AKT pathway identified two subgroups of high-grade endometrial carcinomas with different molecular alterations", Modern Pathology (2010) 23, 694-702.
Chakravarti et al., "The Prognostic Significance of Phosphatidylinositol 3-Kinase Pathway Activation in Human Gliomas", Journal of Clinical Oncology, vol. 22, No. 10, May 15, 2004, 1926-1933.
Chen et al., "Involvement of PI3K/PTEN/AKT/mTOR pathway in invasion and metastasis in hepatocellular carcinoma: Association with MMP-9", Hepatology Research, 2009, 39: 177-186.
Fillmore et al., "Expression of Akt (protein kinase B) and its isoforms in malignant lymphomas", Leuk Lymphoma, Dec. 2005; 46 (12)1765-73.
Hager et al., "p-AKT overexpression in primary renal cell carcinomas and their metastases", Clin Exp Metastasis (2010) 27: 611-617.
Hasselblom et al., "High immunohistochemical expression of p-AKT predicts inferior survival in patients with diffuse arge B-cell lymphoma treated with immunochemotherapy", British Journal of Haematology, Mar. 1, 2010, 149, 560-568.
Hideshima et al., "Perifosine, an oral bioactive novel alkylphospholipid, inhibits Akt and induces in vitro and in vivo cytotoxicity in human multiple myeloma cells", Blood, May 15, 2006; 107:4053-4062.
Jendrossek et al., "Analysis of complex protein kinase B signalling pathways in human prostate cancer sample", BJU International, 2008, 102, 371-382.
Knowles et al., "Phosphatidylinositol 3-kinase (PI3K) pathway activation in bladder cancer", Cancer Metastasis Rev, (2009) 28: 305-316.
Korkolopoulou et al., "A comprehensive immunohistochemical and molecular approach to the PI3K/AKT/mTOR (phosphoinositide 3-kinase/v-akt murine thymona viral oncogene/mammalian target of rapamycin) pathway in bladder urothelial carcinoma", BJU International, 2012, 110, E1237-E1248.
LoPiccolo et al., "Targeting Akt in cancer therapy", Anti-Cancer Drugs, 2007, 18: 861-847.
Min et al., "Constitutive phosphorylation of Akt/PKB protein in acute myeloid leukemia: its significance as a prognostic variable", Leukemia (2003), 17, 995-997.
Murakami et al, "Expression of phosphorylated Akt(pAkt) in gastric carcinoma predicts prognosis and efficacy of chemotherapy", Gastric Cancer (2007) 10: 45-51.
Nakai et al., "KIT (c-kit oncogene product) pathway is constitutively activated in human testicular germ cell tumors", Biochemical and Biophysical Research Communications, 337 (2005), 289-296.
Oh et al., "Clinicopathologica correlations of mTOR and pAkt expression in non-small cell lung cancer", Virchows Arch (2012) 460: 601-609.
Pignochino et al., "Targeting EGFR/HER2 pathways enhances the antiproliferative effect of gemcitabine in biliary track and gallbladder carcinomas", BMC Cancer, 2010, 10, 631, 1-14.
Pedrero et al., "Frequent genetic and biochemical alterations of the PI 3-K/AKT/PTEN pathway in head and neck squamous cell carcinoma", Int. J. Cancer: 114, 242-248 (2005).
Roy et al., "AKT proto-oncogene overexpression is an early event during sporadic colon carcinogenesis", Carcinogeneis, vol. 23, No. 1, pp. 201-205, 2002.
Sagatys et al., "Activation of the serine/threonine protein kinase Akt during the progression of Barrett neoplasia", Human Pathology (2007) 38, 1526-1531.
Schlieman et al., "Incidence, mechanism and prognostic value of activated AKT in pancreas cancer", British Journal of Cancer, (2003) 89, 2110-2115.
Stahl et al., "Deregulated Akt3 Activity Promotes Development of Malignant Melanoma", Cancer Research, 64, Oct. 1, 2004, 7002-7010.
Sun et al., "AKT1/PKBα Kinase is Frequently Elevated in Human Cancers and its Constitutive Activation is Required for Oncogenic Transformation in NIH3T3 Cells", American Journal of Pathology, vol. 159, No. 2, Aug. 2001, 431-437.
Tanno et al., "Serine/Threonine Kinase AKT is Frequently Activated in Human Bile Duct Cancer and is associated with Increased Radioresistance", Cancer Research, 64, 3486-3490, May 15, 2004.
Uegaki et al., "PTEN—positive and phosphorylated-Akt-negative expression is a predictor of survival for patients with advanced endometrial carcinoma", Oncol Rep., Aug. 2005; 14(2); 389-92.
Valkov et al., "The prognostic impact of Akt isoforms, PI3K and PTEN related to female steroid hormone receptors in soft tissue sarcomas", Journal of Translational Medicine, 2011, 9, 200, 12 pages.
Yoshioka et al., "The activation of Akt during preoperative chemotherapy for esophageal cancer correlates with poor prognosis", Onclogy Reports, 2008, 19: 1099-1107.
Yuan et al., "Frequent activation of AKT2 and induction of apoptosis by inhibition of phosphoinositide-3-OH kinase/Akt pathway in human ovarian cancer", Oncogene (2000) 19; 2324-2330.
Zhang et al., "PI3k/Akt signaling in osteosarcoma", Clinica Chimica Acta, 444 (2015) 182-192.
Zhou et al., "Activation of the Akt/Mammalian Target of Rapamycin/4E-BP1 Pathway by ErbB2 Overexpression Predicts Tumor Progression in Breast Cancer", Clinical Cancer Research, vol. 10, Oct. 15, 2014, 6779-6788.
Office Action issued in the corresponding RU Patent Application No. 2015103151 dated Feb. 12, 2016, 12 pages, (English translation).

* cited by examiner

*overall maximal P<0.05 by closed testing procedure (Intersection-Union test)

—●— Control
—△— Carboplatin/Vehicle (50mg/kg/day/-)
—◆— Vehicle/Compound-I (-/16mg/kg/day)
—□— Carboplatin/Compound-I (50mg/kg/day/16mg/kg/day)

*overall maximal P<0.05 by closed testing procedure (Intersection-Union test)

- ●— Control
- △— Lapatinib/Vehicle (100mg/kg/day/-)
- ◆— Vehicle/Compound-I (-/16mg/kg/day)
- □— Lapatin/Compound-I (100mg/kg/day/16mg/kg/day)

*overall maximal P<0.05 by closed testing procedure (Intersection-Union test)

—●— Control
—△— Irinotecan/Vehicle (75mg/kg/day/-)
—◆— Vehicle/Compound-I (-/16mg/kg/day)
—□— Irinotecan/Compound-I (75mg/kg/day/16mg/kg/day)

\* : overall maximal P<0.01 by closed testing procedure (Intersection-Union test)

\* : overall maximal P<0.01 by closed testing procedure (Intersection-Union test)

* : overall maximal P<0.01 by closed testing procedure (Intersection-Union test)

* : overall maximal P<0.01 by closed testing procedure (Intersection-Union test)

A

B

ANTITUMOR EFFECT POTENTIATOR COMPOSED OF IMIDAZOOXAZINE COMPOUND

CROSS REFERENCE TO RELATED APPLICATIONS

This application is a 35 U.S.C. 371 National Phase Entry Application from PCT/JP2013/068054, filed Jul. 1, 2013, which claims priority to Japanese Patent Application No. 2012-148850, filed on Jul. 2, 2012, and Japanese Patent Application No. 2012-215902, filed on Sep. 28, 2012, the entire contents of which are herein incorporated by reference.

TECHNICAL FIELD

The present invention relates to an antitumor effect potentiator, and an antitumor drug comprising a combination of the potentiator and one or more other antitumor agents.

BACKGROUND ART

A wide variety of drugs has been targeted as antitumor agents. They are roughly classified into alkylating agents, platinum-based compounds, antimetabolites, topoisomerase inhibitors, microtubule inhibitors, antitumor antibiotics, molecular target drugs, and the like. Further, in recent years, the combined use of multiple drugs, instead of the administration of a single antitumor agent, has been widely prevalent.

AKT is a serine/threonine-specific kinase serving as a downstream effector of phosphatidylinositol-3 kinase (PI3 kinase), which is activated by a receptor tyrosine kinase signal. AKT is frequently activated or highly expressed in many cancers (renal cell cancer, stomach cancer, breast cancer, lung cancer, colorectal cancer, pancreatic cancer, ovarian cancer, hepatic cell cancer, multiple myeloma, lymphoma, leukemia, head and neck cancer, melanoma, and the like), and genetic amplification or activating mutation has been reported in some cancers (NPD 1). As for the function, AKT is reported to play an important role in tumorigenesis such as cell proliferation, apoptosis resistance, angiogenesis, metastasis and invasion, as well as glucose metabolism and lipid metabolism (NPD 2). AKT is also reported to be highly expressed in tumors unresponsive or resistant to existing treatments using antitumor agents. Thus, there has been an expectation regarding the effect of the combined use of an AKT inhibitor and existing antitumor agents, including molecular-targeted antitumor agents (NPD 3).

For example, there are reports of treatments using a combination of MK-2206, which is an AKT inhibitor, and docetaxel (NPD 4 and PTD 1).

CITATION LIST

Patent Document

PTD 1: Publication of US patent application No. 2011-0319354

Non-Patent Document

NPD 1: Annals of Oncology, 21, p. 683-691 (2010)
NPD 2: Cell, 129, p. 1261-1274 (2007)
NPD 3: Drug Resistance Updates, 11, p. 32-50 (2008)
NPD 4: Mol. Cancer Ther., 9, p. 1956-1967 (2010)

SUMMARY OF INVENTION

Technical Problem

However, it is completely unknown and unpredictable what combination of the antitumor agents can potentiate their antitumor effects, or, if the antitumor effects are potentiated, whether the potentiation of the toxicity of the agents also occurs as well as the potentiation of the antitumor effects.

An object of the present invention is to provide a combined use of two antitumor agents that can potentiate their antitumor effects without significantly enhancing their side effects.

Solution to Problem

In view of this problem, the present inventors focused attention on a specific kind of AKT inhibitor, and conducted research on the effect of the combined use of the compound and other antitumor agents. As a result, the inventors found that the imidazooxazine compound represented by Formula (I) below or a pharmaceutically acceptable salt thereof acts as a potent AKT inhibitor, and that the combined use of the compound and an antitumor agent(s) excellently potentiates the antitumor effect, thereby enlarging the effective area and the antitumor spectrum. With this finding, the inventors completed the present invention.

An embodiment of the present invention provides an antitumor effect potentiator for potentiating one or more other antitumor agents, comprising, as an active ingredient, an imidazooxazine compound represented by Formula (I), or a pharmaceutically acceptable salt thereof,

[Chem. 1]

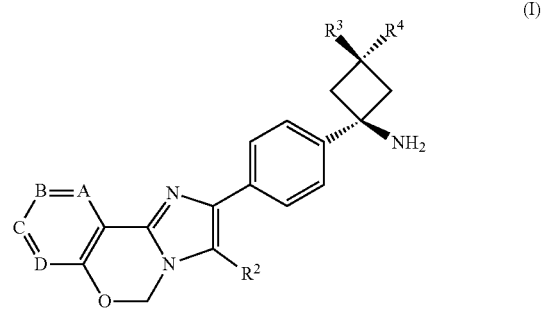

wherein A, B, C, and D represent C—$R^{1a}$, C—$R^{1b}$, C—$R^{1c}$, and C—$R^{1d}$, respectively, or one or two of A, B, C, and D represent an N atom;

at least two of $R^{1a}$, $R^{1b}$, $R^{1c}$, and $R^{1d}$ represent hydrogen, and the other(s) represent(s) halogen; cyano; $C_{1-6}$ alkyl that may have hydroxyl group(s) as substituent(s); $C_{1-6}$ alkoxy; carbonyl having, as a substituent, hydroxyl, amino, optionally substituted mono- or di-($C_{1-6}$ alkyl)amino, or mono- or di-($C_{1-6}$ alkoxy)amino; or an unsaturated heterocyclic group;

$R^2$ represents phenyl, pyridyl, or thienyl;

$R^3$ represents hydrogen, methyl, ethyl, or cyclopropyl; and $R^4$ represents hydrogen or hydroxy.

In an embodiment of the present invention, A, B, C, and D represent C—$R^{1a}$, C—$R^{1b}$, C—$R^{1c}$, and C—$R^{1d}$, respectively, or one or two of A, B, C, and D represent an N atom;

at least two of $R^{1a}$, $R^{1b}$, $R^{1c}$, and $R^{1d}$ represent hydrogen, and the other(s) individually represent(s) chlorine, fluorine, cyano, methyl, hydroxymethyl, methoxy, ethoxy, carboxyl, carbamoyl, methylaminocarbonyl, ethylaminocarbonyl, hydroxyethylaminocarbonyl, ethoxyaminocarbonyl, or pyrazolyl;

$R^2$ represents phenyl, pyridyl, or thienyl;

$R^3$ represents hydrogen, methyl, ethyl, or cyclopropyl; and $R^4$ represents hydrogen or hydroxy.

Another embodiment of the present invention provides an antitumor effect potentiator for potentiating one or more other antitumor agents, comprising an imidazooxazine compound of any one of the following (a) to (t), or a salt thereof, as an active ingredient, (a) trans-3-amino-1-cyclopropyl-3-(4-(10-fluoro-3-phenyl-5H-benzo[e]imidazo[1,2-c][1,3]oxazin-2-yl)phenyl)cyclobutanol, (b) trans-3-amino-1-cyclopropyl-3-(4-(10-fluoro-3-(pyridin-4-yl)-5H-benzo[e]imidazo[1,2-c][1,3]oxazin-2-yl)phenyl)cyclobutanol, (c) trans-3-amino-1-cyclopropyl-3-(4-(3-phenyl-5H-benzo[e]imidazo[1,2-c][1,3]oxazin-2-yl)phenyl)cyclobutanol, (d) trans-3-amino-1-cyclopropyl-3-(4-(10-methoxy-3-phenyl-5H-benzo[e]imidazo[1,2-c][1,3]oxazin-2-yl)phenyl)cyclobutanol, (e) trans-3-amino-1-cyclopropyl-3-(4-(9-methoxy-3-phenyl-5H-benzo[e]imidazo[1,2-c][1,3]oxazin-2-yl)phenyl)cyclobutanol, (f) trans-3-amino-1-cyclopropyl-3-(4-(8-methoxy-3-phenyl-5H-benzo[e]imidazo[1,2-c][1,3]oxazin-2-yl)phenyl)cyclobutanol, (g) trans-3-amino-1-cyclopropyl-3-(4-(3-phenyl-5H-imidazo[1,2-c]pyrido[2,3-e][1,3]oxazin-2-yl)phenyl)cyclobutanol, (h) trans-3-amino-1-methyl-3-(4-(3-phenyl-5H-imidazo[1,2-c]pyrido[2,3-e][1,3]oxazin-2-yl)phenyl)cyclobutanol, (i) trans-3-amino-1-ethyl-3-(4-(3-phenyl-5H-imidazo[1,2-c]pyrido[2,3-e][1,3]oxazin-2-yl)phenyl)cyclobutanol, (j) trans-3-amino-1-cyclopropyl-3-(4-(3-phenyl-5H-imidazo[1,2-c]pyrido[3,4-e][1,3]oxazin-2-yl)phenyl)cyclobutanol, (k) trans-3-amino-1-methyl-3-(4-(3-phenyl-5H-imidazo[1,2-c]pyrido[3,4-e][1,3]oxazin-2-yl)phenyl)cyclobutanol, (l) trans-3-amino-1-cyclopropyl-3-(4-(3-phenyl-5H-imidazo[1,2-c]pyrido[4,3-e][1,3]oxazin-2-yl)phenyl)cyclobutanol, (m) trans-3-amino-1-methyl-3-(4-(3-phenyl-5H-imidazo[1,2-c]pyrido[4,3-e][1,3]oxazin-2-yl)phenyl)cyclobutanol, (n) trans-3-amino-1-cyclopropyl-3-(4-(3-phenyl-5H-imidazo[1,2-c]pyrido[3,2-e][1,3]oxazin-2-yl)phenyl)cyclobutanol, (o) trans-3-amino-1-cyclopropyl-3-(4-(3-phenyl-5H-imidazo[1,2-c]pyrazino[2,3-e][1,3]oxazin-2-yl)phenyl)cyclobutanol, (p) trans-3-amino-3-(4-(9-(hydroxymethyl)-3-phenyl-5H-benzo[e]imidazo[1,2-c][1,3]oxazin-2-yl)phenyl)-1-methylcyclobutanol, (q) 2-(4-(trans-1-amino-3-hydroxy-3-methylcyclobutyl)phenyl)-3-phenyl-5H-benzo[e]imidazo[1,2-c][1,3]oxazine-9-carbonitrile, (r) trans-3-amino-1-methyl-3-(4-(3-phenyl-9-(1H-pyrazol-5-yl)-5H-benzo[e]imidazo[1,2-c][1,3]oxazin-2-yl)phenyl)cyclobutanol, (s) 2-(4-(trans-1-amino-3-hydroxy-3-methylcyclobutyl)phenyl)-N-methyl-3-phenyl-5H-benzo[e]imidazo[1,2-c][1,3]oxazine-8-carboxamide, and (t) 2-(4-(trans-1-amino-3-hydroxy-3-methylcyclobutyl)phenyl)-N-ethoxy-3-phenyl-5H-benzo[e]imidazo[1,2-c][1,3]oxazine-8-carboxamide.

Another embodiment of the present invention provides an antitumor drug comprising a combination of any one of the above imidazooxazine compounds or a pharmaceutically acceptable salt thereof, and one or more other antitumor agents.

Another embodiment of the present invention provides the use of any one of the above imidazooxazine compounds or a pharmaceutically acceptable salt thereof for potentiating one or more other antitumor agents.

Another embodiment of the present invention provides the use of any one of the above imidazooxazine compounds or a pharmaceutically acceptable salt thereof for the manufacture of an antitumor effect potentiator for potentiating one or more other antitumor agents.

Another embodiment of the present invention provides the use of any one of the above imidazooxazine compounds or a pharmaceutically acceptable salt thereof for the manufacture of an antitumor drug comprising a combination of the imidazooxazine compound or a pharmaceutically acceptable salt thereof, and one or more other antitumor agents.

In another embodiment of the present invention, the one or more other antitumor agents are paclitaxel, carboplatin, lapatinib, irinotecan, doxorubicin, everolimus, bortezomib, erlotinib, trastuzumab (herceptin), metformin, docetaxel, and a combination drug of tegafur, gimeracil, and oteracil potassium.

Another embodiment of the present invention provides a pharmaceutical composition for preventing and/or treating tumors, comprising any one of the above imidazooxazine compounds or a pharmaceutically acceptable salt thereof, and one or more other antitumor agents.

Another embodiment of the present invention provides an antitumor effect potentiating method, comprising administering to a patient any one of the above imidazooxazine compounds or a pharmaceutically acceptable salt thereof in an amount effective for treatment and/or prevention.

Another embodiment of the present invention provides a method for preventing and/or treating tumors, comprising administering to a patient a combination of any one of the above imidazooxazine compounds or a pharmaceutically acceptable salt thereof, and one or more other antitumor agents in an amount effective for treatment and/or prevention.

Another embodiment of the present invention provides a product as a combined preparation to be used concurrently, subsequently, or at an interval upon prevention and/or treatment of tumors, the product comprising a combination of any one of the above imidazooxazine compounds or a pharmaceutically acceptable salt thereof, and one or more other antitumor agents.

Advantageous Effects of Invention

Imidazooxazine Compound (I) or a pharmaceutically acceptable salt thereof potentiates various antitumor agents by being used with the antitumor agents. More specifically, when imidazooxazine compound (I) is used with other antitumor agents, 1) it does not significantly enhance the side effects of the antitumor agents, thus enabling the combined use of multiple drugs without decreasing their effective doses in amounts equivalent to the maximum effect-producing amounts of the individual drugs, 2) imidazooxazine compound (I) potentiates the antitumor agents regardless of the drug sensitivity of the antitumor agents to be combined, and 3) such an antitumor effect is observed even in low amounts in which imidazooxazine compound (I) cannot exhibit an antitumor effect alone. Accordingly, the present invention leads to the provision of a highly clinically usable therapeutic method by enlarging the area of cancer therapeutic effect, improving the therapeutic effect, etc.

DESCRIPTION OF EMBODIMENTS

Figure 1:
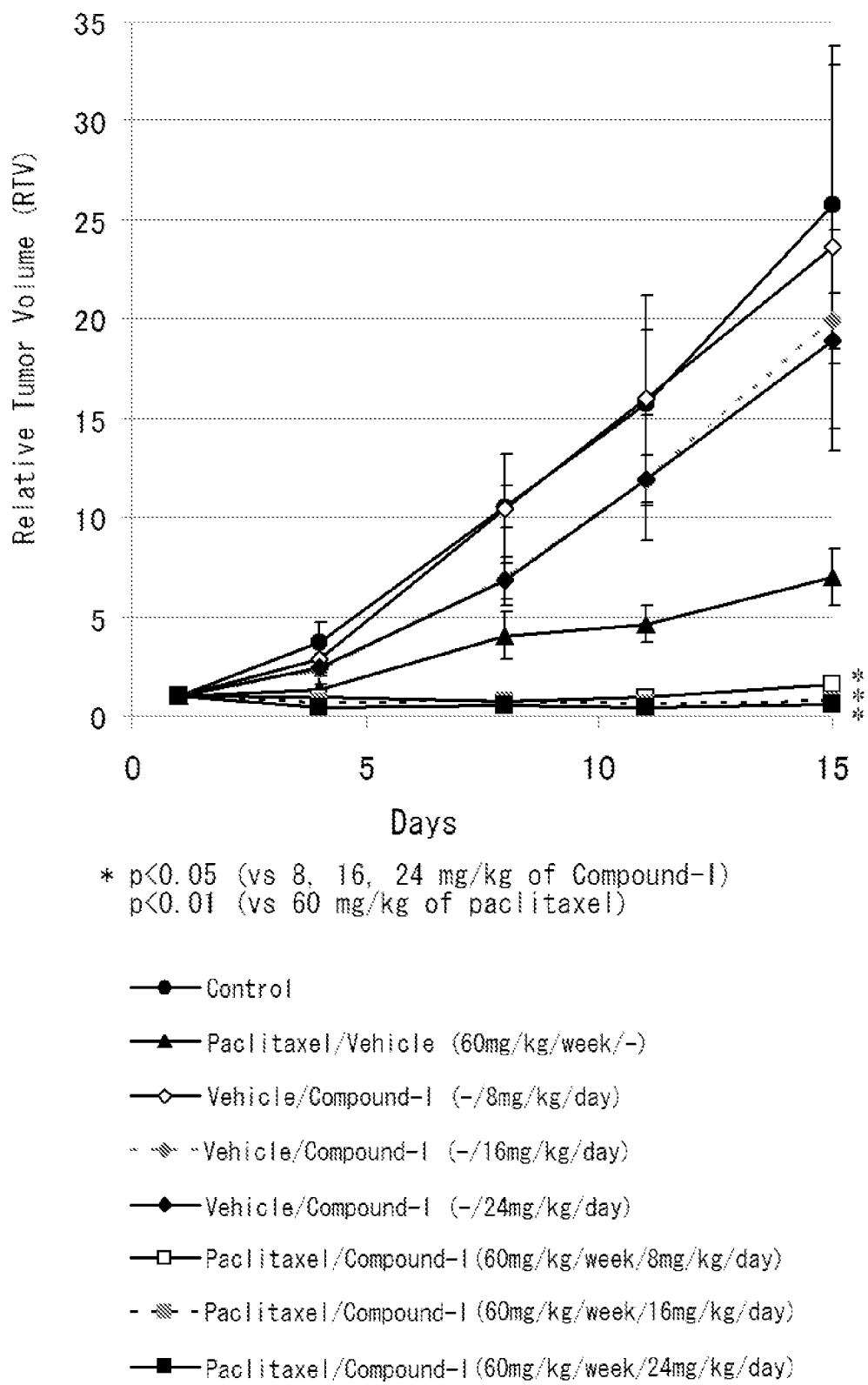
FIG. 1 Effect of combined use of Compound-I, at 8 mg/kg/day, 16 mg/kg/day, and 24 mg/kg/day, with paclitaxel in nude mice subcutaneously implanted with human ovarian cancer cell line A2780.

The term "combination" used in the present specification means use or administration of the imidazooxazine compound of the present invention or a pharmaceutically acceptable salt thereof, and one or more antitumor agents at a level sufficient to prevent and/or treat a tumor of the patient, as a single composition or two different compositions, either concurrently, successively, or with an interval. The imidazooxazine compound of the present invention or a pharmaceutically acceptable salt thereof may be administered before, concurrently, or after the administration of the other antitumor agents.

The imidazooxazine compound of the present invention or a pharmaceutically acceptable salt thereof represented by Formula (I) below potentiates antitumor effects of the antitumor agents.

[Chem. 2]

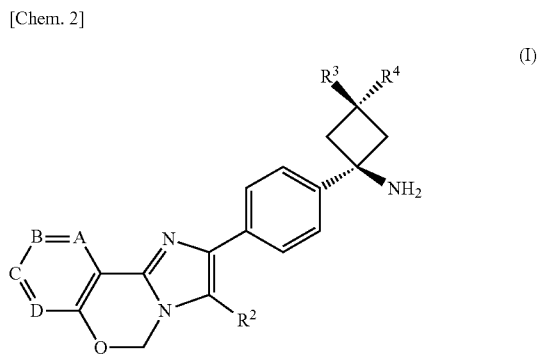

In Formula (I), A, B, C, and D represent $C—R^{1a}$, $C—R^{1b}$, $C—R^{1c}$, and $C—R^{1d}$, respectively, or one or two of A, B, C, and D represent an N atom (any of A, B, C, and D that do not represent N atom represent $C—R^{1a}$, $C—R^{1b}$, $C—R^{1c}$, or $C—R^{1d}$).

At least two of $R^{1a}$, $R^{1b}$, $R^{1c}$, and $R^{1d}$ represent hydrogen, and the other(s) represent(s) halogen, cyano, $C_{1-6}$ alkyl that may have hydroxyl group(s) as substituent(s), $C_{1-6}$ alkoxy, carbonyl having hydroxyl, amino, optionally substituted mono- or di-($C_{1-6}$ alkyl)amino, or mono- or di-($C_{1-6}$ alkoxy) amino; or an unsaturated heterocyclic group.

Examples of halogen atom represented by $R^{1a}$, $R^{1b}$, $R^{1c}$, or $R^{1d}$ include chlorine atom, bromine atom, fluorine atom, and iodine atom, preferably chlorine atom or fluorine atom.

The $C_{1-6}$ alkyl of "$C_{1-6}$ alkyl that may have hydroxyl group(s) as substituent(s)" is preferably a straight or branched $C_{1-6}$ alkyl; examples thereof include methyl, ethyl, n-propyl, isopropyl, n-butyl, isobutyl, sec-butyl, tert-butyl, pentyl, and hexyl. The $C_{1-6}$ alkyl is preferably $C_{1-3}$ alkyl, more preferably methyl. The number of hydroxyl groups (substituents) is 0 to 2, preferably 0 or 1.

The "$C_{1-6}$ alkoxy" represented by $R^{1a}$, $R^{1b}$, $R^{1c}$, or $R^{1d}$ is a straight or branched $C_{1-6}$ alkoxy such as methoxy, ethoxy, n-propoxy, isopropoxy, n-butoxy, isobutoxy, tert-butoxy or the like, preferably $C_{1-3}$ alkoxy, more preferably methoxy or ethoxy.

The mono- or di-($C_{1-6}$ alkyl)aminocarbonyl of the "optionally substituted mono- or di-($C_{1-6}$ alkyl)aminocarbonyl" of "carbonyl having, as a substituent, hydroxyl, amino, optionally substituted mono- or di-($C_{1-6}$ alkyl)amino, or mono- or di-($C_{1-6}$ alkoxy)amino" represented by $R^{1a}$, $R^{1b}$, $R^{1c}$, or $R^{1d}$ is the aforementioned aminocarbonyl having 1 or 2 $C_{1-6}$ alkyl, preferably a mono- or di-($C_{1-3}$ alkyl)aminocarbonyl, more preferably methylaminocarbonyl, dimethylaminocarbonyl, or ethylaminocarbonyl. The substituent is preferably hydroxyl. The number of substituents is preferably 1.

The mono- or di-($C_{1-6}$ alkoxy)aminocarbonyl is the aforementioned aminocarbonyl having 1 or 2 $C_{1-6}$ alkoxy, preferably a mono- or di-($C_{1-3}$ alkoxy)aminocarbonyl, more preferably ethoxyaminocarbonyl.

The "carbonyl having, as a substituent, hydroxyl, amino, optionally substituted mono- or di-($C_{1-6}$ alkyl)amino, or mono- or di-($C_{1-6}$ alkoxy)amino" represented by $R^{1a}$, $R^{1b}$, $R^{1c}$, or $R^{1d}$ is particularly preferably carboxyl, carbamoyl, methylaminocarbonyl, ethylaminocarbonyl, hydroxyethylaminocarbonyl, or ethoxyaminocarbonyl.

The unsaturated heterocyclic group represented by $R^{1a}$, $R^{1b}$, $R^{1c}$, or $R^{1d}$ is preferably a 5- to 10-membered monocyclic or bicyclic unsaturated heterocyclic group having 1 to 4 hetero atoms selected from the group consisting of N, S, and O. Examples thereof include imidazolyl, thienyl, furyl, pyrrolyl, oxazolyl, isoxazolyl, thiazolyl, isothiazolyl, pyrazolyl, triazolyl, tetrazolyl, pyridyl, pyrazyl, pyrimidinyl, pyridazinyl, indolyl, isoindolyl, indazolyl, benzofuranyl, benzimidazolyl, benzoxazolyl, benzothiazolyl, purinyl, quinolyl, isoquinolyl, quinazolinyl, and quinoxalyl. Among them, pyrazolyl is preferable.

Preferable examples of the compound represented by Formula (I) include the following compounds.
(a) trans-3-amino-1-cyclopropyl-3-(4-(10-fluoro-3-phenyl-5H-benzo[e]imidazo[1,2-c][1,3]oxazin-2-yl)phenyl)cyclobutanol,
(b) trans-3-amino-1-cyclopropyl-3-(4-(10-fluoro-3-(pyridin-4-yl)-5H-benzo[e]imidazo[1,2-c][1,3]oxazin-2-yl)phenyl)cyclobutanol,
(c) trans-3-amino-1-cyclopropyl-3-(4-(3-phenyl-5H-benzo[e]imidazo[1,2-c][1,3]oxazin-2-yl)phenyl)cyclobutanol,
(d) trans-3-amino-1-cyclopropyl-3-(4-(10-methoxy-3-phenyl-5H-benzo[e]imidazo[1,2-c][1,3]oxazin-2-yl)phenyl)cyclobutanol,
(e) trans-3-amino-1-cyclopropyl-3-(4-(9-methoxy-3-phenyl-5H-benzo[e]imidazo[1,2-c][1,3]oxazin-2-yl)phenyl)cyclobutanol,
(f) trans-3-amino-1-cyclopropyl-3-(4-(8-methoxy-3-phenyl-5H-benzo[e]imidazo[1,2-c][1,3]oxazin-2-yl)phenyl)cyclobutanol,
(g) trans-3-amino-1-cyclopropyl-3-(4-(3-phenyl-5H-imidazo[1,2-c]pyrido[2,3-e][1,3]oxazin-2-yl)phenyl)cyclobutanol,
(h) trans-3-amino-1-methyl-3-(4-(3-phenyl-5H-imidazo[1,2-c]pyrido[2,3-e][1,3]oxazin-2-yl)phenyl)cyclobutanol,
(i) trans-3-amino-1-ethyl-3-(4-(3-phenyl-5H-imidazo[1,2-c]pyrido[2,3-e][1,3]oxazin-2-yl)phenyl)cyclobutanol,
(j) trans-3-amino-1-cyclopropyl-3-(4-(3-phenyl-5H-imidazo[1,2-c]pyrido[3,4-e][1,3]oxazin-2-yl)phenyl)cyclobutanol,
(k) trans-3-amino-1-methyl-3-(4-(3-phenyl-5H-imidazo[1,2-c]pyrido[3,4-e][1,3]oxazin-2-yl)phenyl)cyclobutanol,
(l) trans-3-amino-1-cyclopropyl-3-(4-(3-phenyl-5H-imidazo[1,2-c]pyrido[4,3-e][1,3]oxazin-2-yl)phenyl)cyclobutanol,
(m) trans-3-amino-1-methyl-3-(4-(3-phenyl-5H-imidazo[1,2-c]pyrido[4,3-e][1,3]oxazin-2-yl)phenyl)cyclobutanol,
(n) trans-3-amino-1-cyclopropyl-3-(4-(3-phenyl-5H-imidazo[1,2-c]pyrido[3,2-e][1,3]oxazin-2-yl)phenyl)cyclobutanol,
(o) trans-3-amino-1-cyclopropyl-3-(4-(3-phenyl-5H-imidazo[1,2-c]pyrazino[2,3-e][1,3]oxazin-2-yl)phenyl)cyclobutanol,
(p) trans-3-amino-3-(4-(9-(hydroxymethyl)-3-phenyl-5H-benzo[e]imidazo[1,2-c][1,3]oxazin-2-yl)phenyl)-1-methylcyclobutanol,
(q) 2-(4-(trans-1-amino-3-hydroxy-3-methylcyclobutyl)phenyl)-3-phenyl-5H-benzo[e]imidazo[1,2-c][1,3]oxazine-9-carbonitrile,
(r) trans-3-amino-1-methyl-3-(4-(3-phenyl-9-(1H-pyrazol-5-yl)-5H-benzo[e]imidazo[1,2-c][1,3]oxazin-2-yl)phenyl)cyclobutanol,
(s) 2-(4-(trans-1-amino-3-hydroxy-3-methylcyclobutyl)phenyl)-N-methyl-3-phenyl-5H-benzo[e]imidazo[1,2-c][1,3]oxazine-8-carboxamide, and
(t) 2-(4-(trans-1-amino-3-hydroxy-3-methylcyclobutyl)phenyl)-N-ethoxy-3-phenyl-5H-benzo[e]imidazo[1,2-c][1,3]oxazine-8-carboxamide.

The pharmaceutically acceptable salts of imidazooxazine compound (I) refer to salts having the desirable pharmacological activity of imidazooxazine compound (I), prepared from a pharmaceutically acceptable base or acid including inorganic/organic bases and inorganic/organic acids.

Examples of pharmaceutically acceptable salts of imidazooxazine compound (I) include acid addition salts with inorganic acids, such as hydrochloric acid, hydrobromic acid, hydroiodic acid, sulfuric acid, nitric acid, phosphoric acid, and the like, or organic acids, such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, para-toluenesulfonic acid, glutamic acid, and the like; salts with inorganic bases, such as sodium, potassium, magnesium, calcium, aluminium, and the like, organic bases, such as methylamine, ethylamine, meglumine, ethanolamine, and the like, or basic amino acids, such as lysine, arginine, ornithine, and the like; and ammonium salts. Further, imidazooxazine compound (I) includes optical isomers and hydrates.

Imidazooxazine compound (I) that exhibits antitumor effect potentiation by the present invention may be produced, for example, by the following production methods or the methods described in the Examples. However, the method for producing the compound of the present invention is not limited to these examples.

Compound (I) of the present invention may be produced using, for example, the following Production Method A and Production Method B.

Production Method A

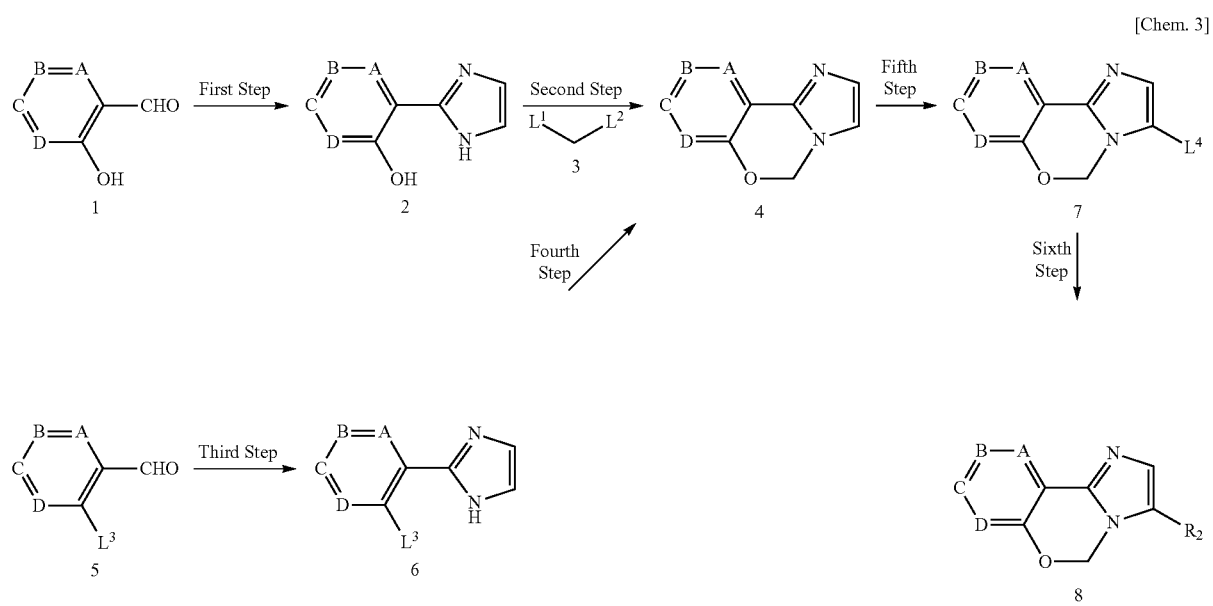

[Chem. 3]

(In the formula, L1, L2, L3, and L4 are the same or different, and each represents a leaving group; and other symbols are as defined above.)

First Step

This step is a method for obtaining compound 2 from aldehyde compound 1.

The starting compound 1 is a commercially available product, or can be produced according to a known method. The first step can be carried out by a method as described in documents (e.g., J. Med. Chem., Vol. 46, p. 5416, 2003, J. Org. Chem., Vol. 68, p. 5415, 2003), a method based thereon, or combinations of these with usual methods.

For example, when aqueous ammonia and an aqueous glyoxal solution are used in the reaction, the amount of aqueous ammonia to be used is 1 to 10 equivalents relative to the compound 1. The amount of aqueous glyoxal solution to be used is 1 to 10 equivalents relative to the compound 1.

Examples of usable solvents include methanol, ethanol, tetrahydrofuran, ethyl acetate, N,N-dimethylformamide, acetic acid, and water. The solvents can be used singly, or in combination. The reaction time is 0.1 to 100 hours, and preferably 0.5 to 24 hours. The reaction temperature is 0° C. to the boiling temperature of the solvent, and preferably 0 to 100° C.

The compound 2 thus obtained can be isolated and purified by known separation and purification means such as concentration, concentration under reduced pressure, crystallization, solvent extraction, reprecipitation and chromatography, and then subjected to the next step; or can be subjected to the next step without isolation and purification.

Second Step

This step is a process for obtaining compound 4, in which an alkylation reaction of the compound 2 with compound 3 in the presence of a base is conducted.

The compound 3, in which as L1 and L2, chlorine, bromine, iodine, etc., are mentioned, is a commercially available product, or can be produced according to a known method.

The compound 3 can be used in an amount of 1 to 100 equivalents, and preferably 1 to 10 equivalents, relative to the compound 2.

Examples of the base include inorganic bases such as sodium hydrogen carbonate, sodium carbonate, potassium carbonate, cesium carbonate, and cesium hydroxide, and organic amines such as trimethylamine, triethylamine, tripropylamine, diisopropylethylamine, N-methylmorpholine, pyridine, 4-(N,N-dimethylamino)pyridine, lutidine, and collidine. The base can be used in an amount of 1 to 100 equivalents, and preferably 2 to 10 equivalents.

Examples of usable solvents include N,N-dimethylformamide, N,N-dimethylacetamide, dimethyl sulfoxide, tetrahydrofuran, 1,4-dioxane, N-methylpyrrolidin-2-one, acetonitrile, and water. The solvents can be used singly, or in combination. The reaction time is 0.1 to 100 hours, and preferably 0.5 to 24 hours. The reaction temperature is 0° C. to the boiling temperature of the solvent, and preferably 0 to 100° C.

The compound 4 thus obtained can be isolated and purified by known separation and purification means, and then subjected to the next step; or can be subjected to the next step without isolation and purification.

Third Step

This step is a process for obtaining compound 6 from compound 5.

The compound 5, in which as L3, chlorine, bromine, iodine, etc., are mentioned, is a commercially available product, or can be produced according to a known method.

The third step can be conducted in the same manner as in the first step.

Fourth Step

This step is a process for obtaining the compound 4 in which a reaction of the compound 6 with formaldehyde is conducted in the presence of a base.

The formaldehyde can be used in an amount of 1 to 100 equivalents, and preferably 1 to 10 equivalents, relative to the compound 6. The formaldehyde can be used in the form of an aqueous solution, or in the form of paraformaldehyde.

Examples of the base include sodium hydroxide, sodium carbonate, potassium hydroxide, cesium carbonate, sodium tert-butoxide, and potassium tert-butoxide. The base can be used in an amount of 1 to 100 equivalents, and preferably 2 to 10 equivalents.

Examples of usable solvents include N,N-dimethylformamide, N,N-dimethylacetamide, dimethyl sulfoxide, tetrahydrofuran, 1,4-dioxane, N-methylpyrrolidin-2-one, acetonitrile, and water. The solvents can be used singly, or in combination. The reaction time is 0.1 to 100 hours, and preferably 0.5 to 24 hours. The reaction temperature is 0° C. to the boiling temperature of the solvent, and preferably 0 to 100° C.

The compound 4 thus obtained can be isolated and purified by known separation and purification means, and then subjected to the next step; or can be subjected to the next step without isolation and purification.

Fifth Step

This step is a process for obtaining compound 7 by conducting halogenation, for example, by allowing a halogenating agent to act on the compound 4 ($L^4$=Cl, Br or I). The halogenation can be carried out according to a commonly known method; for example, the halogenation can be carried out in a reaction solvent that does not adversely affect the reaction.

The compound 7 thus obtained can be isolated and purified by known separation and purification means, and then subjected to the next step; or can be subjected to the next step without isolation and purification.

Sixth Step

This step is a process for obtaining compound 8 by subjecting the compound 7 to a coupling reaction with an arylboronic acid, arylboronic acid ester, unsaturated heterocycle-boronic acid, or unsaturated heterocycle-boronic acid ester.

This step can be carried out according to a commonly known method (e.g., Chemical Reviews, Vol. 95, p. 2457, 1995); for example, this step can be carried out in a solvent that does not adversely affect the reaction, in the presence of a transition metal catalyst and a base.

The arylboronic acid, arylboronic acid ester, unsaturated heterocycle-boronic acid, or unsaturated heterocycle-boronic acid ester can be used in an amount of 1 to 10 equivalents, and preferably 1 to 3 equivalents, relative to the compound 7.

Examples of usable transition metal catalysts include palladium catalysts (e.g., palladium acetate, palladium chloride, tetrakis(triphenylphosphine)palladium, etc.) and nickel catalysts (e.g., nickel chloride, etc.). Where necessary, ligands (e.g., triphenylphosphine, tri-tert-butylphosphine, etc.) may be added, and metal oxides (e.g., copper oxide, silver oxide, etc.) and the like may be used as cocatalysts. Although the amount of the transition metal catalyst to be used varies depending on the type of the catalyst, it is generally about 0.0001 to about 1 mole, and preferably about 0.01 to about 0.5 moles, relative to the compound 7 (1 mole). The amount of the ligand to be used is generally about 0.0001 to about 4 moles, and preferably about 0.01 to about 2 moles, relative to the compound 7 (1 mole). The amount of the cocatalyst to be used is generally about 0.0001 to about 4 moles, and preferably about 0.01 to about 2 moles, relative to the compound 7 (1 mole).

Examples of the base include organic amines (e.g., trimethylamine, triethylamine, diisopropylethylamine, N-methylmorpholine, 1,8-diazabicyclo[5,4,0]undec-7-ene, pyridine, N,N-dimethylaniline, etc.), alkali metal salts (e.g., sodium hydrogen carbonate, potassium hydrogen carbonate, sodium carbonate, potassium carbonate, cesium carbonate, sodium phosphate, potassium phosphate, sodium hydroxide, potassium hydroxide, etc.), metal hydrides (e.g., potassium hydride, sodium hydride, etc.), alkali metal alkoxides (e.g., sodium methoxide, sodium ethoxide, sodium tert-butoxide, potassium tert-butoxide, etc.), alkali metal disilazides (e.g., lithium disilazide, sodium disilazide, potassium disilazide, etc.). Among them, alkali metal salts such as potassium carbonate, cesium carbonate, sodium phosphate, and potassium phosphate; alkali metal alkoxides such as sodium tert-butoxide and potassium tert-butoxide; organic amines such as triethylamine and diisopropylethylamine; and the like are preferable. The amount of the base to be used is generally 0.1 to 10 moles, and preferably about 1 to about 5 moles, relative to the compound 7 (1 mole).

Any solvents can be used, as long as they do not adversely affect the reaction. Examples thereof include hydrocarbons (e.g., benzene, toluene, xylene, etc.), halogenated hydrocarbons (e.g., chloroform, 1,2-dichloroethane, etc.), nitriles (e.g., acetonitrile, etc.), ethers (e.g., dimethoxyethane, tetrahydrofuran, etc.), alcohols (e.g., methanol, ethanol, etc.), aprotic polar solvents (e.g., dimethylformamide, dimethyl sulfoxide, hexamethylphosphoramide, etc.), water, and a mixture thereof. The reaction time is 0.1 to 100 hours, and preferably 0.5 to 24 hours. The reaction temperature is 0° C. to the boiling temperature of the solvent, and preferably 0 to 150° C.

The compound 8 thus obtained can be isolated and purified by known separation and purification means, and then subjected to the next step; or can be subjected to the next step without isolation and purification.

Production Method B

[Chem. 4]

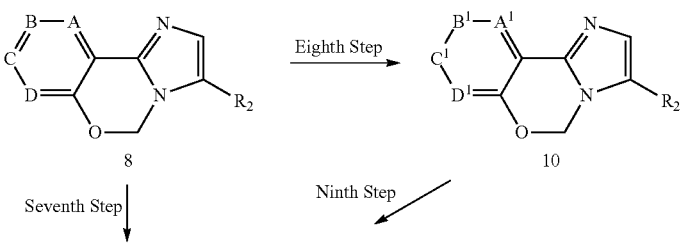

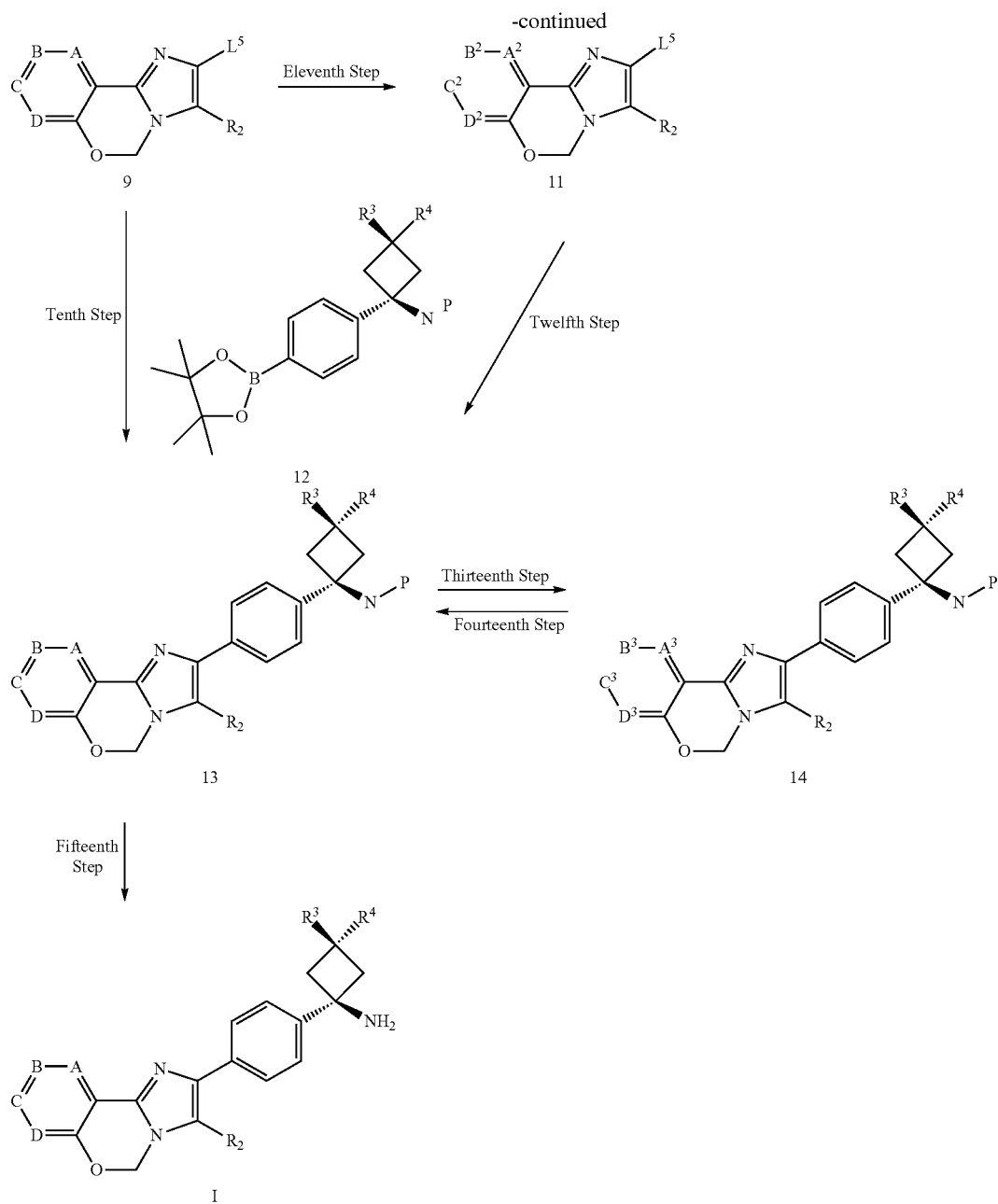

(In the formula, $L^5$ are the same or different, and each represents a leaving group; P represents a protective group; and other symbols are as defined above.)

Seventh Step

The seventh step can be conducted in the same manner as in the fifth step.

Eighth Step

This step is a process for converting any of A to D of the compound 8 into any of A1 to D1, respectively, by conducting a coupling reaction, etc., using a commonly known method.

When any of A to D of the compound 8 has a leaving group such as halogen, the coupling reaction is carried out in the presence of a transition metal catalyst to obtain compound 10.

In the case of conversion of a leaving group such as halogen to a cyano group, zinc cyanide is used. In the case of conversion to an aromatic ring or a heteroaromatic ring, commercially available boronic acid or boronic ester, or boronic acid or boronic ester that can be produced according to a known method is used.

In the case of conversion to an ester group, carbon monoxide is used.

The compound 10 thus obtained can be isolated and purified by known separation and purification means, and then subjected to the next step; or can be subjected to the next step without isolation and purification.

Ninth Step

The ninth step can be conducted in the same manner as in the fifth step.

Tenth Step

This step is a process for obtaining compound 13 by a coupling reaction of compound 9 and compound 12.

The compound 12 can be produced by a method as described in documents (e.g., WO2008-070016, WO2009-

148877, WO2009-148916, WO2010-088177, WO2010-114780, WO2010-104933), or a method based thereon.

This step can be conducted in the same manner as in the sixth step.

The compound 13 thus obtained can be isolated and purified by known separation and purification means, and then subjected to the next step; or can be subjected to the next step without isolation and purification.

Eleventh Step

This step is a process for converting any of A to D of the compound 9 into any of A2 to D2, respectively, by conducting a functional group-converting reaction, etc., using a commonly known method.

When any of A to D of the compound 9 has an ester group, compound 11 is obtained by converting the ester group into an alcohol using a commonly known reduction reaction.

The compound 11 thus obtained can be isolated and purified by known separation and purification means, and then subjected to the next step; or can be subjected to the next step without isolation and purification.

Twelfth Step

The twelfth step can be conducted in the same manner as in the tenth step.

Thirteenth Step

This step is a process for obtaining compound 14 by hydrolysis under basic conditions when any of A to D of the compound 13 has an ester group.

A base, such as sodium hydrogen carbonate, sodium carbonate, potassium carbonate, cesium carbonate, sodium hydroxide, potassium hydroxide, and lithium hydroxide can be used in an amount of 1 to 100 equivalents, and preferably 1 to 30 equivalents.

Examples of usable solvents include water, methanol, ethanol, isopropanol, tetrahydrofuran, 1,4-dioxane, N,N-dimethylformamide. The solvents can be used singly, or in combination. The reaction time is 0.1 to 100 hours, and preferably 0.5 to 24 hours. The reaction temperature is 0° C. to the boiling temperature of the solvent, and preferably 0 to 100° C.

The compound 14 thus obtained can be isolated and purified by known separation and purification means, and then subjected to the next step; or can be subjected to the next step without isolation and purification.

Fourteenth Step

This step is a process for obtaining the compound 13 by conducting an amidation reaction of the compound 14 with amine in an organic solvent.

The amidation can be conducted by a conventionally known method. Examples of such a method include a method in which a reaction of the compound 14 with the corresponding amine is carried out in the presence of a condensing agent. (See "Pepuchido Gosei No Kiso To Jikken [Foundation and Experiments of Peptide Synthesis]," Nobuo Izumiya, et al., published by Maruzen Co. in 1983.) The compound 13 thus obtained can be isolated and purified by known separation and purification means, and then subjected to the next step; or can be subjected to the next step without isolation and purification.

Fifteenth Step

This step is a process for obtaining compound (I) by deprotecting the protected amino group of the compound 13. The deprotection can be carried out by a commonly known method, for example, the method disclosed in Protective Groups in Organic Synthesis, T. W. Greene, John Wiley & Sons (1981); or a method based thereon.

Examples of the protective group include tert-butyloxycarbonyl and phthalimide. For example, when tert-butyloxycarbonyl is used as the protective group, the deprotection is preferably carried out under acidic conditions. Examples of the acid include hydrochloric acid, acetic acid, trifluoroacetic acid, sulfuric acid, and toluenesulfonic acid.

The amount of the acid to be used is preferably about 1 to about 100 equivalents relative to the compound 13.

Any solvents can be used for the reaction, as long as they do not adversely affect the reaction. For example, alcohols (e.g., methanol, etc.), hydrocarbons (e.g., benzene, toluene, xylene, etc.), halogenated hydrocarbons (e.g., methylene chloride, chloroform, 1,2-dichloroethane, etc.), nitriles (e.g., acetonitrile, etc.), ethers (e.g., dimethoxyethane, tetrahydrofuran, etc.), aprotic polar solvents (e.g., N,N-dimethylformamide, dimethyl sulfoxide, hexamethylphosphoramide, etc.), or a mixture thereof can be used. The reaction time is 0.1 to 100 hours, and preferably 0.5 to 24 hours. The reaction temperature is 0 to 100° C., and preferably 0 to 50° C.

When phthalimide is used as the protective group, hydrazine treatment can be carried out. The amount of hydrazine to be used is preferably 1 to 100 equivalents relative to the compound 13.

The reaction can be conducted with heating, using a microwave reactor or the like, to carry out synthesis. Any solvents can be used for the reaction, as long as they do not adversely affect the reaction. For example, alcohols (e.g., methanol, ethanol, etc.), hydrocarbons (e.g., benzene, toluene, xylene, etc.), halogenated hydrocarbons (e.g., methylene chloride, chloroform, 1,2-dichloroethane, etc.), nitriles (e.g., acetonitrile, etc.), ethers (e.g., dimethoxyethane, tetrahydrofuran, etc.), aprotic polar solvents (e.g., N,N-dimethylformamide, dimethyl sulfoxide, hexamethylphosphoramide, etc.), or a mixture thereof can be used. The reaction time is 0.1 to 100 hours, and preferably 0.5 to 24 hours. The reaction temperature is 0 to 200° C., and preferably 0 to 150° C.

The compound (I) thus obtained can be isolated and purified by known separation and purification means, such as concentration, concentration under reduced pressure, crystallization, solvent extraction, reprecipitation and chromatography.

Imidazooxazine compound (I) is an antitumor agent having superior AKT inhibitory activity and reduced side effect. When used with various other antitumor agents (hereinafter referred to as Antitumor Agent A), imidazooxazine compound (I) enhances the antitumor effect of Antitumor Agent A without significantly enhancing its toxicity.

Examples of Antitumor Agent A potentiated by imidazooxazine compound (I) include, but are not particularly limited to, antitumor antibiotics such as doxorubicin or epirubicin; alkylating agents such as cyclophosphamide or nimustine; platinum-based agents such as cisplatin, carboplatin, or oxaliplatin; pyrimidine-based antimetabolites such as 5-fluorouracil (5-FU), tegafur/gimeracil/oteracil potassium (i.e., a combination drug of tegafur, gimeracil, and oteracil potassium) (TS-1, general name "a combination drug of tegafur, gimeracil, and oteracil potassium" (product name: "Ti-Esu-Wan")), tegafur/uracil (a combination drug of tegafur and uracil) (UFT, general name "a combination drug of tegafur and uracil" (product name: "Yu-Efu-Ti")), capecitabine, doxifluridine, 5-fluoro-2'-deoxy uridine (FdUrd), gemcitabine, or cytarabine; purine acid-based antimetabolites such as fludarabine, cladribine, or nelarabine; folic acid antimetabolites such as pemetrexed or methotrexate; plant alkaloid antitumor agents such as paclitaxel (product names: "taxol," "abraxane," etc.), docetaxel, irinotecan, or vincristine; low-molecular-weight molecular target drugs such as gefitinib, erlotinib, lapatinib, everolimus, temsirolimus, selumetinib, trametinib, sorafenib, afatinib, regorafenib, dabrafenib, vemurafenib, bortezomib, or carfilzomib; antibody molecular target drugs such as trastuzumab (herceptin), cetuximab, bevacizumab, panitumumab, veltuzumab, or rituximab; metformin, dexamethasone, thalidomide, and lenalidomide.

Preferable examples of Antitumor Agent A potentiated by imidazooxazine compound (I) include paclitaxel, carboplatin, lapatinib, irinotecan, doxorubicin, everolimus, bortezomib, erlotinib, trastuzumab (herceptin), metformin, docetaxel, and a combination drug of tegafur, gimeracil, and oteracil potassium.

The malignant tumors treatable by imidazooxazine compound (I) together with the potentiated Antitumor Agent A include, but are not limited to, head and neck cancer, esophagus cancer, stomach cancer, colon cancer, rectum cancer, hepatocarcinoma, gallbladder cancer, cholangiocarcinoma, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, leukemia, malignant lymphoma, multiple myeloma, skin cancer, and brain tumor.

In one embodiment, the present invention relates to an antitumor effect potentiator for potentiating one or more other antitumor agents comprising, as an active ingredient, imidazooxazine compound (I) or a pharmaceutically acceptable salt thereof.

In another embodiment, the present invention relates to an antitumor drug comprising a combination of imidazooxazine compound (I) or a pharmaceutically acceptable salt thereof, and one or more other antitumor agents.

In another embodiment, the present invention relates to a pharmaceutical composition for prevention and/or treatment of tumors comprising imidazooxazine compound (I) or a pharmaceutically acceptable salt thereof, and one or more antitumor agents.

In another embodiment, the present invention relates to the use of imidazooxazine compound (I) or a pharmaceutically acceptable salt thereof for potentiating one or more other antitumor agents.

In another embodiment, the present invention relates to the use of imidazooxazine compound (I) or a pharmaceutically acceptable salt thereof for the manufacture of a potentiator for potentiating one or more other antitumor agents.

In another embodiment, the present invention relates to a method for potentiating antitumor effect, comprising administering a therapeutically and/or prophylactically effective amount of imidazooxazine compound (I) or a pharmaceutically acceptable salt thereof to a patient.

In another embodiment, the present invention relates to a method for preventing and/or treating tumors, comprising administering a therapeutically and/or prophylactically effective amount of a combination of imidazooxazine compound (I) or a pharmaceutically acceptable salt thereof, and one or more other antitumor agents.

In another embodiment, the present invention relates to a product comprising imidazooxazine compound (I) or a pharmaceutically acceptable salt thereof and one or more other antitumor agents, as a combined preparation to be used concurrently, subsequently, or at an interval upon tumor prevention and/or treatment.

By combining imidazooxazine compound (I) or a pharmaceutically acceptable salt thereof, and Antitumor Agent A, a potentiated antitumor drug is obtained. Examples of the form of such a new antitumor drug include a single preparation comprising imidazooxazine compound (I) or a pharmaceutically acceptable salt thereof and Antitumor Agent A; and a combination of separate preparations, i.e., a preparation comprising imidazooxazine compound (I) or a pharmaceutically acceptable salt thereof, and a preparation comprising Antitumor Agent A. Further, the means for administering the composition comprising imidazooxazine compound (I) and the means for administering the composition comprising Antitumor Agent A may be the same or different (for example, oral administration and injection).

When imidazooxazine compound (I) or a pharmaceutically acceptable salt thereof is contained in a pharmaceutical composition, a pharmaceutical carrier can be added, if required, thereby forming a suitable dosage form according to the prevention and treatment purposes. Examples of the dosage form include oral preparations, injections, suppositories, ointments, patches, and the like. Oral preparations are preferable. Such dosage forms can be made by methods conventionally known to persons skilled in the art.

As the pharmaceutical carrier, various conventional organic or inorganic carrier materials used as preparation materials may be blended as an excipient, binder, disintegrant, lubricant, or colorant in solid preparations, or as a solvent, solubilizing agent, suspending agent, isotonizing agent, buffer, or soothing agent in liquid preparations. Further, a pharmaceutical preparation additive, such as an antiseptic, anti-oxidant, colorant, sweetener, or stabilizer, may also be used if required.

Oral solid preparations can be prepared as follows. An excipient, optionally together with a binder, disintegrant, lubricant, colorant, sweetening/flavoring agent, or the like, is added to the compound of the present invention to produce tablets, coated tablets, granules, powders, capsules, or the like, using an ordinary method.

Examples of excipients include lactose, sucrose, D-mannitol, glucose, starch, calcium carbonate, kaolin, microcrystalline cellulose, and silicic acid anhydride.

Examples of binders include water, ethanol, 1-propanol, 2-propanol, simple syrup, liquid glucose, liquid α-starch, liquid gelatin, D-mannitol, carboxymethyl cellulose, hydroxypropyl cellulose, hydroxypropyl starch, methyl cellulose, ethyl cellulose, shellac, calcium phosphate, and polyvinylpyrrolidone.

Examples of disintegrants include dry starch, sodium alginate, agar powder, sodium hydrogen carbonate, calcium carbonate, sodium lauryl sulfate, stearic acid monoglyceride, and lactose.

Examples of lubricants include purified talc, sodium stearate, magnesium stearate, borax, and polyethylene glycol.

Examples of colorants include titanium oxide, and iron oxide.

Examples of sweetening/flavoring agents include sucrose, wild orange peel, citric acid, tartaric acid, and the like.

If necessary, an enteric coating or a coating to increase the persistence of effects can be provided by methods known for oral preparations. Examples of such coating agents include hydroxypropyl methylcellulose, ethyl cellulose, hydroxymethyl cellulose, hydroxypropyl cellulose, polyoxy ethylene glycol, and Tween 80 (registered trademark).

When oral liquid preparations are prepared, a sweetening agent, buffer, stabilizer, flavoring agent, or the like, is added to imidazooxazine compound (I) to produce an internal liquid medicine, a syrup, an elixir, or the like, using an ordinary method. In this case, the sweetening and flavoring agents as described above are usable. Examples of buffers include sodium citrate and the like, and examples of stabilizers include tragacanth, gum arabic, and gelatin.

Injections can be prepared as follows. A pH adjuster, buffer, stabilizer, isotonizing agent, topical anesthetic, or the like, is added to imidazooxazine compound (I) to produce a subcutaneous injection, an intramuscular injection, or an intravenous injection using an ordinary method. Examples of pH adjusters and buffers usable in this case include sodium citrate, sodium acetate, and sodium phosphate. Examples of stabilizers include sodium pyrosulfite, EDTA, thioglycolic acid, and thiolactic acid. Examples of topical anesthetics include procaine hydrochloride, and lidocaine hydrochloride. Examples of isotonizing agents include sodium chloride, glucose, D-mannitol, and glycerin.

Suppositories can be prepared as follows. A pharmaceutical carrier known in the art, such as polyethylene glycol, lanolin, cacao butter, or fatty acid triglyceride, is added to the compound of the present invention, optionally together with a like surfactant such as Tween 80 (registered trademark), followed by production using an ordinary method.

Ointments can be prepared as follows. An ordinary base, stabilizer, wetting agent, preservative, or the like, is added as required to the compound of the present invention, and mixed and formulated using an ordinary method. Examples of bases include liquid paraffin, white petrolatum, white beeswax, octyldodecyl alcohol, and paraffin. Examples of preservatives include methyl parahydroxybenzoate, ethyl parahydroxybenzoate, and propyl parahydroxybenzoate.

Patches can be prepared by coating a general support with the above ointment, cream, gel, paste, or the like, using an ordinary method. Examples of supports include woven or nonwoven fabrics made from cotton, staple fibers, and chemical fibers; and films and foam sheets of soft vinyl chloride, polyethylene, and polyurethane.

The drug of the present invention can be used for mammals including humans (e.g. humans, cows, horse, pigs, monkeys, dogs, cats, mice, rats, rabbits, goat, sheep, etc.), preferably humans.

The amount of imidazooxazine compound (I) to be contained in such a dosage unit form varies depending on the condition of the patient or on the dosage form. The desirable amount in one dosage unit form is typically about 0.05 to 1,000 mg in the case of an oral preparation, about 0.01 to 500 mg in the case of an injection, and about 1 to 1,000 mg in the case of a suppository. The "low amount at which imidazooxazine compound (I) does not exhibit antitumor effect alone" in one dosage unit form is about 0.05 to 20 mg in the case of an oral preparation.

The daily dose of the drug in such a dosage form depends on the symptoms, body weight, age, gender, or the like, of the patient. For example, the daily dose for an adult (body weight: 50 kg) may be generally about 0.05 to 5,000 mg, and preferably 0.1 to 1,000 mg, and is preferably administered in one dose or in two to three divided doses per day.

When the preparation comprising imidazooxazine compound (I) or a salt thereof and the preparation comprising Antitumor Agent A are separate preparations, they may be administered at the same time or in a manner such that one of the preparations is administered at an arbitrary interval before or after the administration of the other preparation. The two preparations may be administered either concurrently, subsequently, or at an interval.

The ratio of imidazooxazine compound (I) or a pharmaceutically acceptable salt thereof to Antitumor Agent A upon the administration or the mixing is not particularly limited insofar as the potentiation of their antitumor effect can be ensured; however, the amount of imidazooxazine compound (I) or a pharmaceutically acceptable salt thereof is generally about 0.001 to 100 mol, preferably about 0.005 to 50 mol, per mol of Antitumor Agent A.

For example, when Antitumor Agent A is paclitaxel, imidazooxazine compound (I) or a pharmaceutically acceptable salt thereof is about 0.05 to 50 mol, per mol of paclitaxel. When Antitumor Agent A is carboplatin, imidazooxazine compound (I) or a pharmaceutically acceptable salt thereof is about 0.005 to 5 mol, per mol of carboplatin. When Antitumor Agent A is lapatinib, imidazooxazine compound (I) or a pharmaceutically acceptable salt thereof is about 0.01 to 20 mol, per mol of lapatinib. When Antitumor Agent A is irinotecan, imidazooxazine compound (I) or a pharmaceutically acceptable salt thereof is about 0.05 to 30 mol, per mol of irinotecan. When Antitumor Agent A is doxorubicin, imidazooxazine compound (I) or a pharmaceutically acceptable salt thereof is about 0.05 to 20 mol, per mol of doxorubicin. When Antitumor Agent A is everolimus, imidazooxazine compound (I) or a pharmaceutically acceptable salt thereof is about 0.05 to 20 mol, per mol of everolimus. When Antitumor Agent A is bortezomib, imidazooxazine compound (II) or a pharmaceutically acceptable salt thereof is about 1 to 500 mol, per mol of bortezomib. When Antitumor Agent A is erlotinib, imidazooxazine compound (II) or a pharmaceutically acceptable salt thereof is about 0.01 to 10 mol, per mol of erlotinib. When Antitumor Agent A is trastuzumab (herceptin), imidazooxazine compound (I) or a pharmaceutically acceptable salt thereof is about 0.02 to 20 mol, per mol of trastuzumab (herceptin). When Antitumor Agent A is metformin, imidazooxazine compound (I) or a pharmaceutically acceptable salt thereof is about 0.00001 to 0.01 mol, per mol of metformin. When Antitumor Agent A is docetaxel, imidazooxazine compound (I) or a pharmaceutically acceptable salt thereof is about 0.001 to 0.3 mol, per mol of docetaxel. When Antitumor Agent A is a combination drug of tegafur, gimeracil, and oteracil potassium, imidazooxazine compound (I) or a pharmaceutically acceptable salt thereof is about 0.05 to 50 mol, per mol of tegafur.

EXAMPLES

The present invention is described in detail below with reference to Reference Examples, Examples, and Test Examples, which are not intended to limit the scope of the invention. Further, in the Test Examples below, the amounts of the various antitumor agents potentiated by the compound of the present invention are determined based on the Maximum Tolerated Dose (MTD) disclosed in research papers or the like, or based on the maximum dose tolerable in terms of the property of the antitumor agent.

The amount ensuring the maximum drug effect of an antitumor agent is very close to the amount expressing its toxicity. When the maximum antitumor effect of a drug is evaluated using an animal model, the evaluation is generally performed using a dose around MTD. In the Test Examples below, MTD and the maximum effect-producing amount are the same.

The reagents used in the Examples are commercially available products, unless otherwise stated. Purif-Pack SI manufactured by Shoko Co. or Biotage SNAP Cartridge KP-Sil manufactured by Biotage were used for silica gel chromatography, and Purif-Pack NH manufactured by Shoko Co. or Biotage SNAP Cartridge KP-NH manufactured by Biotage were used for basic silica gel chromatography.

For preparative thin layer chromatography, Kieselgel TM60F254, Art. 5744, manufactured by Merck & Co., or NH2 Silica Gel 60 F254 Plate-Wako, manufactured by Wako, was used. For preparative reversed-phase high-performance liquid chromatography, CombiPrep Pro C18 ($\phi$ 30 mm×50 mm), manufactured by YMC Co., was used.

1H-NMR was measured using AL400 (400 MHz), manufactured by JEOL; Mercury (400 MHz), manufactured by Varian; or Inova (400 MHz), manufactured by Varian; and using tetramethylsilane as a standard substance. In addition, the mass spectra were measured using Micromass ZQ or SQD, manufactured by Waters, by electrospray ionization (ESI) or atmospheric pressure chemical ionization (APCI). Microwave reactions were carried out using Initiator, manufactured by Biotage.

The abbreviations are defined below.

s: singlet
d: doublet
t: triplet
q: quartet
dd: double doublet
dt: double triplet
td: triple doublet
tt: triple triplet
ddd: double double doublet
ddt: double double triplet
dtd: double triple doublet
tdd: triple double doublet
m: multiplet
br: broad
DMSO-$d_6$: deuterated dimethylsulfoxide
CDCl$_3$: deuterated chloroform
THF: tetrahydrofuran
DMF: N,N-dimethylformamide
DMSO: dimethyl sulfoxide
WSC: 1-(3-dimethylaminopropyl)-3-ethylcarbodiimide hydrochloride
HOBt: 1-hydroxybenzotriazole monohydrate
Pd(PPh$_3$)4: tetrakis(triphenylphosphine)palladium Reference Example 1

10-fluoro-5H-benzo[e]imidazo[1,2-c][1,3]oxazine

A 28% aqueous ammonia solution (2.2 mL) and a 40% aqueous glyoxal solution (1.3 mL) were added to a methanol (7.0 mL) solution of 2-fluoro-6-hydroxybenzaldehyde (500 mg), and the mixture was stirred at room temperature for 5 hours. The reaction mixture was diluted with water and extracted with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the corresponding imidazophenol compound. The obtained imidazophenol compound is used for the next reaction without further purification. Potassium carbonate (1.98 g) and diiodomethane (0.44 mL) were added to a DMF (7.2 mL) solution of the obtained imidazophenol compound, and the mixture was stirred at 80° C. for 3 hours. The reaction mixture was cooled to room temperature and diluted with water, followed by extraction with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the desired product (415 mg, yield: 61%) as a colorless solid.

$^1$H-NMR (CDCl$_3$) δ: 7.32-7.22 (2H, m), 6.98-6.88 (3H, m), 5.82 (2H, s)
ESI-MS m/z 191 (MH+)

Reference Example 2

Reference Example 2(1)

2-bromo-3-(1H-imidazol-2-yl)pyridine

A 28% aqueous ammonia solution (50 mL) and a 40% aqueous glyoxal solution (50 mL) were added to a methanol (90 mL) solution of 2-bromonicotinaldehyde (10 g), and the mixture was stirred at room temperature for 14 hours. The reaction mixture was filtered, and the filtrate was concentrated under reduced pressure. The obtained residue was purified by silica gel chromatography (hexane:ethyl acetate) to give the desired product (4.62 g, yield: 38%) as a colorless solid.

$^1$H-NMR (CDCl$_3$) δ: 10.71-10.28 (1H, br m), 8.61 (1H, dd, J=7.8, 2.0 Hz), 8.35 (1H, dd, J=4.6, 2.0 Hz), 7.40 (1H, dd, J=7.8, 4.6 Hz), 7.30-7.23 (2H, br m)
ESI-MS m/z 224, 226 (MH+)

Reference Example 2(2)

5H-imidazo[1,2-c]pyrido[3,2-e][1,3]oxazine

Potassium hydroxide (66 mg) and a 37% aqueous formalin solution (0.20 mL) were added to a 2-propanol (2.0 mL) solution of the product (44.8 mg) of Reference Example 2(1), and the mixture was stirred at 80° C. for 14 hours. After being cooled to room temperature, the reaction mixture was concentrated under reduced pressure. The obtained residue was purified by silica gel chromatography (hexane:ethyl acetate) to give the desired product (16.7 mg, yield: 48%) as a colorless solid.

$^1$H-NMR (CDCl$_3$) δ: 8.29-8.24 (2H, m), 7.27 (1H, s), 7.25 (1H, d, J=1.2 Hz), 7.17 (1H, dd, J=7.3, 5.1 Hz), 6.98 (1H, d, J=1.2 Hz), 6.01 (2H, s).
ESI-MS m/z 174 (MH+)

Reference Examples 3-21

The compounds shown in Table 1 below were synthesized according to any method of Reference Example 1 or 2.

TABLE 1

| Reference Example | Starting Material | Desired Product | Production Method |
|---|---|---|---|
| 3 | F-substituted benzaldehyde with CHO and OH | F-substituted fused imidazo-oxazine | Reference Example 1 |

TABLE 1-continued

| Reference Example | Starting Material | Desired Product | Production Method |
|---|---|---|---|
| 4 | 4-fluoro-2-hydroxybenzaldehyde | 8-fluoro-benzo-fused imidazo-oxazine | Reference Example 1 |
| 5 | 3-fluoro-2-hydroxybenzaldehyde | fluoro-benzo-fused imidazo-oxazine | Reference Example 1 |
| 6 | 2-hydroxybenzaldehyde | benzo-fused imidazo-oxazine | Reference Example 1 |
| 7 | 3-methoxy-2-hydroxybenzaldehyde | OMe-substituted benzo-fused imidazo-oxazine | Reference Example 1 |
| 8 | 5-methoxy-2-hydroxybenzaldehyde | MeO-substituted benzo-fused imidazo-oxazine | Reference Example 1 |
| 9 | 4-methoxy-2-hydroxybenzaldehyde | MeO-substituted benzo-fused imidazo-oxazine | Reference Example 1 |
| 10 | 3-methoxy-2-hydroxybenzaldehyde | MeO-substituted benzo-fused imidazo-oxazine | Reference Example 1 |
| 11 | 3-chloro-2-hydroxybenzaldehyde | Cl-substituted benzo-fused imidazo-oxazine | Reference Example 1 |
| 12 | 3-ethoxy-2-hydroxybenzaldehyde | OEt-substituted benzo-fused imidazo-oxazine | Reference Example 1 |

TABLE 1-continued

| Reference Example | Starting Material | Desired Product | Production Method |
|---|---|---|---|
| 13 | 2-hydroxy-4,6-dimethoxybenzaldehyde | corresponding imidazo-oxazine | Reference Example 1 |
| 14 | 2-hydroxy-3-methylbenzaldehyde | corresponding imidazo-oxazine | Reference Example 1 |
| 15 | 5-bromo-2-hydroxybenzaldehyde | corresponding imidazo-oxazine | Reference Example 1 |
| 16 | 4-bromo-2-hydroxybenzaldehyde | corresponding imidazo-oxazine | Reference Example 1 |
| 17 | 3-hydroxypicolinaldehyde | corresponding imidazo-oxazine | Reference Example 1 |
| 18 | 4-hydroxynicotinaldehyde | corresponding imidazo-oxazine | Reference Example 1 |
| 19 | 3-hydroxyisonicotinaldehyde | corresponding imidazo-oxazine | Reference Example 1 |
| 20 | 3-methoxypyrazine-2-carbaldehyde | corresponding imidazo-oxazine | Reference Example 2 |
| 21 | methyl 6-bromo-3-hydroxypicolinate | corresponding imidazo-oxazine | Reference Example 1 |

The compounds of Reference Examples 20 and 21 in Table 1 were synthesized by the following methods in accordance with the method of Reference Example 1 or the method of Reference Example 2, using commercially available starting materials shown in the table or starting materials that can be synthesized by a known method.

Reference Example 20

Reference Example 20(1)

2-(1H-imidazol-2-yl)-3-methoxypyrazine

To a methanol (7.5 mL) solution of 3-methoxypyrazine-2-carbaldehyde (480 mg), a 40% aqueous glyoxal solution (0.80 mL) was added, and 28% aqueous ammonia (1.94 mL) was slowly added dropwise thereto at 8° C. The reaction mixture was stirred for 10 minutes, and then stirred at room temperature for 1 hour. The residue obtained by concentrating the reaction mixture under reduced pressure was purified by basic silica gel chromatography (chloroform:methanol) to give the desired product (410 mg, yield: 66%) as a light-brownish-red amorphous.
$^1$H-NMR (CDCl$_3$) δ: 10.52 (1H, brs), 8.25 (1H, d, J=2.4 Hz), 8.10 (1H, d, J=2.4 Hz), 7.38 (1H, brs), 7.21 (1H, brs), 4.20 (3H, s).
ESI-MS m/z 177 (MH+)

Reference Example 20(2)

5H-imidazo[1,2-c]pyrazino[2,3-e][1,3]oxazine

A 5 M hydrochloric acid (15 mL) aqueous solution of the product (460 mg) of Reference Example 20(1) was stirred at 120° C. for 30 minutes using a microwave reactor. The reaction mixture was cooled, azeotroped with ethanol, and concentrated under reduced pressure. Potassium carbonate (1.79 g) and diiodomethane (0.42 mL) were added to a DMF (50 mL) solution of the obtained residue, and the mixture was stirred at 80° C. for 2 hours. The reaction mixture was cooled to room temperature, diluted with water and chloroform, and extracted with chloroform. The combined organic layer was washed with water and saturated sodium chloride, dried over anhydrous sodium sulfate, and concentrated under reduced pressure. The obtained residue was purified by preparative thin-layer silica gel chromatography (chloroform:methanol) to give the desired product (36 mg, yield: 8%) as a colorless solid.
$^1$H-NMR (CDCl$_3$) δ: 8.43 (1H, d, J=2.8 Hz), 8.19 (1H, d, J=2.8 Hz), 7.41 (1H, d, J=1.2 Hz), 7.06 (1H, d, J=1.2 Hz), 6.11 (2H, s).
ESI-MS m/z 175 (MH+)

Reference Example 21

Reference Example 21(1)

methyl 6-bromo-3-(methoxymethoxy)picolinate

Diisopropylethylamine (1.46 mL) was added to a chloroform (20 mL) solution of methyl 6-bromo-3-hydroxypyridine-2-carboxylate (970 mg) and placed in a nitrogen atmosphere. Next, the reaction mixture was cooled to 0° C., and chloromethoxymethane (0.38 mL) was added thereto. The reaction mixture was stirred at 0° C. for 5 minutes, and then stirred at room temperature for 1 hour. The reaction mixture was cooled to 0° C., diluted with water, and extracted with chloroform. The combined organic layer was washed with saturated sodium chloride, dried over anhydrous sodium sulfate, and concentrated under reduced pressure. The obtained residue was purified by silica gel chromatography (hexane:ethyl acetate) to give the desired product (1.22 g, yield: 100%) as a colorless oil.
$^1$H-NMR (CDCl$_3$) δ: 7.54 (1H, d, J=8.8 Hz), 7.51 (1H, d, J=8.8 Hz), 5.26 (2H, s), 3.96 (3H, s), 3.51 (3H, s).
ESI-MS m/z 276, 278 (MH+)

Reference Example 21(2)

6-bromo-3-(methoxymethoxy)picolinaldehyde

A THF (20 mL) solution of the product (1.22 g) of Reference Example 21(1) was placed in a nitrogen atmosphere. The reaction mixture was then cooled to −78° C., and a toluene solution (5.08 mL) of 0.99 M diisobutylaluminum hydride was added thereto. The reaction mixture was stirred at −78° C. for 1 hour. Furthermore, a toluene solution (0.51 mL) of 0.99 M diisobutylaluminum hydride was added thereto, and the mixture was stirred at −78° C. for 1 hour. A saturated Rochelle salt aqueous solution was added to the reaction mixture, and then the mixture was warmed to room temperature. The reaction mixture was extracted with ethyl acetate. The combined organic layer was washed with saturated sodium chloride, dried over anhydrous sodium sulfate, and concentrated under reduced pressure to give the desired product (1.03 g, yield: 100%) as a colorless oil.
$^1$H-NMR (CDCl$_3$) δ: 10.20 (1H, s), 7.61 (1H, d, J=8.8 Hz), 7.58 (1H, d, J=8.8 Hz), 5.33 (2H, s), 3.52 (3H, s).
ESI-MS m/z 246, 248 (MH+)

Reference Example 21(3)

6-bromo-2-(1H-imidazol-2-yl)-3-(methoxymethoxy)pyridine

To a methanol (16 mL) solution of the product (1.03 g) of Reference Example 21(2), a 40% aqueous glyoxal solution (0.96 mL) was added, and 28% aqueous ammonia (2.32 mL) was slowly added dropwise thereto under ice-cooling. After stirring at room temperature for 4 hours, the reaction mixture was concentrated under reduced pressure. The obtained residue was purified by basic silica gel chromatography (chloroform:methanol) to give the desired product (0.91 g, yield: 77%) as a light-yellowish-brown solid.
$^1$H-NMR (CDCl$_3$) δ: 10.46 (1H, brs), 7.53 (1H, d, J=8.8 Hz), 7.35 (1H, d, J=8.8 Hz), 7.33 (1H, brs), 7.17 (1H, brs), 5.39 (2H, s), 3.54 (3H, s).
ESI-MS m/z 284, 286 (MH+)

Reference Example 21(4)

9-bromo-5H-imidazo[1,2-c]pyrido[2,3-e][1,3]oxazine

Trifluoroacetic acid (6.0 mL) was added dropwise under ice-cooling to a chloroform (12 mL) solution of the product (0.91 g) of Reference Example 21(3). After stirring at room temperature for 14 hours, the reaction mixture was azeotroped with toluene-chloroform, and concentrated under reduced pressure. DMF (20 mL), potassium carbonate (2.22 g), and diiodomethane (0.52 mL) were added to the obtained residue, and the mixture was stirred at 80° C. for one and a half hours. Furthermore, potassium carbonate (0.22 g) and diiodomethane (0.052 mL) were added thereto, and the mixture was stirred at 80° C. for 30 minutes. The reaction mixture was cooled to room temperature, diluted with water and chloroform, and filtered with Celite. The obtained filtrate was extracted with a 10% methanol-chloroform solution. The combined organic layer was washed with saturated sodium chloride, dried over anhydrous sodium sulfate, azeotroped with toluene, and concentrated under reduced pressure. The obtained residue was purified by basic silica gel chromatography (chloroform:methanol) to give the desired product (0.67 g, yield: 82%) as a light-brown solid.

$^1$H-NMR (CDCl$_3$) δ: 7.38 (1H, d, J=8.8 Hz), 7.34 (1H, d, J=1.2 Hz), 7.24 (1H, d, J=8.8 Hz), 6.99 (1H, d, J=1.2 Hz), 5.89 (2H, s).

ESI-MS m/z 252, 254 (MH+)

Reference Example 22

Reference Example 22(1)

3-bromo-10-fluoro-5H-benzo[e]imidazo[1,2-c][1,3]oxazine

A chloroform (7.0 mL) solution of the product (349 mg) obtained in Reference Example 1 was cooled to 0° C. N-bromosuccinimide (343 mg) was added thereto, and the mixture was stirred at 0° C. for 1 hour. The reaction mixture was purified by silica gel chromatography (hexane:ethyl acetate) to give the desired product (360 mg, yield: 73%) as a colorless solid.

$^1$H-NMR (CDCl$_3$) δ: 7.32-7.26 (1H, m), 7.25 (1H, s), 6.99-6.91 (2H, m), 5.78 (2H, s).

ESI-MS m/z 269, 271 (MH+).

Reference Example 22(2)

2-bromo-10-fluoro-3-phenyl-5H-benzo[e]imidazo[1,2-c][1,3]oxazine

Phenylboronic acid (349 mg) and cesium carbonate (1.55 g) were added to a solution of the product (513 mg) of Reference Example 22(1) in 1,4-dioxane (10 mL) and water (1.3 mL), and the mixture was placed in a nitrogen atmosphere. Pd(PPh3)4 (221 mg) was added thereto, and the mixture was stirred at 100° C. for 2 hours. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the corresponding coupling product. The obtained coupling product was used for the next reaction without further purification. A chloroform (5.0 mL) solution of the obtained coupling product was cooled to 0° C. N-bromosuccinimide (380 mg) was added thereto, and the mixture was stirred at room temperature for 1 hour. The reaction mixture was purified by silica gel chromatography (hexane:ethyl acetate) to give the desired product (602 mg, yield: 91%) as a colorless solid.

$^1$H-NMR (CDCl$_3$) δ: 7.55-7.42 (5H, m), 7.32-7.27 (1H, m), 6.99-6.94 (1H, m), 6.92-6.89 (1H, m), 5.73 (2H, s).

ESI-MS m/z 345, 347 (MH+).

Reference Example 23

Reference Example 23(1)

3,9-dibromo-5H-benzo[e]imidazo[1,2-c][1,3]oxazine

In the same manner as in Reference Example 22(1), the desired product (389 mg, yield: 98%) was obtained as a colorless solid by reacting the product (300 mg) of Reference Example 15.

$^1$H-NMR (CDCl$_3$) δ: 8.03 (1H, d, J=2.4 Hz), 7.41 (1H, dd, J=8.8, 2.4 Hz), 7.16 (1H, s), 6.96 (1H, d, J=8.8 Hz), 5.76 (1H, s)

ESI-MS m/z 331 (MH+)

Reference Example 23(2)

9-bromo-3-phenyl-5H-benzo[e]imidazo[1,2-c][1,3]oxazine

Phenylboronic acid (3.35 g) and cesium carbonate (23.3 g) were added to a solution of the product (9.44 g) of Reference Example 23(1) in 1,4-dioxane (250 mL) and water (40 mL), and the mixture was placed in a nitrogen atmosphere. Pd(PPh3)4 (3.30 g) was then added thereto, and the mixture was stirred at room temperature for 14 hours and stirred at 50° C. for 5 hours. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the desired product (7.32 g, yield: 78%) as a colorless solid.

$^1$H-NMR (CDCl$_3$) δ: 8.11 (1H, d, J=2.4 Hz), 7.50-7.32 (6H, m), 7.28 (1H, s), 6.95 (1H, d, J=8.5 Hz), 5.84 (2H, s)

ESI-MS m/z 327, 329 (MH+)

Reference Example 23(3)

methyl 3-phenyl-5H-benzo[e]imidazo[1,2-c][1,3]oxazine-9-carboxylate

Diisopropylethylamine (8.0 mL) and [1,1'-bis(diphenylphosphino)ferrocene]dichloropalladium(II) dichloromethane complex (1.38 g) were added to a solution of the product (5.0 g) of Reference Example 23(2) in DMF (30 mL) and methanol (30 mL), and the mixture was placed in a carbon monoxide atmosphere and then stirred at 70° C. for 28 hours. The reaction mixture was cooled to room temperature, diluted with a saturated aqueous sodium hydrogen carbonate solution, and extracted with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the desired product (2.12 g, 45%) as a colorless solid.

$^1$H-NMR (CDCl$_3$) δ: 8.70 (1H, d, J=2.0 Hz), 8.02 (1H, dd, J=8.5, 2.0 Hz), 7.52-7.46 (2H, m), 7.44-7.36 (3H, m), 7.31 (1H, s), 7.13 (1H, d, J=8.5 Hz), 5.93 (2H, s), 3.93 (3H, s).

ESI-MS m/z 307 (MH+).

Reference Example 23(4)

methyl 2-bromo-3-phenyl-5H-benzo[e]imidazo[1,2-c][1,3]oxazine-9-carboxylate

N-bromosuccinimide (754 mg) was added to a chloroform (16 mL) solution of the product (1.0 g) of Reference Example 23(3), and the mixture was stirred at room temperature for 1 hour. The reaction mixture was filtered, and the residue was washed with chloroform to give the desired product (800 mg, yield: 64%) as a colorless solid.

$^1$H-NMR (CDCl$_3$) δ: 8.71 (1H, d, J=2.0 Hz), 8.04 (1H, dd, J=8.5, 2.0 Hz), 7.56-7.42 (5H, m), 7.12 (1H, d, J=8.5 Hz), 5.80 (2H, s), 3.93 (3H, s).

ESI-MS m/z 385, 387 (MH+)

Reference Example 24

(2-bromo-3-phenyl-5H-benzo[e]imidazo[1,2-c][1,3]oxazin-9-yl)methanol

A methylene chloride (14 mL) solution of the product (550 mg) of Reference Example 23(4) was cooled to 0° C. A toluene solution (4.3 mL) of 0.99 M diisobutylaluminum hydride was added thereto, and the mixture was stirred at 0° C. for 1 hour. A saturated Rochelle salt aqueous solution was added to the reaction mixture, after which the mixture was stirred at room temperature for 2 hours. The reaction mixture was extracted with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the desired product (397 mg, yield: 78%) as a colorless solid.

$^1$H-NMR (CDCl$_3$) δ: 7.98 (1H, d, J=2.0 Hz), 7.55-7.42 (5H, m), 7.37 (1H, dd, J=8.3, 2.2 Hz), 7.07 (1H, d, J=8.3 Hz), 5.73 (2H, s), 4.74-4.70 (2H, br m)

ESI-MS m/z 357, 359 (MH+)

Reference Example 25

Synthesis of 2-bromo-3-phenyl-5H-benzo[e]imidazo[1,2-c][1,3]oxazine-9-carbonitrile In a nitrogen atmosphere, zinc cyanide (360 mg) and di-tert-butyl palladium (78.2 mg) were added to a solution of the product (500 mg) of Reference Example 23(2) in 1,4-dioxane (3.0 mL) and DMF (3.0 mL), and the mixture was stirred at 100° C. for 3 hours. The reaction mixture was cooled to room temperature, diluted with ethyl acetate, and filtered. The filtrate was sequentially washed with a saturated aqueous sodium hydrogen carbonate solution and saturated sodium chloride, dried over anhydrous sodium sulfate, and concentrated under reduced pressure. The obtained residue was purified by silica gel chromatography (hexane:ethyl acetate) to give the corresponding cyano compound. The cyano compound is used for the next reaction without further purification. N-bromosuccinimide (352 mg) was added to a chloroform (8.0 mL) solution of the obtained cyano compound, and the mixture was stirred at room temperature for 1 hour. The reaction mixture was filtered, and the residue was washed with chloroform to give the desired product (207 mg, yield: 36%) as a colorless solid.

$^1$H-NMR (CDCl$_3$) δ: 8.26 (1H, d, J=2.0 Hz), 7.58 (1H, dd, J=8.5, 2.0 Hz), 7.53-7.40 (5H, m), 7.14 (1H, d, J=8.5 Hz), 5.80 (2H, s).

ESI-MS m/z 352, 354 (MH+).

Reference Example 26

2-bromo-3-phenyl-9-(1-((2-(trimethylsilyl)ethoxy)methyl)-1H-pyrazol-5-yl)-5H-benzo[e]imidazo[1,2-c][1,3]oxazine 5-(4,4,5,5-tetramethyl-1,3,2-dioxaborolan-2-yl)-1-((2-(trimethylsilyl)ethoxy)methyl)-1H-pyrazole (198 mg) and cesium carbonate (250 mg) were added to a solution of the product (100 mg) of Reference Example 23(2) in 1,4-dioxane (3.0 mL) and water (0.5 mL), and the mixture was placed in a nitrogen atmosphere. Pd(PPh3)4 (35.4 mg) was then added thereto, and the mixture was stirred at 100° C. for 1 hour. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the corresponding coupling product. The obtained coupling product was used for the next reaction without further purification. N-bromosuccinimide (65.4 mg) was added to a chloroform (3.0 mL) solution of the obtained coupling product, and the mixture was stirred at room temperature for 1 hour. The reaction mixture was purified by silica gel chromatography (hexane:ethyl acetate) to give the desired product (150 mg, yield: 93%) as a colorless solid.

$^1$H-NMR (CDCl$_3$) δ: 8.16 (1H, d, J=2.0 Hz), 7.70 (1H, dd, J=8.3, 2.2 Hz), 7.57 (1H, d, J=1.7 Hz), 7.54-7.42 (5H, m), 7.15 (1H, d, J=8.3 Hz), 6.45 (1H, d, J=1.7 Hz), 5.77 (2H, s), 5.45 (2H, s), 3.77-3.71 (2H, m), 0.99-0.94 (2H, m), 0.00 (9H, s).

ESI-MS m/z 523, 525 (MH+).

Reference Example 27

2-bromo-3-phenyl-9-(1-((2-(trimethylsilyl)ethoxy)methyl)-1H-pyrazol-4-yl)-5H-benzo[e]imidazo[1,2-c][1,3]oxazine 4-(4,4,5,5-tetramethyl-1,3,2-dioxaborolan-2-yl)-1-((2-(trimethylsilyl)ethoxy)methyl)-1H-pyrazole (148 mg) and cesium carbonate (250 mg) were added to a solution of the product (100 mg) of Reference Example 23(2) in 1,4-dioxane (3.0 mL) and water (0.5 mL), and the mixture was placed in a nitrogen atmosphere. Pd(PPh3)4 (35.4 mg) was then added thereto, and the mixture was stirred at 100° C. for 1.5 hours. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the corresponding coupling product. The obtained coupling product was used for the next reaction without further purification. N-bromosuccinimide (60.0 mg) was added to a chloroform (3.0 mL) solution of the obtained coupling product, and the mixture was stirred at room temperature for 1 hour. The reaction mixture was purified by silica gel chromatography (hexane:ethyl acetate) to give the desired product (120 mg, yield: 75%) as a colorless solid.

$^1$H-NMR (CDCl$_3$) δ: 8.12 (1H, d, J=2.2 Hz), 7.86-7.85 (2H, m), 7.55-7.43 (6H, m), 7.09 (1H, d, J=8.5 Hz), 5.75 (2H, s), 5.46 (2H, s), 3.64-3.58 (2H, m), 0.97-0.92 (2H, m), 0.00 (9H, s).

ESI-MS m/z 525, 527 (MH+).

Reference Example 28

9-methyl-5H-imidazo[1,2-c]pyrido[2,3-e][1,3]oxazine

Methylboronic acid (17.8 mg) and cesium carbonate (162 mg) were added to a solution of the product (50 mg) of Reference Example 21(4) in 1,4-dioxane (2.0 mL) and water (0.32 mL), and the mixture was placed in a nitrogen atmosphere. Pd(PPh3)4 (22.9 mg) was then added thereto, and the mixture was stirred at 80° C. for 4 hours. Methylboronic acid (17.8 mg) was added to the reaction mixture, and the mixture was stirred at 110° C. for 2 hours. Further, methylboronic acid (17.8 mg) was added thereto, the mixture was stirred at 110° C. for 2 hours. The reaction mixture was cooled to room temperature, diluted with water, and extracted with chloroform. The combined organic layer was washed with saturated sodium chloride, dried over anhydrous sodium sulfate, and concentrated under reduced pressure. The obtained residue was purified by silica gel chromatography (hexane:ethyl acetate) to give the desired product (15.2 mg, yield: 41%) as a colorless oil.

$^1$H-NMR (CDCl$_3$) δ: 7.30 (1H, d, J=1.2 Hz), 7.26 (1H, d, J=8.4 Hz), 7.08 (1H, d, J=8.4 Hz), 6.97 (1H, d, J=1.2 Hz), 5.84 (2H, s), 2.60 (3H, s).

ESI-MS m/z 188 (MH+)

Reference Example 29

9-methoxy-5H-imidazo[1,2-c]pyrido[2,3-e][1,3]oxazine

A methanol solution (0.36 mL) of 25 wt % sodium methoxide was added to a methanol (2.0 mL) solution of the product (80 mg) of Reference Example 21(4), and the mixture was stirred at 110° C. for 22 hours. The reaction mixture was cooled to room temperature, diluted with water and chloroform, and extracted with chloroform. The combined organic layer was washed with saturated sodium chloride, dried over anhydrous sodium sulfate, and concentrated under reduced pressure. The obtained residue was purified by preparative thin layer basic silica gel chromatography (chloroform:methanol) to give the desired product (58.4 mg, yield: 91%) as a colorless solid.

$^1$H-NMR (CDCl$_3$) δ: 7.32 (1H, d, J=8.8 Hz), 7.31-7.30 (1H, m), 6.96 (1H, d, J=0.8 Hz), 6.71 (1H, d, J=8.8 Hz), 5.81 (2H, s), 4.05 (3H, s).

ESI-MS m/z 204 (MH+)

Reference Examples 30 to 55

The compounds shown in Table 2 below were synthesized according to any method of Reference Examples 21 to 25.

TABLE 2

| Reference Example | Starting Material | Boric Acid or Boric Acid Ester | Desired Product | Production Method |
|---|---|---|---|---|
| 30 | Reference Example 1 | (3-thienyl boronic acid) | (fluoro-bromo-thienyl imidazo-benzoxazine) | Reference Example 22 |
| 31 | Reference Example 1 | (4-pyridyl pinacol boronate) | (fluoro-bromo-pyridyl imidazo-benzoxazine) | Reference Example 22 |
| 32 | Reference Example 3 | (phenyl boronic acid) | (fluoro-bromo-phenyl imidazo-benzoxazine) | Reference Example 22 |
| 33 | Reference Example 4 | (phenyl boronic acid) | (fluoro-bromo-phenyl imidazo-benzoxazine) | Reference Example 22 |
| 34 | Reference Example 5 | (phenyl boronic acid) | (fluoro-bromo-phenyl imidazo-benzoxazine) | Reference Example 22 |
| 35 | Reference Example 6 | (phenyl boronic acid) | (bromo-phenyl imidazo-benzoxazine) | Reference Example 22 |

TABLE 2-continued

| Reference Example | Starting Material | Boric Acid or Boric Acid Ester | Desired Product | Production Method |
|---|---|---|---|---|
| 36 | Reference Example 6 | 3-thienylboronic acid | (imidazo-benzoxazine with Br and 3-thienyl) | Reference Example 22 |
| 37 | Reference Example 6 | 4-pyridyl boronic acid pinacol ester | (imidazo-benzoxazine with Br and 4-pyridyl) | Reference Example 22 |
| 38 | Reference Example 7 | phenylboronic acid | (OMe-substituted imidazo-benzoxazine with Br and phenyl) | Reference Example 22 |
| 39 | Reference Example 8 | phenylboronic acid | (MeO-substituted imidazo-benzoxazine with Br and phenyl) | Reference Example 22 |
| 40 | Reference Example 9 | phenylboronic acid | (MeO-substituted imidazo-benzoxazine with Br and phenyl) | Reference Example 22 |
| 41 | Reference Example 10 | phenylboronic acid | (MeO-substituted imidazo-benzoxazine with Br and phenyl) | Reference Example 22 |
| 42 | Reference Example 11 | phenylboronic acid | (Cl-substituted imidazo-benzoxazine with Br and phenyl) | Reference Example 22 |
| 43 | Reference Example 12 | phenylboronic acid | (OEt-substituted imidazo-benzoxazine with Br and phenyl) | Reference Example 22 |

TABLE 2-continued

| Reference Example | Starting Material | Boric Acid or Boric Acid Ester | Desired Product | Production Method |
|---|---|---|---|---|
| 44 | Reference Example 13 | phenylboronic acid | (structure) | Reference Example 22 |
| 45 | Reference Example 14 | phenylboronic acid | (structure) | Reference Example 22 |
| 46 | Reference Example 17 | phenylboronic acid | (structure) | Reference Example 22 |
| 47 | Reference Example 18 | phenylboronic acid | (structure) | Reference Example 22 |
| 48 | Reference Example 19 | phenylboronic acid | (structure) | Reference Example 22 |
| 49 | Reference Example 2 | phenylboronic acid | (structure) | Reference Example 22 |
| 50 | Reference Example 20 | phenylboronic acid | (structure) | Reference Example 22 |
| 51 | Reference Example 16 | phenylboronic acid | (structure) | Reference Example 23 |

TABLE 2-continued

| Reference Example | Starting Material | Boric Acid or Boric Acid Ester | Desired Product | Production Method |
|---|---|---|---|---|
| 52 | Reference Example 16 | phenylboronic acid | (hydroxymethyl-substituted benzo-fused imidazo-oxazine with 2-bromo-3-phenyl) | Reference Example 24 |
| 53 | Reference Example 16 | phenylboronic acid | (cyano-substituted benzo-fused imidazo-oxazine with 2-bromo-3-phenyl) | Reference Example 25 |
| 54 | Reference Example 28 | phenylboronic acid | (methyl-substituted pyrido-fused imidazo-oxazine with 2-bromo-3-phenyl) | Reference Example 22 |
| 55 | Reference Example 29 | phenylboronic acid | (methoxy-substituted pyrido-fused imidazo-oxazine with 2-bromo-3-phenyl) | Reference Example 22 |

Reference Example 56

Reference Example 56(1)

1-(4-bromophenyl)cyclobutanecarbonitrile

A solution of potassium hydroxide (56.5 g) and tetrabutylammonium bromide (2.92 g) in toluene (400 mL) and water (30 mL) was warmed to 70° C. Then, 1,3-dibromopropane (39.0 g) and 2-(4-bromophenyl)acetonitrile (35.5 g) were sequentially added thereto, and the mixture was stirred at 100° C. for 3 hours. After the reaction mixture was cooled to 80° C., heptane (100 mL) was added thereto, and the mixture was further cooled to room temperature. The reaction mixture was filtered and washed with hexane, and the organic layer was separated. The obtained organic layer was washed with saturated sodium chloride, dried over anhydrous sodium sulfate, and concentrated under reduced pressure. The obtained residue was purified by silica gel chromatography (hexane: ethyl acetate) to give the desired product (24.0 g, yield: 56%) as a colorless oil.

$^1$H-NMR (CDCl$_3$) δ: 7.53 (2H, d, J=8.8 Hz), 7.29 (2H, d, J=8.8 Hz), 2.87-2.79 (2H, m), 2.63-2.54 (2H, m), 2.50-2.38 (1H, m), 2.13-2.03 (1H, m)

ESI-MS m/z 236, 238 (MH+)

Reference Example 56(2)

1-(4-bromophenyl)cyclobutanecarboxylic acid

A 50% aqueous sodium hydroxide solution (35 mL) was added to a butanol (100 mL) solution of the product (24.0 g) of Reference Example 56(1), and the mixture was stirred at 120° C. for 14 hours. After cooling to room temperature, water (100 mL) was added to the reaction mixture, followed by washing with ether. The ether layer was further extracted twice with 1N aqueous sodium hydroxide solution (50 mL). 5 M hydrochloric acid was added to the combined aqueous layer, and the pH was adjusted to 2, followed by extraction with ethyl acetate. The combined organic layer was washed with saturated sodium chloride, dried over anhydrous sodium sulfate, and concentrated under reduced pressure. By adding hexane to the obtained residue and conducting filtration, the desired product (20.4 g, yield: 79%) was obtained as a colorless solid.

$^1$H-NMR (CDCl$_3$) δ: 7.45 (2H, d, J=8.5 Hz), 7.17 (2H, d, J=8.5 Hz), 2.88-2.79 (2H, m), 2.53-2.43 (2H, m), 2.15-2.02 (1H, m), 1.93-1.81 (1H, m)

ESI-MS m/z 255, 257 (MH+)

Reference Example 56(3)

tert-butyl 1-(4-bromophenyl)cyclobutylcarbamate

Di-tert-butoxy dicarbonate (12.0 g), sodium azide (11.3 g), tetrabutylammonium bromide (2.41 g), and zinc ditriflate (181 mg) were sequentially added to a THF (150 mL) solution of the product (12.7 g) of Reference Example 56(2), and the mixture was heated under reflux for 14 hours. The reaction mixture was cooled to room temperature, diluted with ethyl acetate and water, and extracted with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the desired product (14.7 g, yield: 91%) as a colorless solid.

$^1$H-NMR (CDCl$_3$) δ: 7.45 (2H, d, J=8.5 Hz), 7.30 (2H, d, J=8.5 Hz), 5.08 (1H, br s), 2.56-2.43 (4H, m), 2.16-2.04 (1H, m), 1.91-1.79 (1H, m), 1.37 (9H, s)

ESI-MS m/z 326, 327 (MH+)

Reference Example 56(4)

tert-butyl 1-(4-(4,4,5,5-tetramethyl-1,3,2-dioxaborolan-2-yl)phenyl)cyclobutylcarbamate Potassium acetate (2.41 g) and 4,4,4',4',5,5,5',5'-octamethyl-2,2'-bi(1,3,2-dioxaborolane) (6.25 g) are sequentially added to a DMF (25 mL) solution of the product (3.21 g) of Reference Example 56(3), and the mixture was placed in a nitrogen atmosphere. [1,1'-bis(diphenylphosphino)ferrocene]dichloropalladium(II) dichloromethane complex (360 mg) was added thereto, and the mixture was stirred at 80° C. for 10 hours. The reaction mixture was cooled to room temperature, and water was added thereto, followed by extraction with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the desired product (3.20 g, yield: 87%) as a colorless solid.

$^1$H-NMR (CDCl$_3$) δ: 7.79 (2H, d, J=8.0 Hz), 7.43 (2H, d, J=8.0 Hz), 5.07 (1H, br s), 2.59-2.31 (4H, m), 2.14-2.03 (1H, m), 1.90-1.78 (1H, m), 1.36 (9H, s), 1.34 (23H, s)

ESI-MS m/z 374 (MH+)

Reference Example 57

Reference Example 57(1)

cis-1-(4-bromophenyl)-3-hydroxycyclobutanecarboxylic acid

A THF (100 mL) solution of 4-bromophenylacetic acid (107.8 g) was added dropwise to a tetrahydrofuran solution (560 mL) of 2M isopropylmagnesium chloride with stirring under ice-cooling, and the mixture was warmed to room temperature and stirred for 1 hour. Epichlorohydrin (73 mL) was added dropwise at room temperature to the resulting suspension, and the mixture was warmed to 26° C. by the reaction heat, cooled, and stirred for 3 hours while maintaining the temperature. A THF solution (560 mL) of 2 M isopropylmagnesium chloride was added dropwise to the obtained dark-brown reaction mixture at room temperature, and the mixture was stirred overnight on a water bath. 2 M hydrochloric acid (900 mL) was carefully added to the reaction mixture under ice-cooling, and extracted with ethyl acetate. The obtained organic layer was washed with 1 M hydrochloric acid, dried over anhydrous sodium sulfate, and concentrated under reduced pressure. The obtained residue is suspended in ethyl acetate, and the solid was collected by filtration, followed by washing with ethyl acetate and drying under reduced pressure, to give the desired product (91.46 g, yield: 68%) as a colorless solid.

$^1$H-NMR (CD$_3$OD) δ: 7.49 (2H, d, J=8.8 Hz), 7.34 (2H, d, J=8.8 Hz), 4.01 (1H, quintet, J=7.3 Hz), 2.88-2.80 (2H, m), 2.69-2.61 (2H, m).

ESI-MS m/z 269 and 271 (MH–)

Reference Example 57(2)

methyl cis-1-(4-bromophenyl)-3-hydroxycyclobutanecarboxylate

The product (116.0 g) of Reference Example 57(1) was dissolved in methanol (500 mL). Concentrated sulfuric acid (3.5 mL) was added thereto at room temperature, and the mixture was heated under reflux overnight. The reaction mixture was concentrated under reduced pressure to reduce methanol, diluted with water, and extracted with ethyl acetate. The combined organic layer was washed with 1 M aqueous sodium hydroxide solution, dried over anhydrous sodium sulfate, and concentrated under reduced pressure to give the desired product (112.5 g, yield: 99%) as a light-yellow solid.

$^1$H-NMR (CDCl$_3$) δ: 7.47 (2H, d, J=8.5 Hz), 7.22 (2H, d, J=8.5 Hz), 4.19 (1H, m), 3.64 (3H, s), 2.93-2.85 (2H, m), 2.76-2.69 (2H, m), 2.21 (1H, d, J=6.3 Hz).

Reference Example 57(3)

methyl 1-(4-bromophenyl)-3-oxocyclobutylcarboxylate

The product (112.5 g) of Reference Example 57(2) was dissolved in chloroform (500 mL), and N-methylmorpholine-N-oxide (63.3 g) and powdered molecular sieves 4 A (120 g) were added thereto. The mixture was ice-cooled, tetra-n-propylammonium perruthenate (2.76 g) was added thereto, and the mixture was stirred for 24 hours while warming to room temperature. The reaction mixture was diluted with hexane, adsorbed onto silica gel, and eluted with a mixed solvent of hexane:ethyl acetate (3:1), and the eluate was concentrated under reduced pressure. The obtained light-yellow solid was suspended in hexane, and the solid was collected by filtration, followed by washing with hexane and drying under reduced pressure to give the desired product (83.4 g, yield: 69%) as a colorless solid.

$^1$H-NMR (CDCl$_3$) δ: 7.52 (2H, d, J=8.8 Hz), 7.24 (2H, d, J=8.8 Hz), 3.95-3.87 (2H, m), 3.71 (3H, s), 3.57-3.49 (2H, m)

Reference Example 57(4)

trans-3-amino-3-(4-bromophenyl)-1-cyclopropylcyclobutanol

A toluene (200 mL) solution of the product (18.57 g) of Reference Example 57(3) was cooled to −40° C., and a THF solution (310 ml) of 0.7 M cyclopropylmagnesium bromide was added dropwise thereto. After stirring at −40° C. for 15 minutes and stirring at 0° C. for 3 hours, ice, followed by a saturated aqueous ammonium chloride solution, were carefully added to the reaction mixture and extracted with ethyl acetate. The combined organic layer was dried over anhydrous sodium sulfate and concentrated under reduced pressure. The obtained residue was dissolved in 1,4-dioxane (100 mL), and 1 M aqueous sodium hydroxide solution (150 mL) was added thereto at room temperature, followed by stirring overnight. The reaction mixture was concentrated under reduced pressure, and 1,4-dioxane was removed. The aqueous layer was washed with toluene. The obtained aqueous solution was acidified with 2 M hydrochloric acid and extracted with ethyl acetate. The combined organic layer was dried over anhydrous sodium sulfate and concentrated under reduced pressure. The obtained residue was dissolved in 1,4-dioxane (215 mL), and N,N-diisopropylethylamine (7.60 mL) and diphenylphosphoryl azide (8.77 mL) were added thereto at room temperature. The mixture was stirred at room temperature for 4 hours and then at 63° C. for 4 hours, and cooled to room temperature. The obtained reaction mixture was added dropwise to vigorously stirred 0.5 M hydrochloric acid (1000 mL) and stirred at room temperature for 3 hours. The reaction mixture was washed with ethyl acetate, and the obtained aqueous solution was basified with 2 M aqueous sodium hydroxide solution. After dissolving sodium chloride to saturation, extraction with chloroform was performed. The combined organic layer was dried over anhydrous sodium sulfate and concentrated under reduced pressure to give the desired product (5.52 g, yield: 30%) as a light-yellow oil.

$^1$H-NMR (CDCl$_3$) δ: 7.46 (2H, d, J=8.8 Hz), 7.34 (2H, d, J=8.8 Hz), 2.60-2.54 (2H, m), 2.31-2.26 (2H, m), 1.36-1.29 (1H, m), 0.61-0.55 (2H, m), 0.47-0.42 (2H, m)

ESI-MS m/z 282 and 284 (MH+)

Reference Example 57(5)

2-(trans-1-(4-bromophenyl)-3-cyclopropyl-3-hydroxycyclobutyl)isoindoline-1,3-dione Triethylamine (0.52 mL) and N-ethoxycarbonylphthalimide (683 mg) was added to a chloroform (15.6 mL) solution of the product (882 mg) of Reference Example 57 (4), and the mixture was stirred at 70° C. for 38 hours. The reaction mixture was cooled, diluted with water, and extracted with chloroform. The organic layer was dried over anhydrous sodium sulfate and concentrated under reduced pressure. The obtained residue was purified by silica gel chromatography (hexane:ethyl acetate) to give the desired product (1.18 g, yield: 92%) as a colorless solid.

$^1$H-NMR (CDCl$_3$) δ: 7.77-7.73 (2H, m), 7.70-7.66 (2H, m), 7.60-7.56 (2H, m), 7.47-7.43 (2H, m), 3.11-2.99 (4H, m), 1.49 (1H, s), 1.16-1.12 (1H, m), 0.51-0.45 (2H, m), 0.32-0.27 (2H, m)

Reference Example 57(6)

2-(trans-3-cyclopropyl-3-hydroxy-1-(4-(4,4,5,5-tetramethyl-1,3,2-dioxaborolan-2-yl)phenyl)cyclobutyl)isoindoline-1,3-dione 4,4,4',4',5,5,5',5'-octamethyl-2,2'-bi(1,3,2-dioxaborolane) (1.14 g), potassium acetate (883 mg), and (1,1'-bis(diphenylphosphino)ferrocene)dichloropalladium(II) dichloromethane complex (245 mg) were added to a 1,4-dioxane (15 mL) solution of the product (1.26 g) of Reference Example 57(5), and the mixture was stirred in a nitrogen atmosphere at 80° C. for 16 hours. The reaction mixture was cooled, diluted with water, and extracted with ethyl acetate. The organic layer was dried over anhydrous sodium sulfate and concentrated under reduced pressure. The obtained residue was purified by silica gel chromatography (hexane:ethyl acetate) and concentrated under reduced pressure. The obtained solid was washed with ethyl acetate-hexane to give the desired product (1.12 g, yield: 81%) as a colorless solid.

$^1$H-NMR (CDCl$_3$) δ: 7.81-7.63 (8H, m), 3.14-3.05 (4H, m), 1.49 (1H, s), 1.32 (12H, s), 1.16-1.10 (1H, m), 0.50-0.44 (2H, m), 0.33-0.28 (2H, m).

Reference Example 58

Reference Example 58(1)

trans-1-(4-bromophenyl)-3-hydroxy-3-methylcyclobutanecarboxylic acid

A THF (210 mL) solution of the product (11.62 g) of Reference Example 57(3) was cooled to −40° C., and a THF solution (48 ml) of 3 M methylmagnesium chloride was added dropwise. After stirring at −40° C. for 15 minutes and at 0° C. for 2 hours, ice, followed by a saturated aqueous ammonium chloride solution, were carefully added to the reaction mixture and extracted with ethyl acetate. The combined organic layer was dried over anhydrous sodium sulfate and concentrated under reduced pressure. The obtained residue was dissolved in 1,4-dioxane (60 mL), and 1 M aqueous sodium hydroxide solution (62 mL) was added thereto at room temperature, followed by stirring overnight. The obtained reaction mixture was concentrated under reduced pressure to remove 1,4-dioxane and poured into 0.5 M aqueous sodium hydroxide solution, and the aqueous layer was washed with ethyl acetate. The obtained basic aqueous solution was acidified with 2 M hydrochloric acid and extracted with ethyl acetate. The combined organic layer was dried over anhydrous sodium sulfate and concentrated under reduced pressure. The obtained residue was crystallized from a mixed solvent of chloroform:hexane to give the desired product (5.92 g, yield: 51%) as a colorless solid.

$^1$H-NMR (CDCl$_3$) δ: 7.45 (2H, d, J=8.5 Hz), 7.17 (2H, d, J=8.5 Hz), 3.09-3.04 (2H, m), 2.62-2.56 (2H, m), 1.43 (3H, s).

ESI-MS m/z 283 and 285 (MH−)

Reference Example 58(2)

trans-3-amino-3-(4-bromophenyl)-1-methylcyclobutanol

Triethylamine (2.20 mL) and diphenylphosphoryl azide (3.40 mL) were added to a 1,4-dioxane (60 mL) solution of the product (4.28 g) of Reference Example 58(1), and the mixture was stirred at 80° C. for 2 hours. The reaction mixture was cooled to room temperature and added to ice-cooled 1 M hydrochloric acid (60 mL), and the mixture was stirred at room temperature for 2 hours. Water was added to the reaction mixture, and the mixture was washed with diethyl ether, basified with 5 M sodium hydroxide solution, and extracted with chloroform. The combined organic layer was dried over anhydrous sodium sulfate and concentrated under reduced pressure to give the desired product (3.23 g, yield: 84%) as a colorless oil.

$^1$H-NMR (CDCl$_3$) δ: 7.49-7.43 (2H, m), 7.27-7.22 (2H, m), 2.64-2.57 (2H, m), 2.40-2.33 (2H, m), 1.64 (3H, s).

ESI-MS m/z 256, 258 (MH+)

Reference Example 58(3)

tert-butyl trans-1-(4-bromophenyl)-3-hydroxy-3-methylcyclobutylcarbamate

Di-tert-butyl dicarbonate (3.30 g) was added to a 1,4-dioxane (63 mL) solution of the product (3.23 g) of Reference Example 58(2), and the mixture was stirred at 70° C. for 3 hours. The reaction mixture was concentrated under reduced pressure and recrystallized from hexane-ethyl acetate to give the desired product (3.50 g, yield: 78%) as a colorless solid.

¹H-NMR (CDCl₃) δ: 7.47-7.42 (2H, m), 7.28 (2H, d, J=8.5 Hz), 4.96 (1H, br s), 2.77-2.47 (4H, m), 1.67 (1H, s), 1.58 (3H, s), 1.38 (9H, br s).
ESI-MS m/z 356, 358 (MH+)

Reference Example 58(4)

tert-butyl trans-3-hydroxy-3-methyl-1-(4-(4,4,5,5-tetramethyl-1,3,2-dioxaborolan-2-yl)phenyl)cyclobutylcarbamate 4,4,4',4',5,5,5',5'-octamethyl-2,2'-bi(1,3,2-dioxaborolane) (3.47 g) and potassium acetate (3.09 g) were added to a DMF (42 mL) solution of the product (3.74 g) of Reference Example 58(3), and the mixture was placed in a nitrogen atmosphere. [1,1'-bis(diphenylphosphino)ferrocene]dichloropalladium(II) dichloromethane complex (0.43 g) was added thereto, and the mixture was stirred at 80° C. for 5 hours. The reaction mixture was cooled to room temperature, and water was added thereto, followed by extraction with ethyl acetate. The combined organic layer was washed with saturated sodium chloride, dried over anhydrous sodium sulfate, and concentrated under reduced pressure. The obtained residue was purified by silica gel chromatography (hexane:ethyl acetate) to give the desired product (3.39 g, yield: 80%) as a colorless solid.
¹H-NMR (CDCl₃) δ: 7.78 (2H, d, J=8.1 Hz), 7.41 (2H, d, J=8.1 Hz), 4.95 (1H, br s), 2.78-2.49 (4H, m), 1.65 (1H, s), 1.58 (3H, s), 1.37 (9H, br s), 1.34 (12H, s).
ESI-MS m/z 404 (MH+)

Reference Example 59 tert-butyl trans-3-ethyl-3-hydroxy-1-(4-(4,4,5,5-tetramethyl-1,3,2-dioxaborolan-2-yl)phenyl)cyclobutylcarbamate The desired product was obtained as a colorless solid by reacting the product of Reference Example 57(3) in the same manner as in Reference Example 58, but using ethylmagnesium bromide in place of the methylmagnesium chloride of Reference Example 58(1).
¹H-NMR (CDCl₃) δ: 7.78 (2H, d, J=7.8 Hz), 7.43 (2H, d, J=7.8 Hz), 4.92 (1H, brs), 2.80-2.45 (4H, m), 1.83 (2H, q, J=7.2 Hz), 1.53 (1H, s), 1.45-1.25 (9H, m), 1.34 (12H, s), 0.97 (3H, t, J=7.2 Hz)
ESI-MS m/z 418 (MH+)

Example 1 trans-3-amino-1-cyclopropyl-3-(4-(10-fluoro-3-phenyl-5H-benzo[e]imidazo[1,2-c][1,3]oxazin-2-yl)phenyl)cyclobutanol The product (30.0 mg) of Reference Example 57(6) and cesium carbonate (35.4 mg) were added to a solution of the product (15.0 mg) of Reference Example 22(2) in 1,4-dioxane (1.0 mL) and water (0.13 mL), and the mixture was placed in a nitrogen atmosphere. Pd(PPh3)4 (5.0 mg) was then added thereto, and the mixture was stirred at 100° C. for 2 hours. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the corresponding coupling product. The obtained coupling product was used for the next reaction without further purification. Hydrazine monohydrate (0.5 mL) was added to an ethanol (2.0 mL) solution of the obtained coupling product, and the mixture was stirred at 110° C. for 20 minutes using a microwave reactor. The reaction mixture was cooled to room temperature, diluted with saturated sodium hydrogen carbonate, and extracted with chloroform. The combined organic layer was washed with saturated sodium chloride, dried over anhydrous sodium sulfate, and concentrated under reduced pressure. The obtained residue was purified by preparative reversed-phase high-performance liquid chromatography (0.1% trifluoroacetic acid, acetonitrile/water) and concentrated under reduced pressure. Subsequently, desalting treatment was carried out using Bond Elut (registered trademark) (methanol) manufactured by Varian, Inc. to give the title compound (16.8 mg, yield: 83%) as a colorless solid.
¹H-NMR (CDCl₃) δ: 7.60 (2H, d, J=8.3 Hz), 7.48 (1H, dd, J=5.0, 3.0 Hz), 7.38-7.32 (3H, m), 7.28-7.23 (1H, m), 7.08 (1H, dd, J=5.0, 1.3 Hz), 6.99-6.93 (1H, m), 6.92-6.88 (1H, m), 5.69 (2H, s), 2.64-2.58 (2H, m), 2.33-2.27 (2H, m), 1.34 (1H, tt, J=8.3, 5.4 Hz), 0.59-0.53 (2H, m), 0.48-0.43 (2H, m).
ESI-MS m/z 468 (MH+)

Example 2 trans-3-amino-3-(4-(10-fluoro-3-phenyl-5H-benzo[e]imidazo[1,2-c][1,3]oxazin-2-yl)phenyl)-1-methylcyclobutanol The product (28.3 mg) of Reference Example 58(4) and cesium carbonate (35.4 mg) were added to a solution of the product (15.0 mg) of Reference Example 22(2) in 1,4-dioxane (1.0 mL) and water (0.13 mL), and the mixture was placed in a nitrogen atmosphere. Pd(PPh3)4 (5.0 mg) was then added thereto, and the mixture was stirred at 100° C. for 2 hours. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the corresponding coupling product. The obtained coupling product was used for the next reaction without further purification. Trifluoroacetic acid (0.5 mL) was added to a chloroform (1.0 mL) solution of the obtained coupling product, and the mixture was stirred at room temperature for 1 hour. The reaction mixture was concentrated under reduced pressure, and the obtained residue was purified by preparative reversed-phase high-performance liquid chromatography (0.1% trifluoroacetic acid, acetonitrile/water) and concentrated under reduced pressure. Subsequently, desalting treatment was carried out using Bond Elut (registered trademark) (methanol) manufactured by Varian, Inc. to give the title compound (15.2 mg, yield: 79%) as a colorless solid.
¹H-NMR (CDCl₃) δ: 7.57-7.53 (2H, m), 7.50-7.42 (3H, m), 7.38-7.33 (2H, m), 7.28-7.20 (3H, m), 6.99-6.93 (1H, m), 6.91-6.87 (1H, m), 5.65 (2H, s), 2.63-2.58 (2H, m), 2.39-2.32 (2H, m), 1.62 (3H, s).
ESI-MS m/z 442 (MH+)

Example 3

1-(4-(10-fluoro-3-phenyl-5H-benzo[e]imidazo[1,2-c][1,3]oxazin-2-yl)phenyl)cyclobutanamine Using the product of Reference Example 22(2) and in the same manner as in Example 2, but using the product of Reference Example 56(4) in place of the product of Reference Example 58(4), the title compound was obtained as a colorless solid.

$^1$H-NMR (CDCl$_3$) δ: 7.57 (2H, d, J=8.3 Hz), 7.51-7.44 (3H, m), 7.39-7.35 (2H, m), 7.30-7.22 (3H, m), 7.00-6.94 (1H, m), 6.92-6.88 (1H, m), 5.66 (2H, s), 2.57-2.48 (2H, m), 2.17-1.99 (3H, m), 1.78-1.69 (1H, m).

ESI-MS m/z 412 (MH+)

Example 4 trans-3-amino-1-cyclopropyl-3-(4-(10-fluoro-3-(thiophen-3-yl)-5H-benzo[e]imidazo[1,2-c][1,3]oxazin-2-yl)phenyl)cyclobutanol Using the product of Reference Example 30 and in the same manner as in Example 1, the title compound was obtained as a colorless solid.

$^1$H-NMR (CDCl$_3$) δ: 7.60 (2H, d, J=8.3 Hz), 7.48 (1H, dd, J=5.0, 3.0 Hz), 7.38-7.32 (3H, m), 7.28-7.23 (1H, m), 7.08 (1H, dd, J=5.0, 1.3 Hz), 6.99-6.93 (1H, m), 6.92-6.88 (1H, m), 5.69 (2H, s), 2.64-2.58 (2H, m), 2.33-2.27 (2H, m), 1.34 (1H, tt, J=8.3, 5.4 Hz), 0.59-0.53 (2H, m), 0.48-0.43 (2H, m).

ESI-MS m/z 474 (MH+)

Example 5 trans-3-amino-1-cyclopropyl-3-(4-(10-fluoro-3-(pyridin-4-yl)-5H-benzo[e]imidazo[1,2-c][1,3]oxazin-2-yl)phenyl)cyclobutanol Using the product of Reference Example 31 and in the same manner as in Example 1, the title compound was obtained as a colorless solid.

$^1$H-NMR (CDCl$_3$) δ: 8.71 (2H, d, J=6.1 Hz), 7.53 (2H, d, J=8.5 Hz), 7.37 (2H, d, J=8.5 Hz), 7.33-7.24 (3H, m), 7.01-6.91 (2H, m), 5.74 (2H, s), 2.64-2.58 (2H, m), 2.34-2.28 (2H, m), 1.35 (1H, tt, J=8.3, 5.4 Hz), 0.60-0.54 (2H, m), 0.49-0.44 (2H, m).

ESI-MS m/z 469 (MH+)

Example 6 trans-3-amino-3-(4-(10-fluoro-3-(thiophen-3-yl)-5H-benzo[e]imidazo[1,2-c][1,3]oxazin-2-yl)phenyl)-1-methylcyclobutanol Using the product of Reference Example 30 and in the same manner as in Example 2, the title compound was obtained as a colorless solid.

$^1$H-NMR (CDCl$_3$) δ: 7.59 (2H, d, J=8.5 Hz), 7.48 (1H, dd, J=4.9, 2.9 Hz), 7.33 (1H, dd, J=3.0, 1.3 Hz), 7.29-7.23 (3H, m), 7.08 (1H, dd, J=4.9, 1.3 Hz), 6.99-6.93 (1H, m), 6.92-6.88 (1H, m), 5.69 (2H, s), 2.66-2.60 (2H, m), 2.41-2.34 (2H, m), 1.64 (3H, s).

ESI-MS m/z 448 (MH+)

Example 7 trans-3-amino-3-(4-(10-fluoro-3-(pyridin-4-yl)-5H-benzo[e]imidazo[1,2-c][1,3]oxazin-2-yl)phenyl)-1-methylcyclobutanol Using the product of Reference Example 31 and in the same manner as in Example 2, the title compound was obtained as a colorless solid.

$^1$H-NMR (CDCl$_3$) δ: 8.68 (2H, d, J=5.9 Hz), 7.51 (2H, d, J=8.3 Hz), 7.32-7.22 (5H, m), 7.00-6.90 (2H, m), 5.73 (2H, s), 2.66-2.60 (3H, m), 2.41-2.35 (2H, m), 1.64 (3H, s).

ESI-MS m/z 443 (MH+)

Example 8 trans-3-amino-3-(4-(9-fluoro-3-phenyl-5H-benzo[e]imidazo[1,2-c][1,3]oxazin-2-yl)phenyl)-1-methylcyclobutanol Using the product of Reference Example 32 and in the same manner as in Example 2, the title compound was obtained as a colorless solid.

$^1$H-NMR (CDCl$_3$) δ: 7.80-7.76 (1H, m), 7.55-7.43 (5H, m), 7.37-7.33 (2H, m), 7.25-7.21 (2H, m), 7.05-6.96 (2H, m), 5.65 (2H, s), 2.64-2.58 (2H, m), 2.38-2.32 (2H, m), 1.62 (3H, s).

ESI-MS m/z 443 (MH+)

Example 9 trans-3-amino-3-(4-(8-fluoro-3-phenyl-5H-benzo[e]imidazo[1,2-c][1,3]oxazin-2-yl)phenyl)-1-methylcyclobutanol Using the product of Reference Example 33 and in the same manner as in Example 2, the title compound was obtained as a colorless solid.

$^1$H-NMR (CDCl$_3$) δ: 8.07 (1H, dd, J=8.5, 6.1 Hz), 7.55-7.33 (7H, m), 7.24 (2H, d, J=8.3 Hz), 6.92 (1H, td, J=8.7, 2.4 Hz), 6.84-6.79 (1H, m), 5.68 (2H, s), 2.65-2.59 (2H, m), 2.39-2.34 (2H, m), 1.63 (3H, s).

ESI-MS m/z 443 (MH+)

Example 10 trans-3-amino-1-cyclopropyl-3-(4-(7-fluoro-3-phenyl-5H-benzo[e]imidazo[1,2-c][1,3]oxazin-2-yl)phenyl)cyclobutanol Using the product of Reference Example 34 and in the same manner as in Example 1, the title compound was obtained as a colorless solid.

$^1$H-NMR (CDCl$_3$) δ: 7.88-7.85 (1H, m), 7.55 (2H, d, J=8.5 Hz), 7.51-7.45 (3H, m), 7.38-7.32 (4H, m), 7.15-7.10 (2H, m), 5.73 (2H, s), 2.63-2.57 (2H, m), 2.32-2.27 (2H, m), 1.34 (1H, tt, J=8.3, 5.4 Hz), 0.59-0.53 (2H, m), 0.48-0.43 (2H, m).

ESI-MS m/z 468 (MH+)

Example 11 trans-3-amino-1-cyclopropyl-3-(4-(3-phenyl-5H-benzo[e]imidazo[1,2-c][1,3]oxazin-2-yl)phenyl)cyclobutanol Using the product of Reference Example 35 and in the same manner as in Example 1, the title compound was obtained as a colorless solid.

$^1$H-NMR (CDCl$_3$) δ: 8.09 (1H, dd, J=7.7, 1.6 Hz), 7.58-7.29 (10H, m), 7.21-7.16 (1H, m), 7.07 (1H, dd, J=8.0, 1.0

Hz), 5.67 (2H, s), 2.62-2.56 (2H, m), 2.31-2.25 (2H, m), 1.33 (1H, tt, J=8.3, 5.4 Hz), 0.58-0.52 (2H, m), 0.42-0.47 (2H, m).
ESI-MS m/z 450 (MH+)

Example 12 trans-3-amino-1-methyl-3-(4-(3-phenyl-5H-benzo[e]imidazo[1,2-c][1,3]oxazin-2-yl)phenyl)cyclobutanol Using the product of Reference Example 35 and in the same manner as in Example 2, the title compound was obtained as a colorless solid.
$^1$H-NMR (CDCl$_3$) δ: 8.09 (1H, dd, J=7.7, 1.6 Hz), 7.56-7.43 (5H, m), 7.37-7.29 (3H, m), 7.25-7.16 (3H, m), 7.06 (1H, dd, J=8.3, 1.0 Hz), 5.67 (2H, s), 2.64-2.58 (2H, m), 2.38-2.32 (2H, m), 1.62 (3H, s).
ESI-MS m/z 424 (MH+)

Example 13

1-(4-(3-phenyl-5H-benzo[e]imidazo[1,2-c][1,3]oxazin-2-yl)phenyl)cyclobutanamine

Using the product of Reference Example 35 and in the same manner as in Example 2, but using the product of Reference Example 56(4) in place of the product of Reference Example 58(4), the title compound was obtained as a colorless solid.
$^1$H-NMR (CDCl$_3$) δ: 8.09 (1H, dd, J=7.7, 1.6 Hz), 7.55 (2H, d, J=8.5 Hz), 7.50-7.43 (3H, m), 7.39-7.27 (5H, m), 7.22-7.17 (1H, m), 7.07 (1H, dd, J=8.0, 1.0 Hz), 5.68 (2H, s), 2.58-2.49 (2H, m), 2.19-2.00 (3H, m), 1.79-1.71 (1H, m).
ESI-MS m/z 394 (MH+)

Example 14

1-(4-(3-(thiophen-3-yl)-5H-benzo[e]imidazo[1,2-c][1,3]oxazin-2-yl)phenyl)cyclobutanamine Using the product of Reference Example 36 and in the same manner as in Example 2, but using the product of Reference Example 56(4) in place of the product of Reference Example 58(4), the title compound was obtained as a colorless solid.
$^1$H-NMR (CDCl$_3$) δ: 8.07 (1H, dd, J=8.0, 1.6 Hz), 7.59-7.57 (2H, m), 7.47 (1H, dd, J=4.8, 2.8 Hz), 7.34-7.30 (4H, m), 7.21 (1H, ddd, J=7.6, 7.6, 1.2 Hz), 7.10-7.06 (2H, m), 5.71 (2H, s), 2.58-2.51 (2H, m), 2.17-2.03 (3H, m), 1.79-1.70 (1H, m).
ESI-MS m/z 400 (MH+)

Example 15

1-(4-(3-(pyridin-4-yl)-5H-benzo[e]imidazo[1,2-c][1,3]oxazin-2-yl)phenyl)cyclobutanamine Using the product of Reference Example 37 and in the same manner as in Example 2, but using the product of Reference Example 56(4) in place of the product of Reference Example 58(4), the title compound was obtained as a colorless solid.
$^1$H-NMR (CDCl$_3$) δ: 8.69 (2H, dd, J=4.4, 1.6 Hz), 8.09 (1H, dd, J=7.6, 1.6 Hz), 7.52 (2H, d, J=7.6 Hz), 7.38-7.34 (3H, m), 7.27-7.26 (2H, m), 7.21 (1H, ddd, J=7.6, 7.6, 1.2 Hz), 7.10 (1H, dd, J=7.6, 1.2 Hz), 5.76 (2H, s), 2.58-2.52 (2H, m), 2.19-2.02 (3H, m), 1.79-1.70 (1H, m).
ESI-MS m/z 395 (MH+)

Example 16 trans-3-amino-1-cyclopropyl-3-(4-(10-methoxy-3-phenyl-5H-benzo[e]imidazo[1,2-c][1,3]oxazin-2-yl)phenyl)cyclobutanol Using the product of Reference Example 36 and in the same manner as in Example 1, the title compound was obtained as a colorless solid.
$^1$H-NMR (CDCl$_3$) δ: 7.59 (2H, d, J=8.3 Hz), 7.49-7.43 (3H, m), 7.38-7.35 (2H, m), 7.32-7.23 (3H, m), 6.77 (1H, dd, J=8.5, 0.7 Hz), 6.72 (1H, dd, J=8.0, 0.7 Hz), 5.58 (2H, s), 4.06 (3H, s), 2.62-2.56 (2H, m), 2.31-2.25 (2H, m), 1.33 (1H, tt, J=8.3, 5.4 Hz), 0.58-0.42 (4H, m).
ESI-MS m/z 480 (MH+)

Example 17 trans-3-amino-1-cyclopropyl-3-(4-(9-methoxy-3-phenyl-5H-benzo[e]imidazo[1,2-c][1,3]oxazin-2-yl)phenyl)cyclobutanol Using the product of Reference Example 39 and in the same manner as in Example 1, the title compound was obtained as a colorless solid.
$^1$H-NMR (CDCl$_3$) δ: 7.61-7.53 (3H, m), 7.50-7.41 (3H, m), 7.39-7.31 (4H, m), 7.00 (1H, d, J=8.8 Hz), 6.68 (1H, dd, J=9.0, 2.9 Hz), 5.63 (2H, s), 3.89 (3H, s), 2.64-2.57 (2H, m), 2.33-2.26 (2H, m), 1.38-1.29 (1H, m), 0.60-0.42 (4H, m).
ESI-MS m/z 480 (MH+)

Example 18 trans-3-amino-1-cyclopropyl-3-(4-(8-methoxy-3-phenyl-5H-benzo[e]imidazo[1,2-c][1,3]oxazin-2-yl)phenyl)cyclobutanol Using the product of Reference Example 40 and in the same manner as in Example 1, the title compound was obtained as a colorless solid.
$^1$H-NMR (CDCl$_3$) δ: 8.00 (1H, d, J=8.5 Hz), 7.54 (2H, d, J=8.3 Hz), 7.49-7.40 (3H, m), 7.38-7.30 (4H, m), 6.76 (1H, dd, J=8.7, 2.3 Hz), 6.62 (1H, d, J=2.2 Hz), 5.64 (2H, s), 3.85 (3H, s), 2.63-2.57 (2H, m), 2.32-2.26 (2H, m), 1.38-1.28 (1H, m), 0.59-0.42 (4H, m).
ESI-MS m/z 480 (MH+)

Example 19 trans-3-amino-1-cyclopropyl-3-(4-(7-methoxy-3-phenyl-5H-benzo[e]imidazo[1,2-c][1,3]oxazin-2-yl)phenyl)cyclobutanol Using the product of Reference Example 41 and in the same manner as in Example 1, the title compound was obtained as a colorless solid.
$^1$H-NMR (CDCl$_3$) δ: 7.71 (1H, dd, J=7.8, 1.0 Hz), 7.55 (2H, d, J=8.3 Hz), 7.50-7.41 (3H, m), 7.38-7.30 (4H, m), 7.18-7.11 (1H, m), 6.95 (1H, dd, J=8.3, 1.2 Hz), 5.71 (2H, s), 3.93 (3H, s), 2.63-2.57 (2H, m), 2.32-2.26 (2H, m), 1.38-1.29 (1H, m), 0.59-0.42 (4H, m).
ESI-MS m/z 480 (MH+)

Example 20 trans-3-amino-3-(4-(9-methoxy-3-phenyl-5H-benzo[e]imidazo[1,2-c][1,3]oxazin-2-yl)phenyl)-1-methylcyclobutanol Using the product of Reference Example 39 and in the same manner as in Example 2, the title compound was obtained as a colorless solid.

$^1$H-NMR (CDCl$_3$) δ: 7.59 (1H, d, J=2.9 Hz), 7.53 (2H, d, J=8.5 Hz), 7.49-7.42 (3H, m), 7.37-7.32 (2H, m), 7.25 (2H, d, J=8.5 Hz), 6.99 (1H, d, J=9.0 Hz), 6.87 (1H, dd, J=9.0, 2.9 Hz), 5.62 (2H, s), 3.88 (3H, s), 2.65-2.59 (2H, m), 2.41-2.35 (2H, m), 1.62 (3H, s).

ESI-MS m/z 454 (MH+)

Example 21 trans-3-amino-3-(4-(8-methoxy-3-phenyl-5H-benzo[e]imidazo[1,2-c][1,3]oxazin-2-yl)phenyl)-1-methylcyclobutanol Using the product of Reference Example 40 and in the same manner as in Example 2, the title compound was obtained as a colorless solid.

$^1$H-NMR (CDCl$_3$) δ: 8.00 (1H, d, J=8.5 Hz), 7.52 (2H, d, J=8.3 Hz), 7.48-7.40 (3H, m), 7.36-7.32 (2H, m), 7.24 (2H, d, J=8.3 Hz), 6.76 (1H, dd, J=8.5, 2.4 Hz), 6.61 (1H, d, J=2.4 Hz), 5.63 (2H, s), 3.84 (3H, s), 2.64-2.58 (2H, m), 2.39-2.33 (2H, m), 1.62 (3H, s).

ESI-MS m/z 454 (MH+)

Example 22 trans-3-amino-3-(4-(10-chloro-3-phenyl-5H-benzo[e]imidazo[1,2-c][1,3]oxazin-2-yl)phenyl)-1-cyclopropylcyclobutanol Using the product of Reference Example 42 and in the same manner as in Example 1, the title compound was obtained as a colorless solid.

$^1$H-NMR (CDCl$_3$) δ: 7.60 (2H, d, J=8.3 Hz), 7.51-7.44 (3H, m), 7.39-7.30 (4H, m), 7.27-7.18 (2H, m), 7.00 (1H, dd, J=7.9, 1.3 Hz), 5.62 (2H, s), 2.63-2.57 (2H, m), 2.33-2.27 (2H, m), 1.33 (1H, tt, J=8.5, 5.6 Hz), 0.58-0.52 (2H, m), 0.47-0.42 (2H, m).

ESI-MS m/z 484 (MH+)

Example 23 trans-3-amino-1-cyclopropyl-3-(4-(10-ethoxy-3-phenyl-5H-benzo[e]imidazo[1,2-c][1,3]oxazin-2-yl)phenyl)cyclobutanol Using the product of Reference Example 43 and in the same manner as in Example 1, the title compound was obtained as a colorless solid.

$^1$H-NMR (CDCl$_3$) δ: 7.60 (2H, d, J=8.4 Hz), 7.50-7.41 (3H, m), 7.39-7.35 (2H, m), 7.30 (2H, d, J=8.4 Hz), 7.22 (1H, dd, J=8.4, 8.2 Hz), 6.75 (1H, d, J=8.4 Hz), 6.70 (1H, d, J=8.2 Hz), 5.55 (2H, s), 4.28 (2H, q, J=7.0 Hz), 2.62-2.56 (2H, m), 2.32-2.26 (2H, m), 1.63 (3H, t, J=7.0 Hz), 1.37-1.28 (1H, m), 0.57-0.42 (4H, m).

ESI-MS m/z 494 (MH+)

Example 24 trans-3-amino-3-(4-(10-ethoxy-3-phenyl-5H-benzo[e]imidazo[1,2-c][1,3]oxazin-2-yl)phenyl)-1-methylcyclobutanol Using the product of Reference Example 43 and in the same manner as in Example 2, the title compound was obtained as a colorless solid.

$^1$H-NMR (CDCl$_3$) δ: 7.60 (2H, d, J=8.6 Hz), 7.50-7.42 (3H, m), 7.39-7.35 (2H, m), 7.25-7.19 (3H, m), 6.76 (1H, dd, J=8.4, 0.8 Hz), 6.70 (1H, dd, J=8.2, 0.8 Hz), 5.55 (2H, s), 4.28 (2H, d, J=7.0 Hz), 2.64-2.59 (2H, m), 2.38-2.32 (2H, m), 1.63 (3H, t, J=7.0 Hz), 1.62 (3H, s)

ESI-MS m/z 468 (MH+)

Example 25 trans-3-amino-1-cyclopropyl-3-(4-(8,10-dimethoxy-3-phenyl-5H-benzo[e]imidazo[1,2-c][1,3]oxazin-2-yl)phenyl)cyclobutanol Using the product of Reference Example 44 and in the same manner as in Example 1, the title compound was obtained as a colorless solid.

$^1$H-NMR (CDCl$_3$) δ: 7.56-7.52 (2H, m), 7.46-7.41 (3H, m), 7.35-7.24 (4H, m), 6.32 (1H, d, J=2.2 Hz), 6.27 (1H, d, J=2.2 Hz), 5.56 (2H, s), 3.98 (3H, s), 3.84 (3H, s), 2.64-2.56 (2H, m), 2.38-2.30 (2H, m), 1.35-1.25 (1H, m), 0.55-0.49 (2H, m), 0.46-0.40 (2H, m)

ESI-MS m/z 510 (MH+)

Example 26 trans-3-amino-1-cyclopropyl-3-(4-(7-methyl-3-phenyl-5H-benzo[e]imidazo[1,2-c][1,3]oxazin-2-yl)phenyl)cyclobutanol Using the product of Reference Example 45 and in the same manner as in Example 1, the title compound was obtained as a colorless solid.

$^1$H-NMR (CDCl$_3$) δ: 7.93 (1H, d, J=6.6 Hz), 7.56 (2H, d, J=8.5 Hz), 7.49-7.42 (3H, m), 7.39-7.35 (2H, m), 7.33 (2H, d, J=8.5 Hz), 7.19-7.16 (1H, m), 7.11-7.06 (1H, m), 5.69 (2H, s), 2.62-2.57 (2H, m), 2.32-2.27 (2H, m), 1.34 (1H, tt, J=8.0, 5.4 Hz), 0.59-0.53 (2H, m), 0.48-0.43 (2H, m)

ESI-MS m/z 464 (MH+)

Example 27 trans-3-amino-1-cyclopropyl-3-(4-(3-phenyl-5H-imidazo[1,2-c]pyrido[2,3-e][1,3]oxazin-2-yl)phenyl)cyclobutanol Using the product of Reference Example 46 and in the same manner as in Example 1, the title compound was obtained as a colorless solid.

$^1$H-NMR (CDCl$_3$) δ: 8.49 (1H, dd, J=4.8, 1.6 Hz), 7.68 (2H, d, J=8.0 Hz), 7.52-7.48 (3H, m), 7.41-7.38 (3H, m), 7.30 (2H, d, J=8.0 Hz), 7.25 (1H, dd, J=8.0, 4.8 Hz), 5.71 (2H, s), 2.62-2.58 (2H, m), 2.31-2.28 (2H, m), 1.38-1.31 (1H, m), 0.58-0.53 (2H, m), 0.47-0.44 (2H, m)

ESI-MS m/z 451 (MH+)

Example 28 trans-3-amino-1-methyl-3-(4-(3-phenyl-5H-imidazo[1,2-c]pyrido[2,3-e][1,3]oxazin-2-yl)phenyl)cyclobutanol Using the product of Reference Example 46 and in the same manner as in Example 2, the title compound was obtained as a colorless solid.
$^1$H-NMR (CDCl$_3$) δ: 8.49 (1H, dd, J=4.8, 1.6 Hz), 7.67 (2H, d, J=8.0 Hz), 7.52-7.48 (3H, m), 7.42-7.37 (3H, m), 7.26-7.20 (3H, m), 5.71 (2H, s), 2.63-2.60 (2H, m), 2.38-2.34 (2H, m), 1.64 (3H, s)
ESI-MS m/z 425 (MH+)

Example 29

1-(4-(3-phenyl-5H-imidazo[1,2-c]pyrido[2,3-e][1,3]oxazin-2-yl)phenyl)cyclobutanamine Using the product of Reference Example 46 and in the same manner as in Example 2, but using the product of Reference Example 56(4) in place of the product of Reference Example 58(4), the title compound was obtained as a colorless solid.
$^1$H-NMR (CDCl$_3$) δ: 8.49 (1H, dd, J=4.8, 1.3 Hz), 7.67 (2H, d, J=8.5 Hz), 7.52-7.47 (3H, m), 7.43-7.36 (3H, m), 7.28-7.22 (3H, m), 5.71 (2H, s), 2.57-2.49 (2H, m), 2.16-2.00 (3H, m), 1.79-1.69 (1H, m)
ESI-MS m/z 395 (MH+)

Example 30 trans-3-amino-1-ethyl-3-(4-(3-phenyl-5H-imidazo[1,2-c]pyrido[2,3-e][1,3]oxazin-2-yl)phenyl)cyclobutanol Using the product of Reference Example 46 and in the same manner as in Example 2, but using the product of Reference Example 59 in place of the product of Reference Example 58(4), the title compound was obtained as a colorless solid.
$^1$H-NMR (CDCl$_3$) δ: 8.49 (1H, dd, J=4.4, 1.6 Hz), 7.67 (2H, d, J=8.0 Hz), 7.52-7.48 (3H, m), 7.41-7.36 (3H, m), 7.29-7.21 (3H, m), 5.71 (2H, s), 2.57-2.54 (2H, m), 2.37-2.34 (2H, m), 1.91 (2H, q, J=7.2 Hz), 0.97 (3H, t, J=7.2 Hz)
ESI-MS m/z 439 (MH+)

Example 31 trans-3-amino-1-cyclopropyl-3-(4-(3-phenyl-5H-imidazo[1,2-c]pyrido[2,3-e][1,3]oxazin-2-yl)phenyl)cyclobutanol Using the product of Reference Example 47 and in the same manner as in Example 1, the title compound was obtained as a colorless solid.
$^1$H-NMR (CDCl$_3$) δ: 8.49 (1H, dd, J=4.8, 1.6 Hz), 7.68 (2H, d, J=8.0 Hz), 7.52-7.48 (3H, m), 7.41-7.38 (3H, m), 7.30 (2H, d, J=8.0 Hz), 7.25 (1H, dd, J=8.0, 4.8 Hz), 5.71 (2H, s), 2.62-2.58 (2H, m), 2.31-2.28 (2H, m), 1.38-1.31 (1H, m), 0.58-0.53 (2H, m), 0.47-0.44 (2H, m)
ESI-MS m/z 451 (MH+)

Example 32 trans-3-amino-1-methyl-3-(4-(3-phenyl-5H-imidazo[1,2-c]pyrido[3,4-e][1,3]oxazin-2-yl)phenyl)cyclobutanol Using the product of Reference Example 47 and in the same manner as in Example 2, the title compound was obtained as a colorless solid.
$^1$H-NMR (CDCl$_3$) δ: 9.26 (1H, s), 8.49 (1H, d, J=5.6 Hz) 7.58-7.44 (5H, m), 7.40-7.33 (2H, m), 7.29-7.22 (2H, m), 6.99 (1H, d, J=5.6 Hz), 5.76 (2H, s), 2.66-2.58 (2H, m), 2.40-2.33 (2H, m), 1.64 (3H, s), 1.61 (3H, brs).
ESI-MS m/z 425 (MH+)

Example 33

1-(4-(3-phenyl-5H-imidazo[1,2-c]pyrido[3,4-e][1,3]oxazin-2-yl)phenyl)cyclobutanamine Using the product of Reference Example 47 and in the same manner as in Example 2, but using the product of Reference Example 56(4) in place of the product of Reference Example 58(4), the title compound was obtained as a colorless solid.
$^1$H-NMR (CDCl$_3$) δ: 9.27 (1H, s), 8.50 (1H, d, J=5.6 Hz), 7.58 (5H, m), 7.40-7.25 (4H, m), 7.00 (1H, d, J=5.6 Hz), 5.76 (2H, s), 2.59-2.48 (2H, m), 2.20-1.98 (3H, m), 1.82-1.69 (1H, m)
ESI-MS m/z 395 (MH+)

Example 34 trans-3-amino-1-ethyl-3-(4-(3-phenyl-5H-imidazo[1,2-c]pyrido[3,4-e][1,3]oxazin-2-yl)phenyl)cyclobutanol Using the product of Reference Example 47 and in the same manner as in Example 2, but using the product of Reference Example 59 in place of the product of Reference Example 58(4), the title compound was obtained as a colorless solid.
$^1$H-NMR (CDCl$_3$) δ: 9.27 (1H, s), 8.49 (1H, d, J=5.6 Hz), 7.59-7.44 (5H, m), 7.40-7.34 (2H, m), 7.29 (2H, d, J=8.3 Hz), 7.00 (1H, d, J=5.6 Hz), 5.76 (2H, s), 2.60-2.53 (2H, m), 2.40-2.33 (2H, m), 1.90 (2H, q, J=7.3 Hz), 1.62 (3H, br s), 0.97 (3H, t, J=7.3 Hz)
ESI-MS m/z 439 (MH+)

Example 35 trans-3-amino-1-cyclopropyl-3-(4-(3-phenyl-5H-imidazo[1,2-c]pyrido[4,3-e][1,3]oxazin-2-yl)phenyl)cyclobutanol Using the product of Reference Example 48 and in the same manner as in Example 1, the title compound was obtained as a colorless solid.
$^1$H-NMR (CDCl$_3$) δ: 9.26 (1H, s), 8.49 (1H, d, J=5.6 Hz), 7.59-7.43 (5H, m), 7.40-7.32 (4H, m), 6.99 (1H, d, J=5.6 Hz), 5.76 (2H, s), 2.63-2.57 (2H, m), 2.33-2.26 (2H, m), 1.61 (3H, br s), 1.34 (1H, tt, J=8.3, 5.4 Hz), 0.61-0.41 (4H, m)
ESI-MS m/z 451 (MH+)

Example 36 trans-3-amino-1-methyl-3-(4-(3-phenyl-5H-imidazo[1,2-c]pyrido[4,3-e][1,3]oxazin-2-yl)phenyl)cyclobutanol Using the product of Reference Example 48 and in the same manner as in Example 2, the title compound was obtained as a colorless solid.
$^1$H-NMR (CDCl$_3$) δ: 8.45-8.45 (1H, m), 8.42 (1H, dd, J=4.9, 1.0 Hz), 7.91 (1H, dd, J=4.9, 0.7 Hz), 7.54-7.47 (5H, m), 7.38-7.34 (2H, m), 7.27-7.23 (2H, m), 5.74 (2H, s), 2.64-2.59 (2H, m), 2.39-2.32 (2H, m), 1.63 (3H, s)
ESI-MS m/z 425 (MH+)

Example 37

1-(4-(3-phenyl-5H-imidazo[1,2-c]pyrido[4,3-e][1,3]oxazin-2-yl)phenyl)cyclobutanamine Using the product of Reference Example 48 and in the same manner as in Example 2, but using the product of Reference Example 56(4) in place of the product of Reference Example 58(4), the title compound was obtained as a colorless solid.
$^1$H-NMR (CDCl$_3$) δ: 8.47 (1H, d, J=0.6 Hz), 8.45 (1H, d, J=5.1 Hz), 7.92 (1H, dd, J=5.1, 0.6 Hz), 7.56-7.47 (5H, m), 7.40-7.36 (2H, m), 7.31 (2H, d, J=8.5 Hz), 5.75 (2H, s), 2.57-2.49 (2H, m), 2.18-2.00 (3H, m), 1.79-1.70 (1H, m)
ESI-MS m/z 395 (MH+)

Example 38 trans-3-amino-1-cyclopropyl-3-(4-(3-phenyl-5H-imidazo[1,2-c]pyrido[3,2-e][1,3]oxazin-2-yl)phenyl)cyclobutanol Using the product of Reference Example 49 and in the same manner as in Example 1, the title compound was obtained as a colorless solid.
$^1$H-NMR (CDCl$_3$) δ: 8.40 (1H, dd, J=7.6, 2.0 Hz), 8.26 (1H, dd, J=5.0, 2.0 Hz), 7.56-7.45 (5H, m), 7.39-7.32 (4H, m), 7.20 (1H, dd, J=7.6, 5.0 Hz), 5.85 (2H, s), 2.63-2.57 (2H, m), 2.32-2.26 (2H, m), 1.33 (1H, tt, J=8.3, 5.4 Hz), 0.59-0.53 (2H, m), 0.48-0.42 (2H, m).
ESI-MS m/z 451 (MH+)

Example 39 trans-3-amino-1-methyl-3-(4-(3-phenyl-5H-imidazo[1,2-c]pyrido[3,2-e][1,3]oxazin-2-yl)phenyl)cyclobutanol Using the product of Reference Example 49 and in the same manner as in Example 2, the title compound was obtained as a colorless solid.
$^1$H-NMR (DMSO-D$_6$) δ: 8.30 (1H, dd, J=7.3, 2.0 Hz), 8.26 (1H, dd, J=4.9, 2.0 Hz), 7.56-7.49 (3H, m), 7.45-7.39 (4H, m), 7.33-7.28 (3H, m), 5.96 (2H, s), 4.74 (1H, s), 2.39-2.33 (2H, m), 2.18-2.13 (2H, m), 1.48 (3H, s)
ESI-MS m/z 425 (MH+)

Example 40

1-(4-(3-phenyl-5H-imidazo[1,2-c]pyrido[3,2-e][1,3]oxazin-2-yl)phenyl)cyclobutanamine Using the product of Reference Example 49 and in the same manner as in Example 2, but using the product of Reference Example 56(4) in place of the product of Reference Example 58(4), the title compound was obtained as a colorless solid.
$^1$H-NMR (CDCl$_3$) δ: 8.41 (1H, dd, J=7.6, 2.0 Hz), 8.27 (1H, dd, J=4.9, 2.0 Hz), 7.55-7.45 (5H, m), 7.40-7.36 (2H, m), 7.33-7.29 (2H, m), 7.20 (1H, dd, J=7.6, 4.9 Hz), 5.86 (2H, s), 2.58-2.48 (2H, m), 2.18-1.99 (4H, m), 1.79-1.69 (1H, m)
ESI-MS m/z 395 (MH+)

Example 41 trans-3-amino-1-cyclopropyl-3-(4-(3-phenyl-5H-imidazo[1,2-c]pyrazino[2,3-e][1,3]oxazin-2-yl)phenyl)cyclobutanol Using the product of Reference Example 50 and in the same manner as in Example 1, the title compound was obtained as a light-yellow solid.
$^1$H-NMR (CDCl$_3$) δ: 8.46 (1H, d, J=2.8 Hz), 8.19 (1H, d, J=2.8 Hz), 7.65 (2H, d, J=8.4 Hz), 7.53-7.50 (3H, m), 7.42-7.40 (2H, m), 7.32 (2H, d, J=8.4 Hz), 5.92 (2H, s), 2.62-2.58 (2H, m), 2.31-2.28 (2H, m), 1.38-1.30 (1H, m), 0.58-0.54 (2H, m), 0.47-0.43 (2H, m).
ESI-MS m/z 452 (MH+)

Example 42 trans-3-amino-1-methyl-3-(4-(3-phenyl-5H-imidazo[1,2-c]pyrazo[3,2-e][1,3]oxazin-2-yl)phenyl)cyclobutanol Using the product of Reference Example 50 and in the same manner as in Example 2, the title compound was obtained as a light-yellow solid.
$^1$H-NMR (CDCl$_3$) δ: 8.46 (1H, d, J=2.8 Hz), 8.19 (1H, d, J=2.8 Hz), 7.64 (2H, d, J=8.4 Hz), 7.54-7.52 (3H, m), 7.42-7.40 (2H, m), 7.23 (2H, d, J=8.4 Hz), 5.92 (2H, s), 2.63-2.60 (2H, m), 2.37-2.34 (2H, m), 1.64 (3H, s)
ESI-MS m/z 426 (MH+)

Example 43 trans-3-amino-1-ethyl-3-(4-(3-phenyl-5H-imidazo[1,2-c]pyrazo[3,2-e][1,3]oxazin-2-yl)phenyl)cyclobutanol Using the product of Reference Example 50 and in the same manner as in Example 2, but using the product of Reference Example 59 in place of the product of Reference Example 58(4), the title compound was obtained as a colorless solid.
$^1$H-NMR (CDCl$_3$) δ: 8.47 (1H, d, J=2.4 Hz), 8.20 (1H, d, J=2.4 Hz), 7.65 (2H, d, J=8.4 Hz), 7.54-7.52 (3H, m), 7.43-7.40 (2H, m), 7.30-7.23 (2H, m), 5.92 (2H, s), 2.57-2.54 (2H, m), 2.37-2.34 (2H, m), 1.91 (2H, q, J=7.6 Hz), 0.97 (3H, t, J=7.6 Hz).
ESI-MS m/z 440 (MH+)

Example 44 trans-3-amino-3-(4-(9-(hydroxymethyl)-3-phenyl-5H-benzo[e]imidazo[1,2-c][1,3]oxazin-2-yl)phenyl)-1-methylcyclobutanol Using the product of Reference Example 24 and in the same manner as in Example 2, the title compound was obtained as a colorless solid.

¹H-NMR (CDCl₃) δ: 8.10 (1H, d, J=1.7 Hz), 7.56-7.44 (5H, m), 7.38-7.23 (5H, m), 7.06 (1H, d, J=8.0 Hz), 5.66 (2H, s), 4.72 (2H, s), 2.65-2.60 (2H, m), 2.39-2.33 (2H, m), 1.63 (3H, s).
ESI-MS m/z 454 (MH+)

Example 45 trans-3-amino-3-(4-(8-(hydroxymethyl)-3-phenyl-5H-benzo[e]imidazo[1,2-c][1,3]oxazin-2-yl)phenyl)-1-methylcyclobutanol Using the product of Reference Example 52 and in the same manner as in Example 2, the title compound was obtained as a colorless solid.
¹H-NMR (CDCl₃) δ: 8.06 (1H, d, J=7.8 Hz), 7.54 (2H, d, J=8.3 Hz), 7.50-7.42 (3H, m), 7.38-7.34 (2H, m), 7.24 (2H, d, J=8.3 Hz), 7.17 (1H, dd, J=7.8, 1.5 Hz), 7.10 (1H, d, J=1.5 Hz), 5.66 (2H, s), 4.72 (2H, s), 3.49 (1H, s), 2.65-2.60 (2H, m), 2.39-2.33 (2H, m), 1.63 (3H, s).
ESI-MS m/z 454 (MH+)

Example 46

2-(4-(trans-1-amino-3-hydroxy-3-methylcyclobutyl)phenyl)-3-phenyl-5H-benzo[e]imidazo[1,2-c][1,3]oxazine-9-carbonitrile Using the product of Reference Example 25 and in the same manner as in Example 2, the title compound was obtained as a colorless solid.
¹H-NMR (DMSO-D₆) δ: 8.28 (1H, d, J=2.0 Hz), 7.85 (1H, dd, J=8.5, 2.0 Hz), 7.57-7.29 (10H, m), 5.94 (2H, s), 2.39-2.32 (2H, m), 2.17-2.11 (2H, m), 1.50 (3H, s).
ESI-MS m/z 449 (MH+)

Example 47

2-(4-(trans-1-amino-3-hydroxy-3-methylcyclobutyl)phenyl)-3-phenyl-5H-benzo[e]imidazo[1,2-c][1,3]oxazine-8-carbonitrile Using the product of Reference Example 53 and in the same manner as in Example 2, the title compound was obtained as a colorless solid.
¹H-NMR (DMSO-D₆) δ: 8.03 (1H, d, J=8.0 Hz), 7.72 (1H, d, J=1.5 Hz), 7.66 (1H, dd, J=8.0, 1.5 Hz), 7.55-7.49 (3H, m), 7.45-7.38 (4H, m), 7.30 (2H, d, J=8.5 Hz), 5.90 (2H, s), 2.36-2.30 (2H, m), 2.15-2.10 (2H, m), 1.48 (3H, s).
ESI-MS m/z 449 (MH+)

Example 48 trans-3-amino-1-methyl-3-(4-(3-phenyl-9-(1H-pyrazol-5-yl)-5H-benzo[e]imidazo[1,2-c][1,3]oxazin-2-yl)phenyl)cyclobutanol Using the product of Reference Example 26 and in the same manner as in Example 2, the title compound was obtained as a colorless solid.
¹H-NMR (CDCl₃) δ: 8.47 (1H, d, J=2.2 Hz), 7.77 (1H, dd, J=8.5, 2.2 Hz), 7.62 (1H, d, J=2.4 Hz), 7.55 (2H, d, J=8.5 Hz), 7.50-7.43 (3H, m), 7.39-7.35 (2H, m), 7.27-7.23 (2H, m), 7.12 (1H, d, J=8.5 Hz), 6.70 (1H, d, J=2.2 Hz), 5.70 (2H, s), 2.66-2.60 (2H, m), 2.41-2.35 (2H, m), 1.62 (3H, s).
ESI-MS m/z 490 (MH+)

Example 49

2-(4-(trans-1-amino-3-hydroxy-3-methylcyclobutyl)phenyl)-3-phenyl-5H-benzo[e]imidazo[1,2-c][1,3]oxazin-8-carbonitrile Using the product of Reference Example 27 and in the same manner as in Example 2, the title compound was obtained as a colorless solid.
¹H-NMR (CDCl₃) δ: 8.23 (1H, d, J=2.2 Hz), 7.94-7.93 (2H, m), 7.56 (2H, d, J=8.3 Hz), 7.50-7.44 (4H, m), 7.39-7.36 (2H, m), 7.28-7.24 (2H, m), 7.09 (1H, d, J=8.5 Hz), 5.69 (2H, s), 2.66-2.60 (2H, m), 2.40-2.34 (2H, m), 1.64 (3H, s).
ESI-MS m/z 490 (MH+)

Example 50 trans-3-amino-1-methyl-3-(4-(9-methyl-3-phenyl-5H-imidazo[1,2-c]pyrido[2,3-e][1,3]oxazin-2-yl)phenyl)cyclobutanol Using the product of Reference Example 54 and in the same manner as in Example 2, the title compound was obtained as a colorless solid.
¹H-NMR (CDCl₃) δ: 7.65 (2H, d, J=8.0 Hz), 7.52-7.48 (3H, m), 7.40-7.38 (2H, m), 7.28-7.26 (1H, m), 7.21 (2H, d, J=8.0 Hz), 7.10 (1H, d, J=8.4 Hz), 5.67 (2H, s), 2.65 (3H, s), 2.63-2.60 (2H, m), 2.38-2.34 (2H, m), 1.64 (3H, s).
ESI-MS m/z 439 (MH+)

Example 51 trans-3-amino-3-(4-(9-methoxy-3-phenyl-5H-imidazo[1,2-c]pyrido[2,3-e][1,3]oxazin-2-yl)phenyl)-1-methylcyclobutanol Using the product of Reference Example 55 and in the same manner as in Example 2, the title compound was obtained as a colorless solid.
¹H-NMR (CDCl₃) δ: 7.60 (2H, d, J=8.0 Hz), 7.52-7.46 (3H, m), 7.38-7.36 (2H, m), 7.32 (1H, d, J=8.8 Hz), 7.22 (2H, d, J=8.0 Hz), 6.72 (1H, d, J=8.8 Hz), 5.65 (2H, s), 4.11 (3H, s), 2.63-2.60 (2H, m), 2.38-2.34 (2H, m), 1.64 (3H, s).
ESI-MS m/z 455 (MH+)

Example 52

Example 52(1)

methyl 2-(4-(trans-1-(tert-butoxycarbonylamine)-3-hydroxy-3-methylcyclobutyl)phenyl)-3-phenyl-5H-benzo[e]imidazo[1,2-c][1,3]oxazine-9-carboxylate Tert-butyl trans-3-hydroxy-3-methyl-1-(4-(4,4,5,5-tetramethyl-1,3,2-dioxaborolan-2-yl)phenyl)cyclobutylcarbamate (125 mg) and cesium carbonate (194 mg) were added to a solution of the product (148 mg) of Reference Example 23(4) in 1,4-dioxane (2.4 mL) and water (0.4 mL), and the mixture was placed in a nitrogen atmosphere. Pd(PPh3)4 (27.5 mg) was then added thereto, and the mixture was stirred at 100° C. for 2 hours. The reaction mixture was cooled to room temperature, diluted with ethyl acetate, dried over anhydrous sodium sulfate, and concentrated under reduced pressure. The obtained residue was purified by silica gel chromatography (hexane:ethyl acetate) to give the desired product (191 mg, yield: 71%) as a colorless solid.

$^1$H-NMR (CDCl$_3$) δ: 8.79 (1H, d, J=2.2 Hz), 8.02 (1H, dd, J=8.5, 2.2 Hz), 7.57-7.19 (7H, m), 7.11 (1H, d, J=8.5 Hz), 6.75 (2H, d, J=8.8 Hz), 5.73 (2H, s), 5.23-5.13 (1H, br m), 3.94 (4H, s), 2.79-2.60 (4H, m), 1.56 (3H, s), 1.44-1.29 (9H, br m).

ESI-MS m/z 582 (MH+)

Example 52(2)

2-(4-(trans-1-(tert-butoxycarbonylamino)-3-hydroxy-3-methylcyclobutyl)phenyl)-3-phenyl-5H-benzo[e]imidazo[1,2-c][1,3]oxazine-9-carboxylic acid A 2M aqueous potassium hydroxide solution (0.6 mL) was added to a methanol (2.5 mL) solution of the product (140 mg) of Example 52(1), and the mixture was stirred at room temperature for 5 hours. A 0.5 M aqueous potassium hydrogen sulfate solution was added to the reaction mixture and extracted with chloroform. The combined organic layer was washed with saturated sodium chloride, dried over anhydrous sodium sulfate, and concentrated under reduced pressure to give the desired product (120 mg, yield: 88%) as a colorless solid.

$^1$H-NMR (CDCl$_3$) δ: 9.14 (1H, d, J=1.8 Hz), 8.03 (1H, dd, J=8.4, 1.8 Hz), 7.60 (2H, d, J=8.3 Hz), 7.47-7.06 (7H, m), 6.71 (1H, d, J=8.4 Hz), 5.71 (2H, s), 5.11-4.89 (1H, br m), 2.76-2.45 (4H, m), 1.53 (3H, s), 1.45-1.24 (9H, br m).

ESI-MS m/z 568 (MH+)

Example 52(3)

2-(4-(trans-1-amino-3-hydroxy-3-methylcyclobutyl)phenyl)-N-methyl-3-phenyl-5H-benzo[e]imidazo[1,2-c][1,3]oxazine-9-carboxamide Methylamine hydrochloride (5.0 mg), triethylamine (0.025 mL), WSC hydrochloride (13.5 mg), and HOBt (10.8 mg) were added to a DMF (0.5 mL) solution of the product (20 mg) of Example 52(2), and the mixture was stirred at room temperature for 2 hours and stirred at 90° C. for 1 hour. The reaction mixture was cooled to room temperature, diluted with water, and extracted with ethyl acetate. The combined organic layer was dried over anhydrous sodium sulfate and concentrated under reduced pressure. The obtained residue was purified by silica gel chromatography (hexane:ethyl acetate) to give the corresponding compound. The obtained compound was used for the next reaction without further purification. Trifluoroacetic acid (0.5 mL) was added to a chloroform (1.0 mL) solution of the obtained compound, and the mixture was stirred at room temperature for 1 hour. The reaction mixture was concentrated under reduced pressure, and the obtained residue was purified by silica gel chromatography (chloroform: methanol) to give the title compound (14.8 mg, yield: 87%) as a colorless solid.

$^1$H-NMR (CDCl$_3$) δ: 8.37 (1H, d, J=2.2 Hz), 7.91 (1H, dd, J=8.5, 2.2 Hz), 7.51-7.44 (5H, m), 7.37-7.32 (2H, m), 7.23-7.18 (2H, m), 7.11 (1H, d, J=8.5 Hz), 6.67-6.57 (1H, br m), 5.70 (2H, s), 2.99-2.94 (3H, m), 2.63-2.56 (2H, m), 2.37-2.30 (2H, m), 1.62 (3H, s).

ESI-MS m/z 481 (MH+)

Example 53

2-(4-(trans-1-amino-3-hydroxy-3-methylcyclobutyl)phenyl)-3-phenyl-5H-benzo[e]imidazo[1,2-c][1,3]oxazine-9-carboxamide In the same manner as in Example 52 but using 28% aqueous ammonia in place of the methylamine hydrochloride of Example 52(3), the title compound was obtained as a colorless solid.

$^1$H-NMR (CDCl$_3$) δ: 8.45 (1H, d, J=2.0 Hz), 7.96 (1H, dd, J=8.5, 2.0 Hz), 7.55-7.44 (5H, m), 7.39-7.34 (2H, m), 7.28-7.24 (2H, m), 7.16 (1H, d, J=8.5 Hz), 5.74 (2H, s), 2.66-2.60 (2H, m), 2.39-2.33 (2H, m), 1.63 (3H, s).

ESI-MS m/z 467 (MH+)

Example 54

2-(4-(trans-1-amino-3-hydroxy-3-methylcyclobutyl)phenyl)-N,N-dimethyl-3-phenyl-5H-benzo[e]imidazo[1,2-c][1,3]oxazine-9-carboxamide In the same manner as in Example 52, but using dimethylamine hydrochloride in place of the methylamine hydrochloride of Example 52(3), the title compound was obtained as a colorless solid.

$^1$H-NMR (CDCl$_3$) δ: 8.14 (1H, d, J=2.2 Hz), 7.55-7.42 (6H, m), 7.38-7.34 (2H, m), 7.23 (2H, d, J=8.5 Hz), 7.10 (1H, d, J=8.3 Hz), 5.69 (2H, s), 3.16-3.02 (6H, m), 2.64-2.58 (2H, m), 2.38-2.32 (2H, m), 1.62 (3H, s).

ESI-MS m/z 495 (MH+)

Example 55

2-(4-(trans-1-amino-3-hydroxy-3-methylcyclobutyl)phenyl)-N-ethyl-3-phenyl-5H-benzo[e]imidazo[1,2-c][1,3]oxazine-9-carboxamide In the same manner as in Example 52 but using ethylamine hydrochloride in place of the methylamine hydrochloride of Example 52(3), the title compound was obtained as a colorless solid.

$^1$H-NMR (CDCl$_3$) δ: 8.38 (1H, d, J=2.2 Hz), 7.93 (1H, dd, J=8.5, 2.2 Hz), 7.52-7.44 (5H, m), 7.38-7.33 (2H, m), 7.25-7.21 (2H, m), 7.13 (1H, d, J=8.5 Hz), 6.60-6.50 (1H, m), 5.71 (2H, s), 3.54-3.45 (2H, m), 2.64-2.58 (2H, m), 2.38-2.32 (2H, m), 1.62 (3H, s), 1.27 (3H, t, J=7.3 Hz).

ESI-MS m/z 495 (MH+)

Example 56

2-(4-(trans-1-amino-3-hydroxy-3-methylcyclobutyl)phenyl)-N-methyl-3-phenyl-5H-benzo[e]imidazo[1,2-c][1,3]oxazine-8-carboxamide In the same manner as in Example 52, but reacting the product of Reference Example 51 in place of the product of Reference Example 23(4), the title compound was obtained as a colorless solid.

$^1$H-NMR (CDCl$_3$) δ: 8.12 (1H, d, J=8.0 Hz), 7.56-7.45 (7H, m), 7.39-7.35 (2H, m), 7.28-7.23 (2H, m), 6.18-6.11 (1H, m), 5.71 (2H, s), 3.04 (3H, d, J=4.9 Hz), 2.65-2.60 (2H, m), 2.39-2.34 (2H, m), 1.64 (3H, s).

ESI-MS m/z 481 (MH+)

Example 57

2-(4-(trans-1-amino-3-hydroxy-3-methylcyclobutyl)phenyl)-N,N-dimethyl-3-phenyl-5H-benzo[e]imidazo[1,2-c][1,3]oxazine-8-carboxamide In the same manner as in Example 52, but using dimethylamine hydrochloride in place of the methylamine hydrochloride of Example 52(3) and also reacting the product of Reference Example 51 in place of the product of Reference Example 23(4), the title compound was obtained as a colorless solid.

$^1$H-NMR (CDCl$_3$) δ: 8.10 (1H, d, J=8.0 Hz), 7.56-7.44 (5H, m), 7.38-7.35 (2H, m), 7.28-7.21 (3H, m), 7.16 (1H, d, J=1.5 Hz), 5.69 (2H, s), 3.13 (3H, s), 3.03 (3H, s), 2.65-2.60 (2H, m), 2.40-2.35 (2H, m), 1.64 (3H, s).

ESI-MS m/z 495 (MH+)

Example 58

2-(4-(trans-1-amino-3-hydroxy-3-methylcyclobutyl)phenyl)-N-(2-hydroxyethyl)-3-phenyl-5H-benzo[e]imidazo[1,2-c][1,3]oxazine-8-carboxamide In the same manner as in Example 52, but using 2-aminoethanol in place of the methylamine hydrochloride of Example 52(3), and also reacting the product of Reference Example 51 in place of the product of Reference Example 23(4), the title compound was obtained as a colorless solid.

$^1$H-NMR (CDCl$_3$—CD$_3$OD) δ: 8.09 (1H, d, J=8.0 Hz), 7.62-7.57 (2H, m), 7.52-7.44 (5H, m), 7.36-7.31 (2H, m), 7.29-7.25 (2H, m), 5.70 (2H, s), 3.81-3.75 (2H, m), 3.61-3.54 (2H, m), 2.69-2.64 (2H, m), 2.43-2.37 (2H, m), 1.60 (3H, s).

ESI-MS m/z 511 (MH+)

Example 59

2-(4-(trans-1-amino-3-hydroxy-3-methylcyclobutyl)phenyl)-N-ethoxy-3-phenyl-5H-benzo[e]imidazo[1,2-c][1,3]oxazine-8-carboxamide In the same manner as in Example 52, but using O-ethylhydroxylamine hydrochloride in place of the methylamine hydrochloride of Example 52(3), and also reacting the product of Reference Example 51 in place of the product of Reference Example 23 (4), the title compound was obtained as a colorless solid.

$^1$H-NMR (CDCl$_3$—CD$_3$OD) δ: 8.04-8.00 (1H, m), 7.52-7.43 (7H, m), 7.33-7.23 (4H, m), 5.66 (2H, s), 4.08 (2H, q, J=7.1 Hz), 2.69-2.63 (2H, m), 2.42-2.35 (2H, m), 1.59 (3H, s), 1.34 (3H, t, J=7.1 Hz).

ESI-MS m/z 511 (MH+)

Example 60

2-(4-(trans-1-amino-3-hydroxy-3-methylcyclobutyl)phenyl)-N-(2-hydroxyethyl)-3-phenyl-5H-benzo[e]imidazo[1,2-c][1,3]oxazine-9-carboxamide In the same manner as in Example 52, but using 2-aminoethanol in place of the methylamine hydrochloride of Example 52(3), the title compound was obtained as a colorless solid.

$^1$H-NMR (CDCl$_3$—CD$_3$OD) δ: 8.35 (1H, d, J=2.0 Hz), 7.99-7.94 (1H, m), 7.50-7.43 (5H, m), 7.35-7.26 (4H, m), 7.15 (1H, d, J=8.5 Hz), 5.72 (2H, s), 3.83-3.78 (2H, m), 3.63-3.58 (2H, m), 2.70-2.65 (2H, m), 2.43-2.37 (2H, m), 1.60 (3H, s).

ESI-MS m/z 511 (MH+)

Example 61

2-(4-(trans-1-amino-3-hydroxy-3-methylcyclobutyl)phenyl)-N-ethoxy-3-phenyl-5H-benzo[e]imidazo[1,2-c][1,3]oxazine-9-carboxamide In the same manner as in Example 52, but using O-ethylhydroxylamine hydrochloride in place of the methylamine hydrochloride of Example 52(3), the title compound was obtained as a colorless solid.

$^1$H-NMR (CDCl$_3$—CD$_3$OD) δ: 8.19 (1H, d, J=2.0 Hz), 7.96 (1H, dd, J=8.8, 2.0 Hz), 7.50-7.42 (5H, m), 7.35-7.27 (4H, m), 7.17 (1H, d, J=8.8 Hz), 5.72 (2H, s), 4.11 (2H, q, J=7.1 Hz), 2.71-2.65 (2H, m), 2.44-2.37 (2H, m), 1.61 (3H, s), 1.38 (3H, t, J=7.1 Hz).

ESI-MS m/z 511 (MH+)

Example 62

2-(4-(trans-1-amino-3-hydroxy-3-methylcyclobutyl)phenyl)-3-phenyl-5H-benzo[e]imidazo[1,2-c][1,3]oxazine-8-carboxamide In the same manner as in Example 52, but using 28% aqueous ammonia in place of the methylamine hydrochloride of Example 52(3) and also reacting the product of Reference Example 51 in place of the product of Reference Example 23(4), the title compound was obtained as a colorless solid.

$^1$H-NMR (CDCl$_3$) δ: 8.05 (1H, d, J=8.5 Hz), 7.55-7.42 (7H, m), 7.34-7.29 (2H, m), 7.22 (2H, d, J=8.3 Hz), 6.62-6.35 (1H, br m), 6.14-5.82 (1H, br m), 5.65 (2H, s), 2.64-2.58 (2H, m), 2.36-2.31 (2H, m), 1.61 (3H, s)

ESI-MS m/z 467 (MH+)

Example 63

2-(4-(trans-1-amino-3-hydroxy-3-methylcyclobutyl)phenyl)-3-phenyl-5H-benzo[e]imidazo[1,2-c][1,3]oxazine-9-carboxylic acid hydrochloride An ethyl acetate solution (0.5 mL) of 4M hydrochloric acid was added to an ethyl acetate (1.0 mL) solution of the product (19.5 mg) of Example 52(2), and the mixture was stirred at room temperature for 1 hour. The reaction mixture was filtered, and the residue was washed with ethyl acetate to give the title compound (6.0 mg, yield: 35%) as a colorless solid.

$^1$H-NMR (DMSO-D$_6$) δ: 8.69-8.59 (3H, br m), 8.58 (1H, d, J=2.2 Hz), 8.00 (1H, dd, J=8.5, 2.2 Hz), 7.59-7.47 (9H, m), 7.31 (1H, d, J=8.5 Hz), 5.94 (2H, s), 2.71-2.59 (4H, m), 1.42 (3H, s).

ESI-MS m/z 468 (MH+)

Example 64

2-(4-(trans-1-amino-3-hydroxy-3-methylcyclobutyl)phenyl)-3-phenyl-5H-benzo[e]imidazo[1,2-c][1,3]oxazine-8-carboxylic acid hydrochloride In the same manner as in Example 52, but using the product of Reference Example 51 in place of the product of Reference Example 23(4), 2-(4-(trans-1-(tert-butoxycarbonylamino)-3-hydroxy-3-methylcyclobutyl)phenyl)-3-phenyl-5H-benzo[e]imidazo[1,2-c][1,3]oxazine-8-carboxylic acid was obtained. Subsequently, in the same manner as in Example 63, the title compound was obtained as a colorless solid.

$^1$H-NMR (DMSO-D$_6$) δ: 8.68-8.57 (3H, br m), 8.12 (1H, d, J=8.0 Hz), 7.82 (1H, dd, J=8.0, 1.5 Hz), 7.62 (1H, d, J=1.5 Hz), 7.58-7.45 (9H, m), 5.90 (2H, s), 2.69-2.58 (4H, m), 1.41 (3H, s).

ESI-MS m/z 468 (MH+)

The list of the compounds is shown in Table 3 below.

TABLE 3

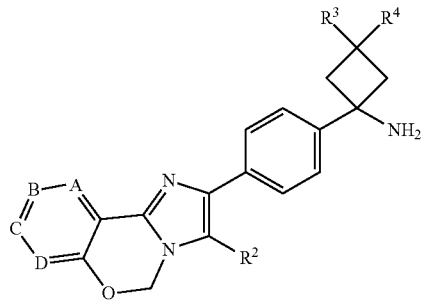

I

| No. | A | B | C | D | R2 | R3 | R4 |
|---|---|---|---|---|---|---|---|
| 1 | C—F | CH | CH | CH | phenyl | cyclopropyl | OH |
| 2 | C—F | CH | CH | CH | phenyl | Me | OH |
| 3 | C—F | CH | CH | CH | phenyl | H | H |
| 4 | C—F | CH | CH | CH | thiophen-3-yl | cyclopropyl | OH |
| 5 | C—F | CH | CH | CH | pyridin-4-yl | cyclopropyl | OH |
| 6 | C—F | CH | CH | CH | thiophen-3-yl | Me | OH |
| 7 | C—F | CH | CH | CH | pyridin-4-yl | Me | OH |
| 8 | CH | C—F | CH | CH | phenyl | Me | OH |
| 9 | CH | CH | C—F | CH | phenyl | Me | OH |

TABLE 3-continued
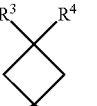
I
| No. | A | B | C | D | R2 | R3 | R4 |
|---|---|---|---|---|---|---|---|
| 10 | CH | CH | CH | C—F |  | 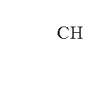 | OH |
| 11 | CH | CH | CH | CH |  |  | OH |
| 12 | CH | CH | CH | CH | 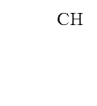 | Me | OH |
| 13 | CH | CH | CH | CH |  | H | H |
| 14 | CH | CH | CH | CH |  | H | H |
| 15 | CH | CH | CH | CH |  | H | H |
| 16 | C—OMe | CH | CH | CH |  |  | OH |
| 17 | CH | C—OMe | CH | CH |  | 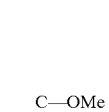 | OH |
| 18 | CH | CH | C—OMe | CH |  |  | OH |
| 19 | CH | CH | CH | C—OMe |  |  | OH |
| 20 | CH | C—OMe | CH | CH |  | Me | OH |

TABLE 3-continued
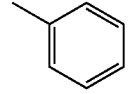
I
| No. | A | B | C | D | R2 | R3 | R4 |
|---|---|---|---|---|---|---|---|
| 21 | CH | CH | C—OMe | CH | 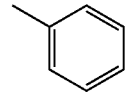 | Me | OH |
| 22 | C—Cl | CH | CH | CH |  | 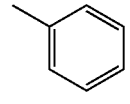 | OH |
| 23 | C—OEt | CH | CH | CH |  | 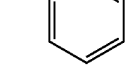 | OH |
| 24 | C—OEt | CH | CH | CH | 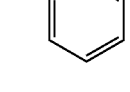 | Me | OH |
| 25 | C—OMe | CH | C—OMe | CH |  | 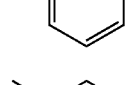 | OH |
| 26 | CH | CH | CH | C—Me |  | 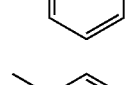 | OH |
| 27 | N | CH | CH | CH |  | 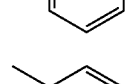 | OH |
| 28 | N | CH | CH | CH | 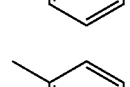 | Me | OH |
| 29 | N | CH | CH | CH | 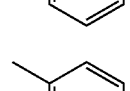 | H | H |
| 30 | N | CH | CH | CH | 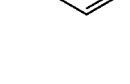 | Et | OH |
| 31 | CH | N | CH | CH |  | 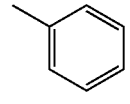 | OH |

TABLE 3-continued
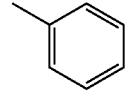
I
| No. | A | B | C | D | R2 | R3 | R4 |
|---|---|---|---|---|---|---|---|
| 32 | CH | N | CH | CH | 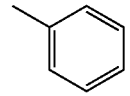 | Me | OH |
| 33 | CH | N | CH | CH | 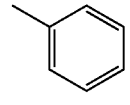 | H | H |
| 34 | CH | N | CH | CH | 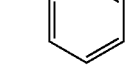 | Et | OH |
| 35 | CH | CH | N | CH |  | 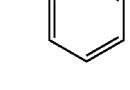 | OH |
| 36 | CH | CH | N | CH | 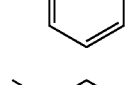 | Me | OH |
| 37 | CH | CH | N | CH | 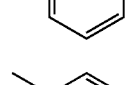 | H | H |
| 38 | CH | CH | CH | N |  | 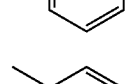 | OH |
| 39 | CH | CH | CH | N | 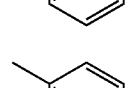 | Me | OH |
| 40 | CH | CH | CH | N | 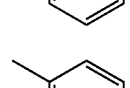 | H | H |
| 41 | N | CH | CH | N |  | 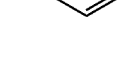 | OH |
| 42 | N | CH | CH | N | | Me | OH |

TABLE 3-continued
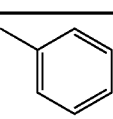
| No. | A | B | C | D | R2 | R3 | R4 |
|---|---|---|---|---|---|---|---|
| 43 | N | CH | CH | N | 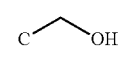 | Et | OH |
| 44 | CH | 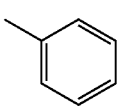 C—CH₂OH | CH | CH | 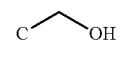 | Me | OH |
| 45 | CH | CH | 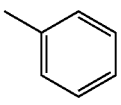 C—CH₂OH | CH | 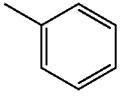 | Me | OH |
| 46 | CH | C—CN | CH | CH | 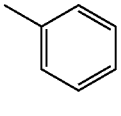 | Me | OH |
| 47 | CH | CH | C—CN | CH | 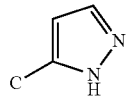 | Me | OH |
| 48 | CH | 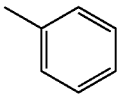 | CH | CH | 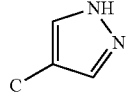 | Me | OH |
| 49 | CH | 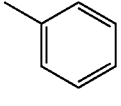 | CH | CH | 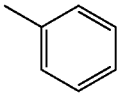 | Me | OH |
| 50 | N | C—Me | CH | CH | 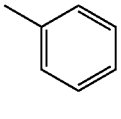 | Me | OH |
| 51 | N | C—OMe | CH | CH | 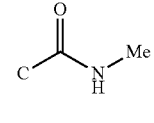 | Me | OH |
| 52 | CH | 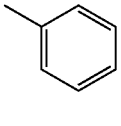 C—C(O)NHMe | CH | CH | 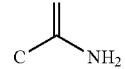 | Me | OH |
| 53 | CH | 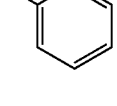 C—C(O)NH₂ | CH | CH | | Me | OH |

TABLE 3-continued

| No. | A | B | C | D | R2 | R3 | R4 |
|---|---|---|---|---|---|---|---|
| 54 | CH | C(=O)NMe₂ | CH | CH | phenyl | Me | OH |
| 55 | CH | C(=O)NHEt | CH | CH | phenyl | Me | OH |
| 56 | CH | CH | C(=O)NHMe | CH | phenyl | Me | OH |
| 57 | CH | CH | C(=O)NMe₂ | CH | phenyl | Me | OH |
| 58 | CH | CH | C(=O)NHCH₂CH₂OH | CH | phenyl | Me | OH |
| 59 | CH | CH | C(=O)NH-O-Et | CH | phenyl | Me | OH |
| 60 | CH | C(=O)NHCH₂CH₂OH | CH | CH | phenyl | Me | OH |
| 61 | CH | C(=O)NH-O-Et | CH | CH | phenyl | Me | OH |
| 62 | CH | CH | C(=O)NH₂ | CH | phenyl | Me | OH |
| 63 | CH | C(=O)OH | CH | CH | phenyl | Me | OH |
| 64 | CH | CH | C(=O)OH | CH | phenyl | Me | OH |

Test Example

In Test Examples below, Compound-I is trans-3-amino-1-methyl-3-(4-(3-phenyl-5H-imidazo[1,2-c]pyrido[3,4-e][1,3]oxazin-2-yl)phenyl)cyclobutanol obtained in Example 32 above, and Compound-II is trans-3-amino-1-cyclopropyl-3-(4-(3-phenyl-5H-imidazo[1,2-c]pyrido[4,3-e][1,3]oxazin-2-yl)phenyl)cyclobutanol obtained in Example 35 above.

Test Example 1

Potentiation of Antitumor Effect of Paclitaxel

Human ovarian cancer A2780 cell line was subcutaneously implanted into the right flank of 7-week-old male BALB/cA Jcl-nu/nu mice. After the implant, the length (mm) and the width (mm) of the tumor were measured, and the tumor volume (TV) was calculated. Thereafter, the mice were divided into groups so that the average TV is equalized in each group. The day of grouping (n=5) is referred to as Day 0. A test liquid for the group receiving only paclitaxel (Wako Pure Chemical Ind. Ltd.) was prepared by diluting paclitaxel with a diluent containing 10% ethyl alcohol/10% Cremophor/80% physiological saline so as to enable administration at a paclitaxel dose of 60 mg/kg/day. Test liquids for the groups receiving only Compound-I were prepared by diluting Compound-I with 0.5% hydroxypropyl methylcellulose (HPMC) so as to enable administration at a Compound-I dose of 8 mg/kg/day, 16 mg/kg/day, and 24 mg/kg/day. Compound-I was administered once a day as oral administration for 14 days from Day 1, and paclitaxel was administered via the tail vein of each mouse at Day 1 and Day 8. The group receiving only either drug was administered a vehicle of 10% ethyl alcohol/10% Cremophor/80% physiological saline, or a vehicle of 0.5% HPMC, instead of paclitaxel or Compound-I. In the groups receiving the two drugs, Compound-I was administered at doses of 8 mg/kg/day, 16 mg/kg/day, and 24 mg/kg/day, and paclitaxel was administered at a dose of 60 mg/kg/day.

As an index of antitumor effect, the TV at Day 15 was measured for each of the drug administration groups, and the relative tumor volume (RTV) relative to Day 1 and T/C (%) were calculated by the following formulas to evaluate the antitumor effect. The effect of the combined administration was evaluated such that when the average RTV value of the combined administration group was statistically significantly smaller than the average RTV value of the single-drug administration group (Welch's Intersection-Union test), the combined administration was determined to be effective. In the figure, the asterisk represents a result having a statistically significant difference compared with the single-drug administration group.

FIG. 1 and Table 10 show the results.

$$TV\ (mm^3) = (length \times width^2)/2$$

$$RTV = (TV\ at\ Day\ 15)/(TV\ at\ Day\ 1)$$

$$T/C(\%) = (\text{average RTV value of the test liquid administration group})/(\text{average RTV value of the control group}) \times 100$$

Further, as an index of toxicity, the body weight was measured over time, and the average body weight change [BWC (%)] until Day 15 relative to Day 1 was calculated by the following formula (n is the body weight measurement day, which is twice a week; the final measurement day is Day 15, which is the final evaluation day).

Figure 2:
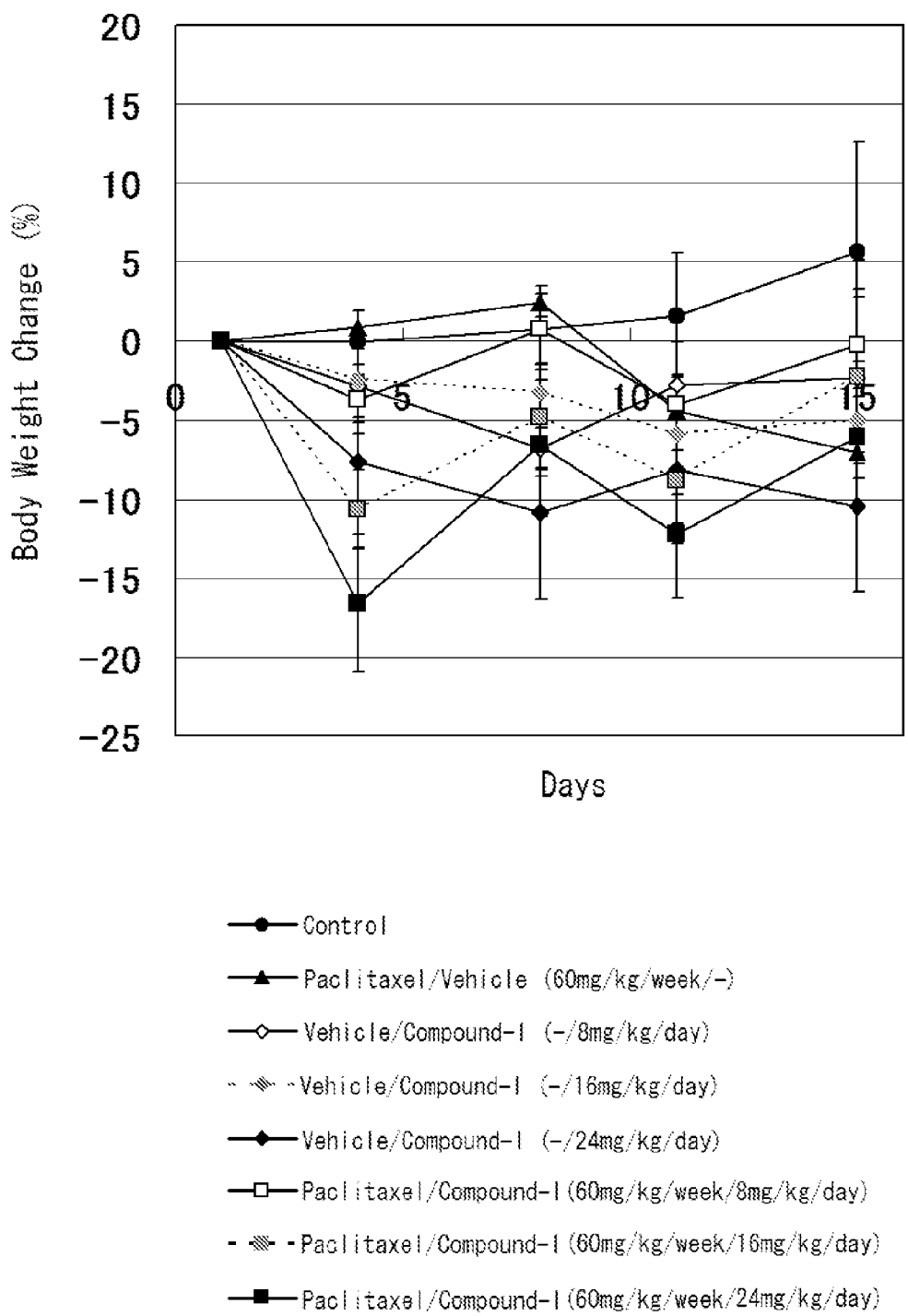
FIG. 2 Body weight changes of nude mice subcutaneously implanted with human ovarian cancer cell line A2780 upon combined use of Compound-I, at 8 mg/kg/day, 16 mg/kg/day, and 24 mg/kg/day, with paclitaxel.

FIG. 2 shows the results.

$$BWC\ (\%) = [(BW\ at\ Day\ n) - (BW\ at\ Day\ 1)]/(BW\ at\ Day\ 1) \times 100$$

TABLE 10

| Group | Dose (mg/kg/day) | Schedule (day) | Route | RTV day 15 Mean ± SD | | T/C (%) |
|---|---|---|---|---|---|---|
| control(Vehicle/Vehicle) | — | 1, 8/1-14 | i.v./p.o. | 25.75 ± 8.00 | | 100 |
| paclitaxel/Vehicle | 60/— | 1, 8/1-14 | i.v./p.o. | 6.96 ± 1.41 | | 27 |
| Vehicle/compound-I | —/8 | 1, 8/1-14 | i.v./p.o. | 23.66 ± 9.16 | | 92 |
| Vehicle/compound-I | —/16 | 1, 8/1-14 | i.v./p.o. | 19.91 ± 1.41 | | 77 |
| Vehicle/compound-I | —/24 | 1, 8/1-14 | i.v./p.o. | 18.94 ± 5.52 | | 74 |
| paclitaxel/compound-I | 60/8 | 1, 8/1-14 | i.v./p.o. | 1.58 ± 1.08 | ‡ | 6 |
| paclitaxel/compound-I | 60/16 | 1, 8/1-14 | i.v./p.o. | 0.73 ± 0.19 | ‡ | 3 |
| paclitaxel/compound-I | 60/24 | 1, 8/1-14 | i.v./p.o. | 0.57 ± 0.17 | ‡ | 2 |

‡ Intersection-Union test:
p < 0.05(vs 8, 16, 24 mg/kg of Compound-I)
p < 0.01(xs 60 mg/kg of paclitaxel)

Test Example 2

Potentiation of Antitumor Effect of Paclitaxel

Human stomach cancer cell line (NCI-N87) was subcutaneously implanted into the right flank of 7-week-old male BALB/cA Jcl-nu/nu mice, and was used in the same manner as in Test Example 1.

A test liquid for the group receiving only paclitaxel (Wako Pure Chemical Ind. Ltd.) was prepared to enable administration at a paclitaxel dose of 60 mg/kg/day. Further, test liquids for the groups receiving only Compound-I were prepared to enable administration at Compound-I doses of 8 mg/kg/day, 16 mg/kg/day, and 24 mg/kg/day. Compound-I was administered once a day as oral administration for 14 days from Day 1, and paclitaxel was administered via the tail vein of each mouse at Day 1 and Day 8. As in Test Example 1, the group receiving only either drug was administered a vehicle, instead of paclitaxel or Compound-I. In the groups receiving the two drugs, Compound-I was administered at doses of 8 mg/kg/day, 16 mg/kg/day, and 24 mg/kg/day, and paclitaxel was administered at a dose of 60 mg/kg/day. The evaluation was performed in the same manner as in Test Example 1. The effect of the combined administration was also statistically determined in the same manner as in Test Example 1. In the figure and the table, the asterisk represents a result having a statistically significant difference compared with the single-drug administration group.

Figure 3:
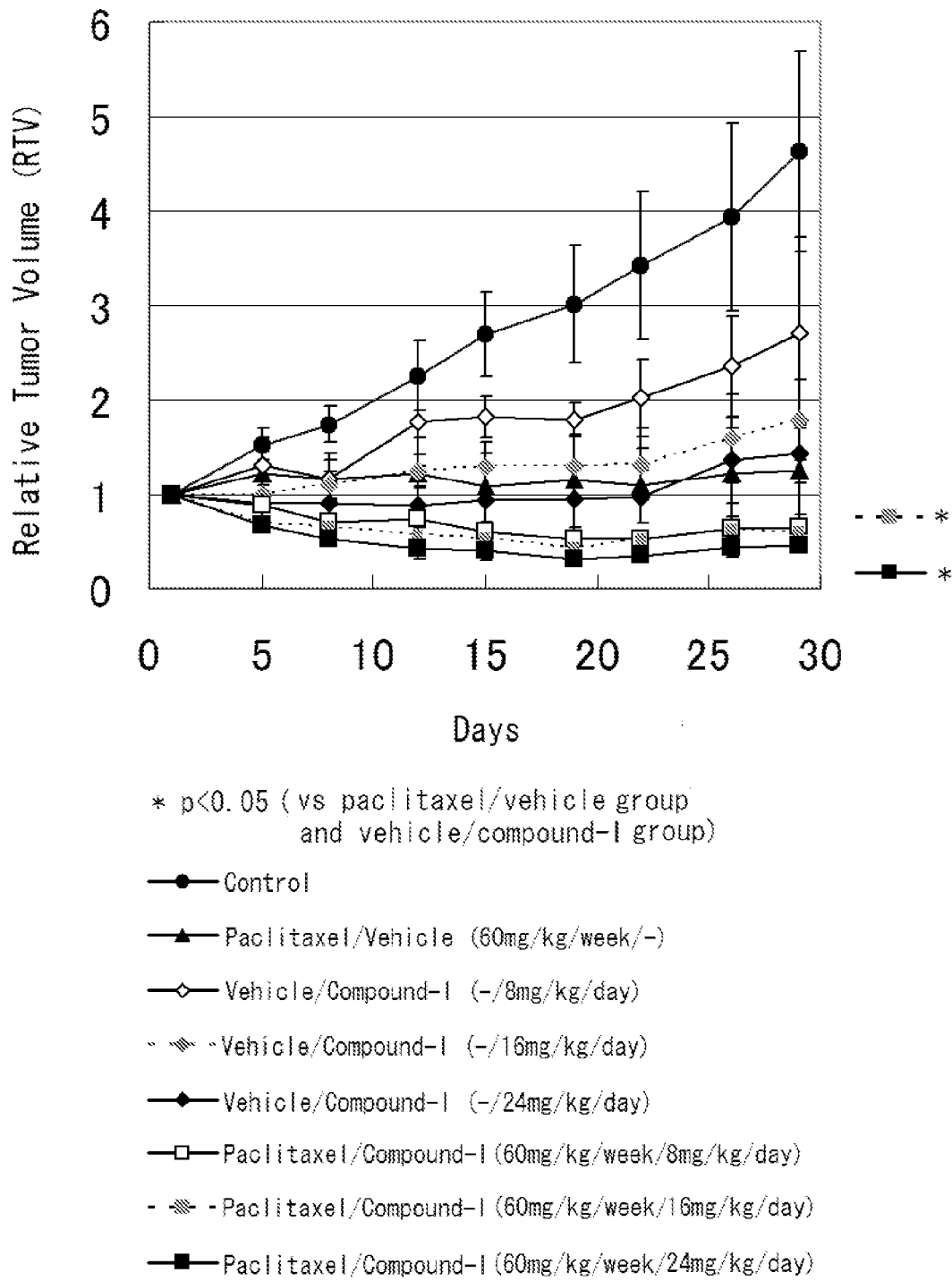
FIG. 3 Effect of combined use of Compound-I, at 8 mg/kg/day, 16 mg/kg/day, and 24 mg/kg/day, with paclitaxel in nude mice subcutaneously implanted with human stomach cancer cell line NCI-N87.

FIG. 3 and Table 11 show the results.

Figure 4:
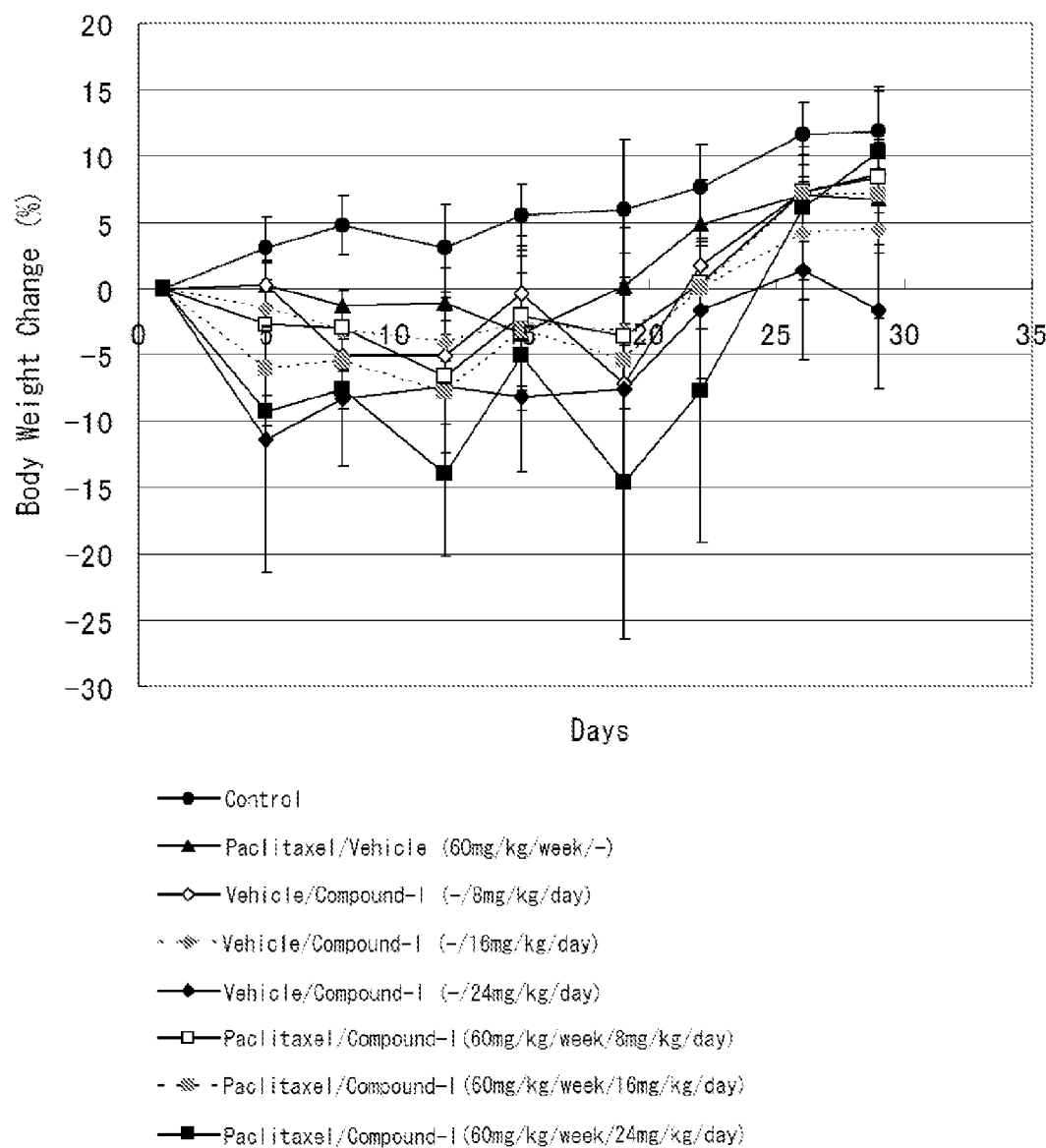
FIG. 4 Body weight changes of nude mice subcutaneously implanted with human stomach cancer cell line NCI-N87 upon combined use of Compound-I, at 8 mg/kg/day, 16 mg/kg/day, and 24 mg/kg/day, with paclitaxel.

Further, the change in the body weight over time was evaluated as an index of toxicity in the same manner as in Test Example 1. FIG. 4 shows the results.

TABLE 11

| Group | Dose (mg/kg/day) | Schedule (day) | Route | RTV day 15 Mean ± SD | | T/C (%) |
|---|---|---|---|---|---|---|
| control(Vehicle/Vehicle) | — | 1, 8/1-14 | 0 | 3.41 ± 0.78 | | 100 |
| paclitaxel/Vehicle | 60/— | 1, 8/1-14 | i.v./p.o. | 1.09 ± 0.40 | | 32 |
| Vehicle/compound-I | —/8 | 1, 8/1-14 | i.v./p.o. | 2.02 ± 0.41 | | 59 |
| Vehicle/compound-I | —/16 | 1, 8/1-14 | i.v./p.o. | 1.32 ± 0.38 | | 39 |
| Vehicle/compound-I | —/24 | 1, 8/1-14 | i.v./p.o. | 0.98 ± 0.28 | | 29 |
| paclitaxel/compound-I | 60/8 | 1, 8/1-14 | i.v./p.o. | 0.52 ± 0.06 | | 15 |
| paclitaxel/compound-I | 60/16 | 1, 8/1-14 | i.v./p.o. | 0.51 ± 0.10 | ‡ | 15 |
| paclitaxel/compound-I | 60/24 | 1, 8/1-14 | i.v./p.o. | 0.36 ± 0.05 | ‡ | 10 |

‡ Intersection-Union test:
$p < 0.05$(vs paclitaxel/vehicle group and vehicle/Compound-I group)

Test Example 3

Potentiation of Antitumor Effect of Carboplatin

Human ovarian cancer cell line (A2780) was subcutaneously implanted into the right flank of 7-week-old male nude rats, and was used in the same manner as in Test Example 1. Carboplatin was prepared by diluting a paraplatin injection (Bristol-Myers Squibb, 50 mg/5 mL) two-fold with physiological saline to enable administration at a carboplatin dose of 50 mg/kg/day. Further, the test liquid of Compound-I was prepared by adjusting its dose to 16 mg/kg/day.

Compound-I was administered once a day as oral administration for 14 days from Day 1, and carboplatin was administered via the tail vein of each mouse at Day 1 and Day 8. The single-drug administration group was administered 0.5% HPMC or a physiological saline as a vehicle instead of Compound-I or carboplatin.

Figure 5:
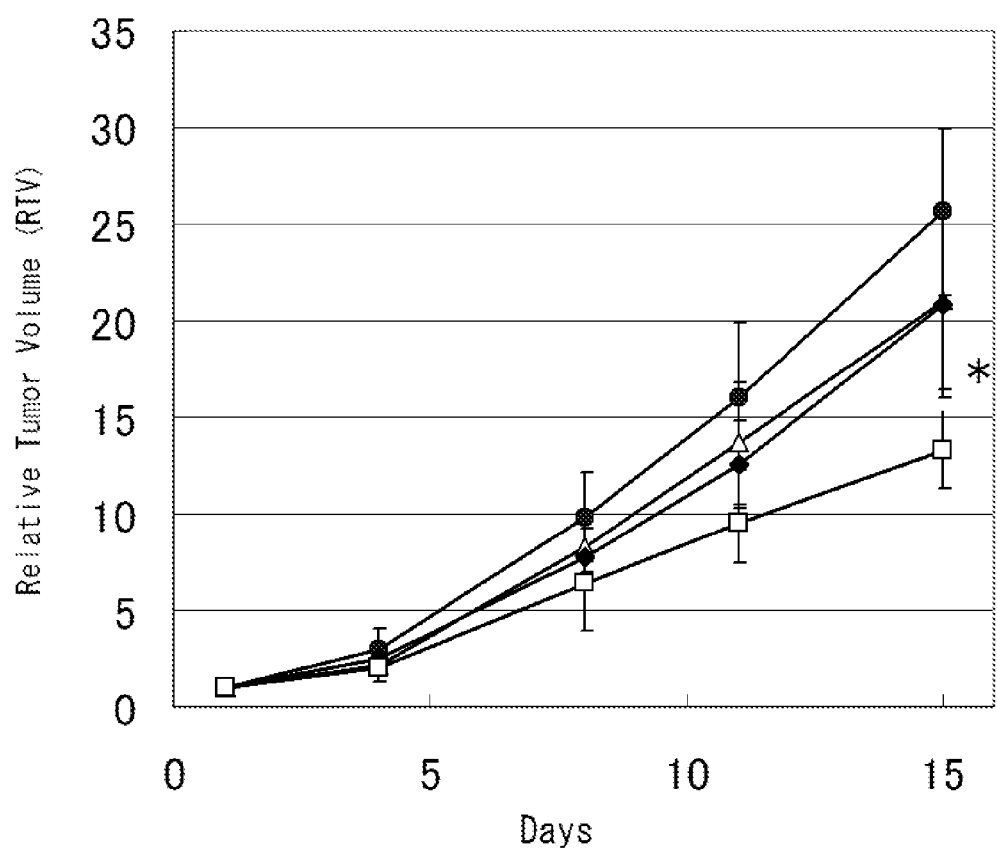
FIG. 5 Effect of combined use of Compound-I at 16 mg/kg/day with carboplatin in nude mice subcutaneously implanted with human ovarian cancer cell line A2780.

In the combined administration group, Compound-I and carboplatin were administered at doses of 16 mg/kg/day and 50 mg/kg/day, respectively, and the evaluation was performed in the same manner as in Test Example 1. FIG. 5 and Table 12 show the results. Further, the change in the body weight over time was evaluated as an index of toxicity in the same manner as in Test Example 1. The effect of the combined administration was also statistically determined in the same manner as in Test Example 1. In the figure and the table, the asterisk represents a result having a statistically significant difference compared with the single-drug administration group.

Figure 6:
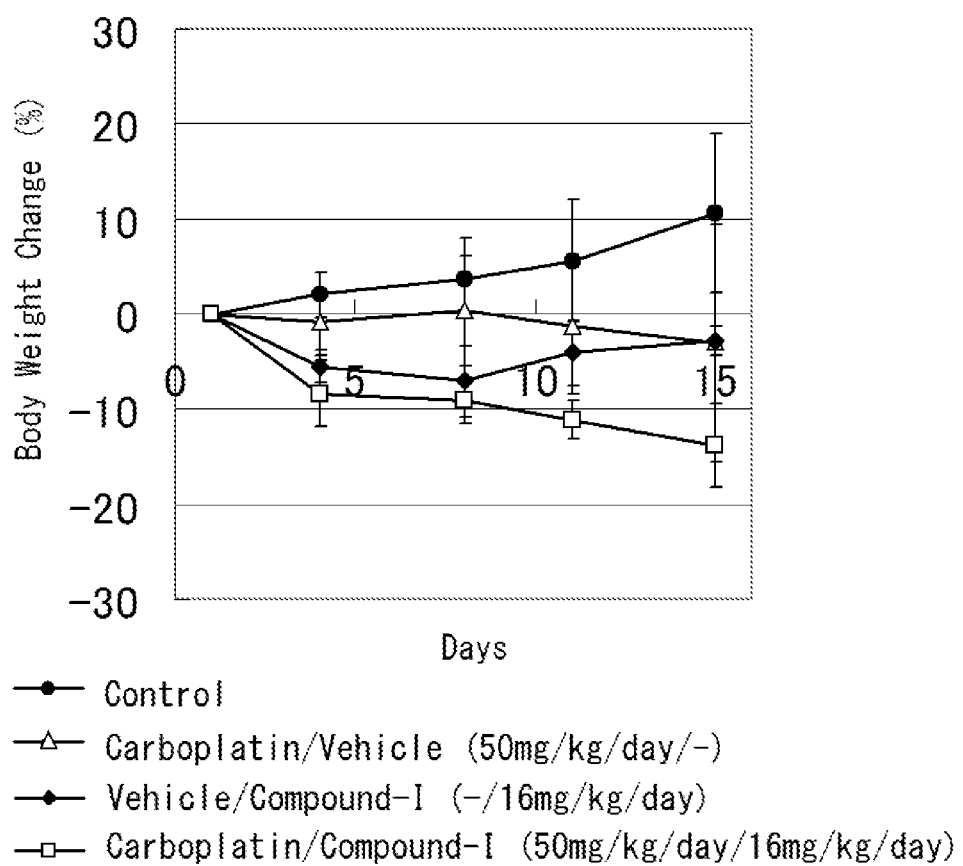
FIG. 6 Body weight changes of nude mice subcutaneously implanted with human ovarian cancer cell line A2780 upon combined use of Compound-I at 16 mg/kg/day with carboplatin.

FIG. 6 shows the results.

TABLE 12

| Group | Dose (mg/kg/day) | Schedule (day) | Route | RTV day 15 Mean ± SD | | T/C (%) |
|---|---|---|---|---|---|---|
| control(Vehicle/Vehicle) | — | 1, 8/1-14 | i.v./p.o. | 25.62 ± 4.32 | | 100 |
| Carboplatin/Vehicle | 50/— | 1, 8/1-14 | i.v./p.o. | 20.99 ± 4.57 | | 82 |
| Vehicle/compound-I | —/16 | 1, 8/1-14 | i.v./p.o. | 20.86 ± 4.84 | | 81 |
| Carboplatin/compound-I | 50/16 | 1, 8/1-14 | i.v./p.o. | 13.30 ± 1.94 | ‡ | 52 |

‡ overall mamimai $p < 0.05$ by closed testing procedure(Intersection-Union test)

Test Example 4
Potentiation of Antitumor Effect of Lapatinib

Human stomach cancer cell line (NCI-N87) was subcutaneously implanted into the right flank of 7-week-old male BALB/cA Jcl-nu/nu mice, and was used in the same manner as in Test Example 1. Lapatinib was prepared by adjusting its dose to 100 mg/kg/day. Further, the test liquid of Compound-I was prepared by adjusting its dose to 16 mg/kg/day. A vehicle of 0.5% HPMC/0.1% Tween 80 and a vehicle of 0.5% HPMC were used for lapatinib and Compound-I, respectively.

Figure 7:
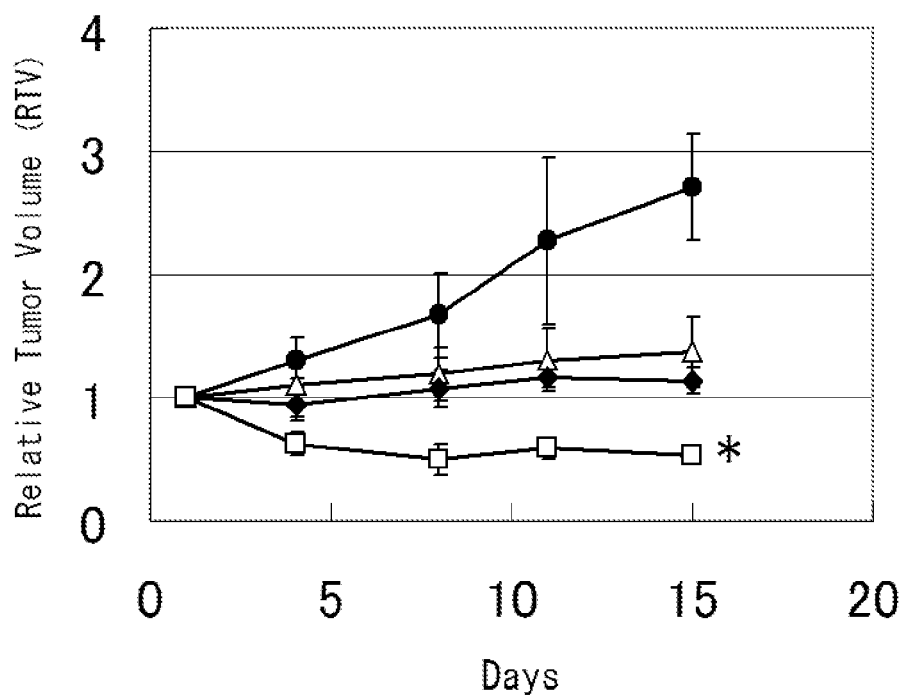
FIG. 7 Effect of combined use of Compound-I at 16 mg/kg/day with lapatinib in nude mice subcutaneously implanted with human stomach cancer cell line NCI-N87.
Figure 8:
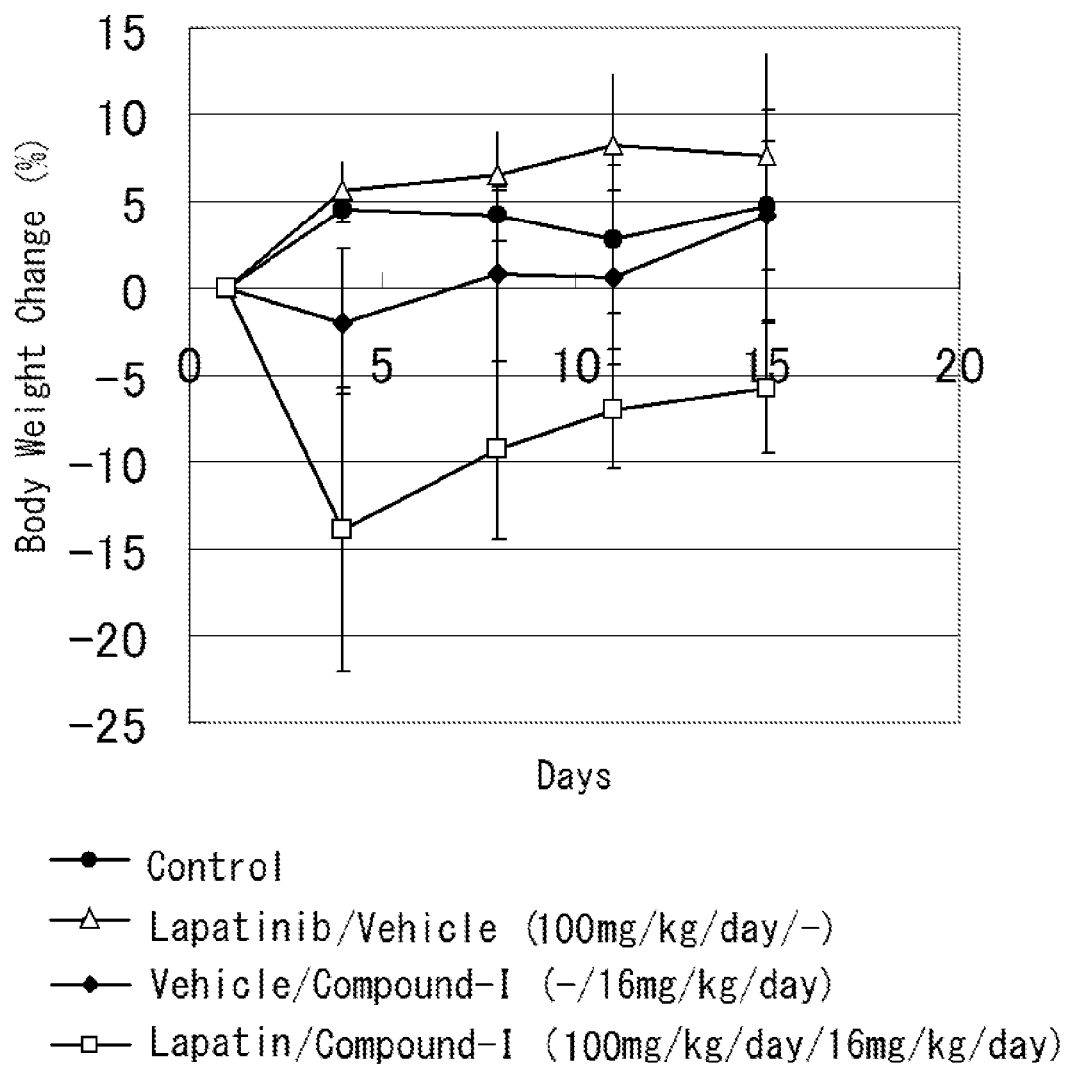
FIG. 8 Body weight changes of nude mice subcutaneously implanted with human stomach cancer cell line NCI-N87 upon combined use of Compound-I at 16 mg/kg/day with lapatinib.

In the single-drug administration group, Compound-I at a dose of 16 mg/kg/day or lapatinib at a dose of 100 mg/kg/day was orally administered once a day for 14 days from Day 1. In the combined administration group, Compound-I and lapatinib were administered at doses of 16 mg/kg/day and 100 mg/kg/day, respectively, and the evaluation was performed in the same manner as in Test Example 1. The effect of the combined administration was also statistically determined in the same manner as in Test Example 1. In the figure and the table, the asterisk represents a result having a statistically significant difference compared with the single-drug administration group. FIG. 7 and Table 13 show the results. Further, the change in the body weight over time was evaluated as an index of toxicity in the same manner as in Test Example 1. FIG. 8 shows the results.

TABLE 13

| Group | Dose (mg/kg/day) | Schedule (day) | Route | RTV day 15 Mean ± SD | | T/C (%) |
|---|---|---|---|---|---|---|
| control(Vehicle/Vehicle) | — | day 1-14, 1-14(q.d.) | p.o. | 2.71 ± 0.43 | | — |
| Lapatinib/Vehicle | 100/— | day 1-14, 1-14(q.d.) | p.o. | 1.37 ± 0.28 | | 51 |
| Vehicle/compound-I | —/16 | day 1-14, 1-14(q.d.) | p.o. | 1.14 ± 0.11 | | 42 |
| Lapatinib/compound-I | 100/16 | day 1-14, 1-14(q.d.) | p.o. | 0.53 ± 0.06 | ‡ | 20 |

‡ overall mamimai
$p < 0.01$ by closed testing procedure(Intersection-Union test)

Test Example 5

Potentiation of Antitumor Effect of Irinotecan

Human ovarian cancer cell line (A2780) was subcutaneously implanted into the right flank of 7-week-old male BALB/cA Jcl-nu/nu mice, and was used in the same manner as in Test Example 1. Irinotecan was prepared by diluting Campto intravenous infusion (Yakult Co., Ltd., 100 mg/5 mL) with physiological saline to enable administration at an irinotecan dose of 75 mg/kg/day. Further, the test liquid of Compound-I was prepared by adjusting its dose to 16 mg/kg/day. Physiological saline and 0.5% HPMC were used as vehicles of irinotecan and Compound-I, respectively.

Figure 9:
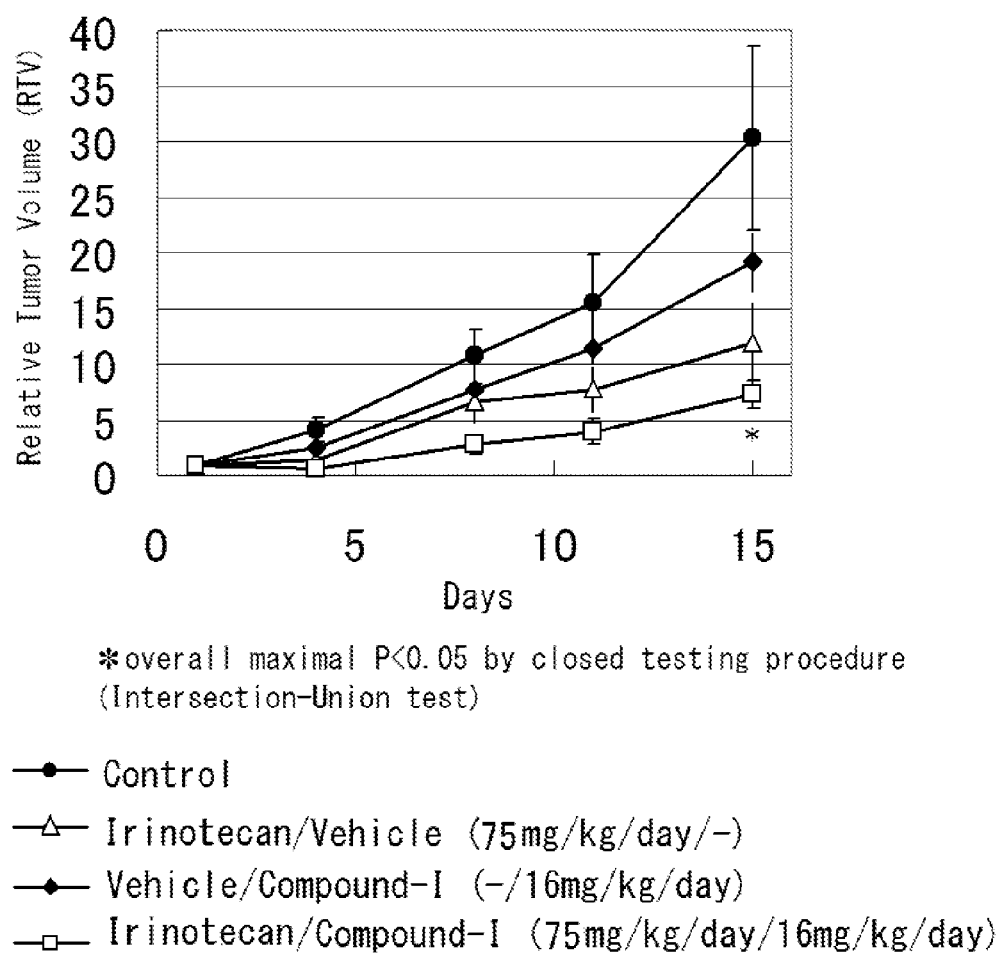
FIG. 9 Effect of combined use of Compound-I at 16 mg/kg/day with irinotecan in nude mice subcutaneously implanted with human ovarian cancer cell line A2780.
Figure 10:
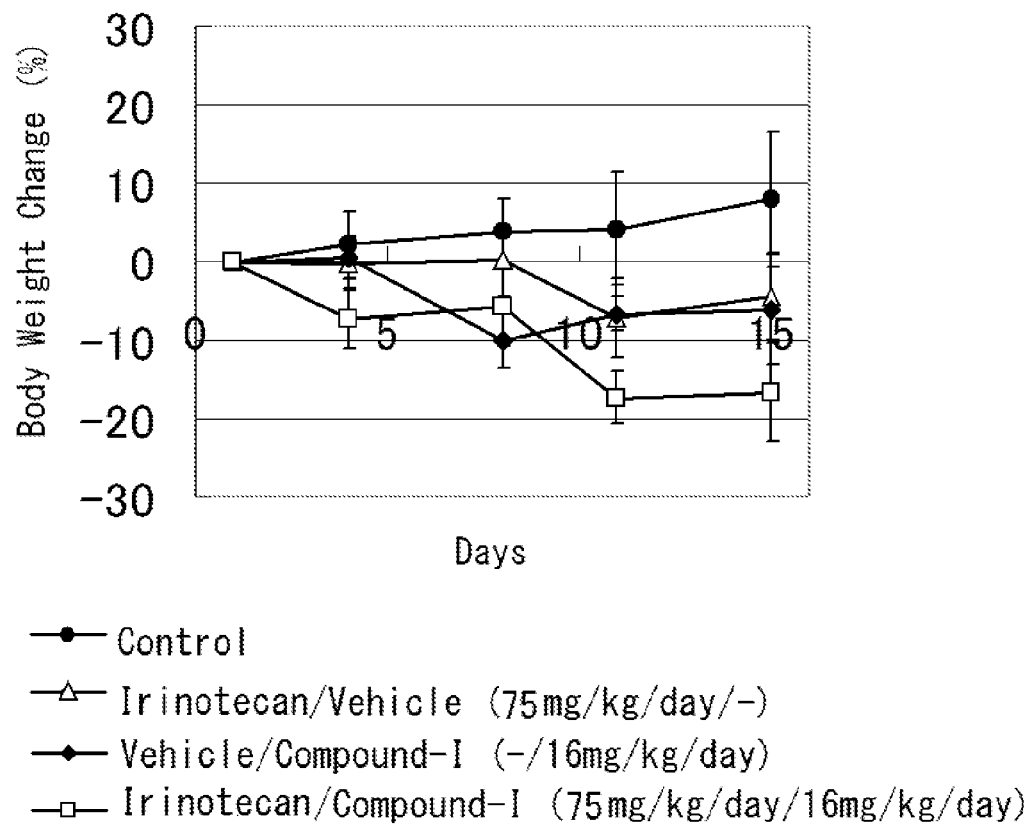
FIG. 10 Body weight changes of nude mice subcutaneously implanted with human ovarian cancer cell line A2780 upon combined use of Compound-I at 16 mg/kg/day with irinotecan.

In the single-drug administration group, Compound-I was orally administered once a day for 14 days from Day 1 at a dose of 16 mg/kg/day, and irinotecan was administered into the tail vein of each mouse at a dose of 75 mg/kg/day at Day 1 and Day 8. In the combined administration group, Compound-I and irinotecan at doses of 16 mg/kg/day and 75 mg/kg/day, respectively, were administered, and the evaluation was performed in the same manner as in Test Example 1. The effect of the combined administration was also statistically determined in the same manner as in Test Example 1. In the figure and the table, the asterisk represents a result having a statistically significant difference compared with the single-drug administration group. FIG. 9 and Table 14 show the results. Further, the change in the body weight over time was evaluated as an index of toxicity in the same manner as in Test Example 1. FIG. 10 shows the results.

Test Example 6

Potentiation of Antitumor Effect of Doxorubicin

Human ovarian cancer cell line (A2780) was subcutaneously implanted into the right flank of 7-week-old male BALB/cA Jcl-nu/nu mice, and was used in the same manner as in Test Example 1.

Figure 11:
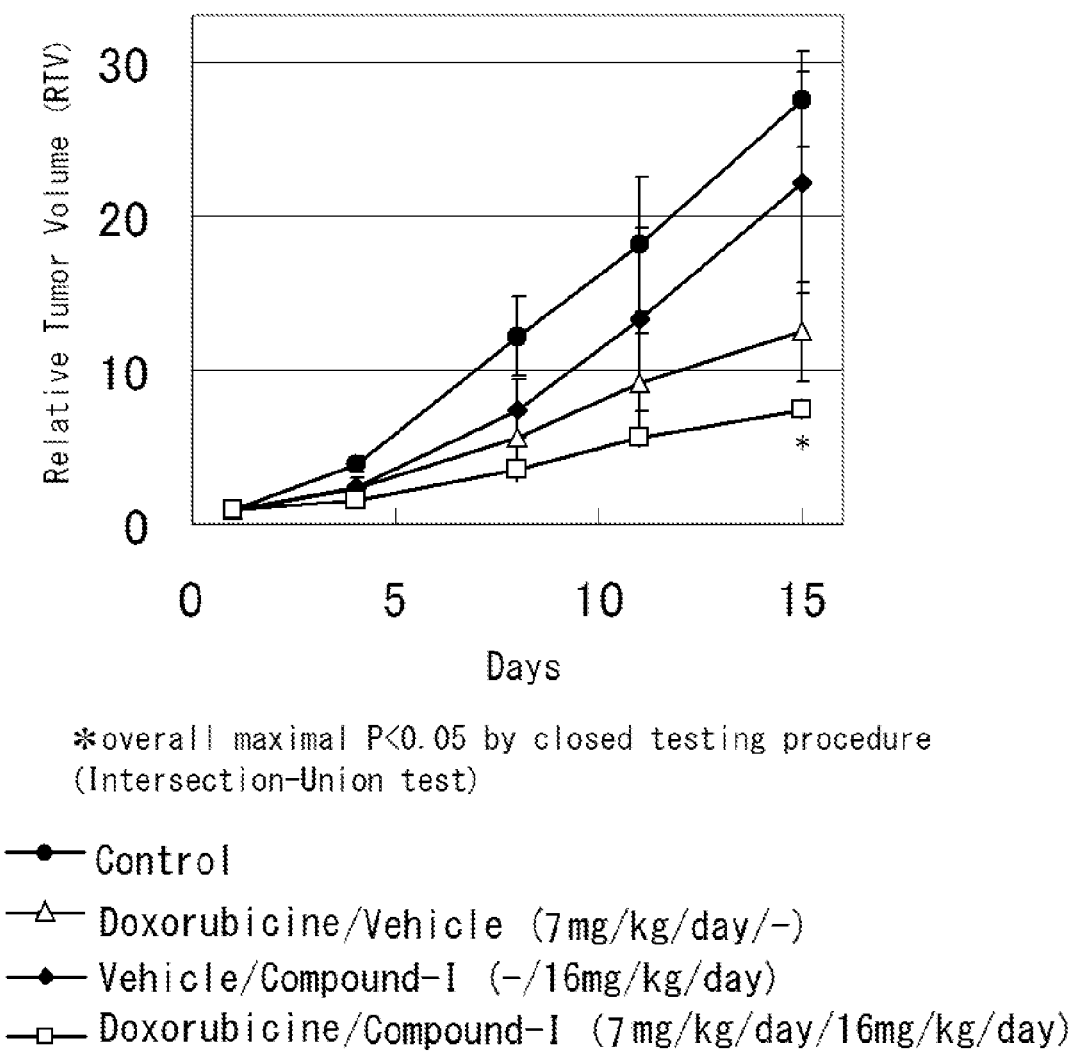
FIG. 11 Effect of combined use of Compound-I at 16 mg/kg/day with doxorubicin in nude mice subcutaneously implanted with human ovarian cancer cell line A2780.

In the group receiving only doxorubicin, the test liquid was prepared by diluting doxorubicin (Adriacin injection, Kyowa Hakko Kogyo Co., Ltd.) with physiological saline to enable administration at a doxorubicin dose of 7 mg/kg/day. In the groups receiving only Compound-I, the test liquid was prepared by diluting Compound-I with 0.5% HPMC to enable administration at a Compound-I dose of 16 mg/kg/day. In the combined administration group, Compound-I was administered at a dose of 16 mg/kg/day, and doxorubicin was administered at a dose of 7 mg/kg/day. Compound-I was orally administered for 14 consecutive days from Day 1, doxorubicin was orally administered at Day 1 and Day 8, and the evaluation was performed in the same manner as in Test Example 1. The effect of the combined administration was also statistically determined in the same manner as in Test Example 1. In the figure and the table, the asterisk represents a result having a statistically significant difference compared with the single-drug administration group. FIG. 11 and Table 15 show the results.

Figure 12:
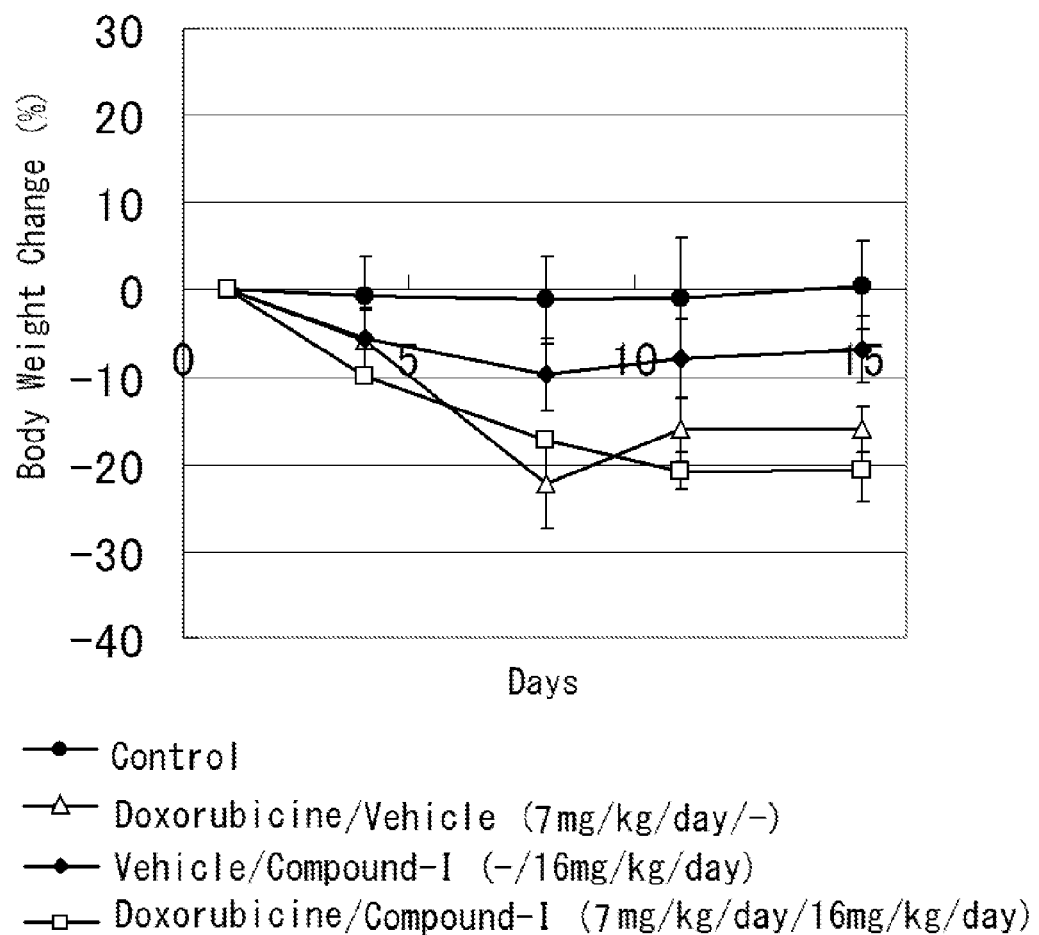
FIG. 12 Body weight changes of nude mice subcutaneously implanted with human ovarian cancer cell line A2780 upon combined use of Compound-I at 16 mg/kg/day with doxorubicin.

The change in the body weight over time was evaluated as an index of toxicity in the same manner as in Test Example 1. FIG. 12 shows the results.

TABLE 14

| Group | Dose (mg/kg/day) | Schedule (day) | Route | RTV day 15 Mean ± SD | | T/C (%) |
|---|---|---|---|---|---|---|
| control(Vehicle/Vehicle) | — | 1, 8/1-14 | p.o. | 30.29 ± 8.26 | | — |
| irinotecan/Vehicle | 75/— | 1, 8/1-14 | p.o. | 11.92 ± 3.68 | | 39 |
| Vehicle/compound-I | —/16 | 1, 8/1-14 | p.o. | 19.16 ± 2.60 | | 63 |
| irinotecan/compound-I | 75/16 | 1, 8/1-14 | p.o. | 7.31 ± 1.20 | ‡ | 24 |

‡ overall mamimai
$p < 0.05$ by closed testing procedure(Intersection-Union test)

TABLE 15

| Group | Dose (mg/kg/day) | Schedule (day) | Route | RTV day 15 Mean ± SD | | T/C (%) |
|---|---|---|---|---|---|---|
| control(Vehicle/Vehicle) | — | 1, 8/1-14 | p.o. | 27.57 ± 3.08 | | — |
| Doxorubicine/Vehicle | 7/— | 1, 8/1-14 | p.o. | 12.50 ± 3.19 | | 45 |
| Vehicle/compound-I | —/16 | 1, 8/1-14 | p.o. | 22.17 ± 7.20 | | 80 |
| Doxorubicine/compound-I | 7/16 | 1, 8/1-14 | p.o. | 7.49 ± 0.71 | ‡ | 27 |

‡ overall mamimai
p < 0.05 by closed testing procedure(Intersection-Union test)

Test Example 7

Potentiation of Antitumor Effect of Everolimus

Human stomach cancer cell line (NCI-N87) was subcutaneously implanted into the right flank of 7-week-old male BALB/cA Jcl-nu/nu mice, and was used in the same manner as in Test Example 1.

Figure 13:
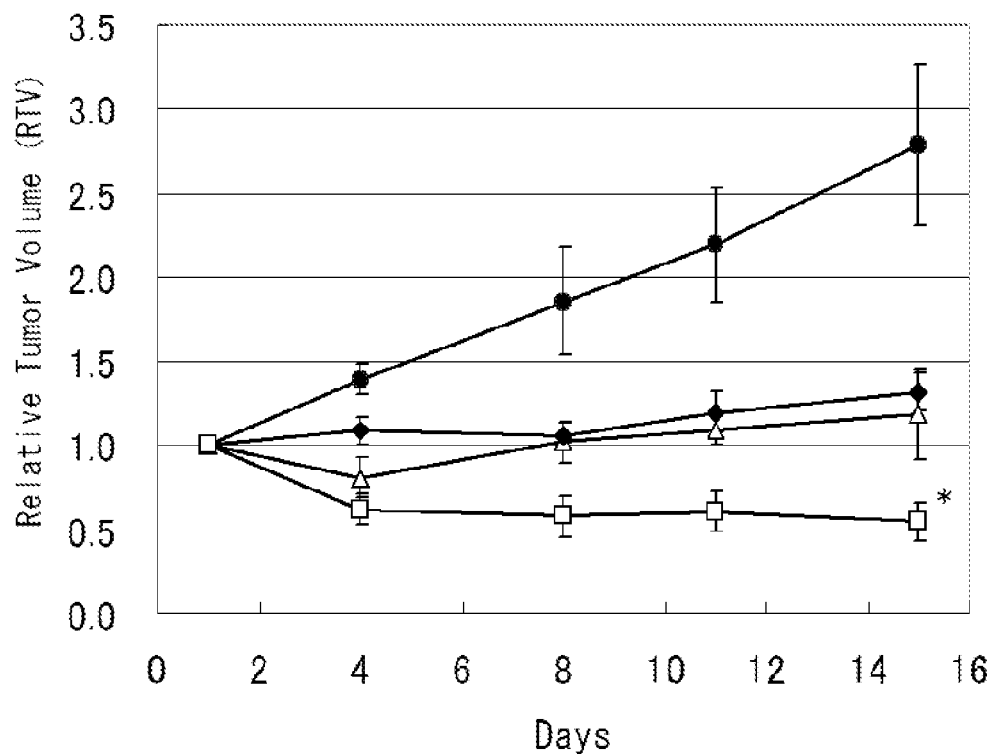
FIG. 13 Effect of combined use of Compound-I at 16 mg/kg/day with everolimus in nude mice subcutaneously implanted with human stomach cancer cell line NCI-N87.

In the group receiving only everolimus (IS Chemical Technology), the test liquid was prepared to enable administration at an everolimus dose of 5 mg/kg/day. A vehicle of 5% ethyl alcohol/5% PEG400/4% Tween 20/86% distilled water was used. In the groups receiving only Compound-I, the test liquid was prepared by diluting Compound-I with 0.5% HPMC to enable administration at a Compound-I dose of 16 mg/kg/day. In the combined administration group, Compound-I was administered at a dose of 16 mg/kg/day, and everolimus was administered at a dose of 5 mg/kg/day. Both Compound-I and everolimus were orally administered once a day for 14 days from Day 1, and the evaluation was performed in the same manner as in Test Example 1. FIG. 13 and Table 16 show the results.

The evaluation of the effect of the combined administration was performed such that when the average RTV value of the combined administration group was statistically significantly smaller than the average RTV value of the single-drug administration group (Welch's Intersection-Union test, overall maximum p<0.05), the combined administration was determined to be effective. In the figure and the table, the asterisk represents a result having a statistically significant difference compared with the single-drug administration group.

Figure 14:
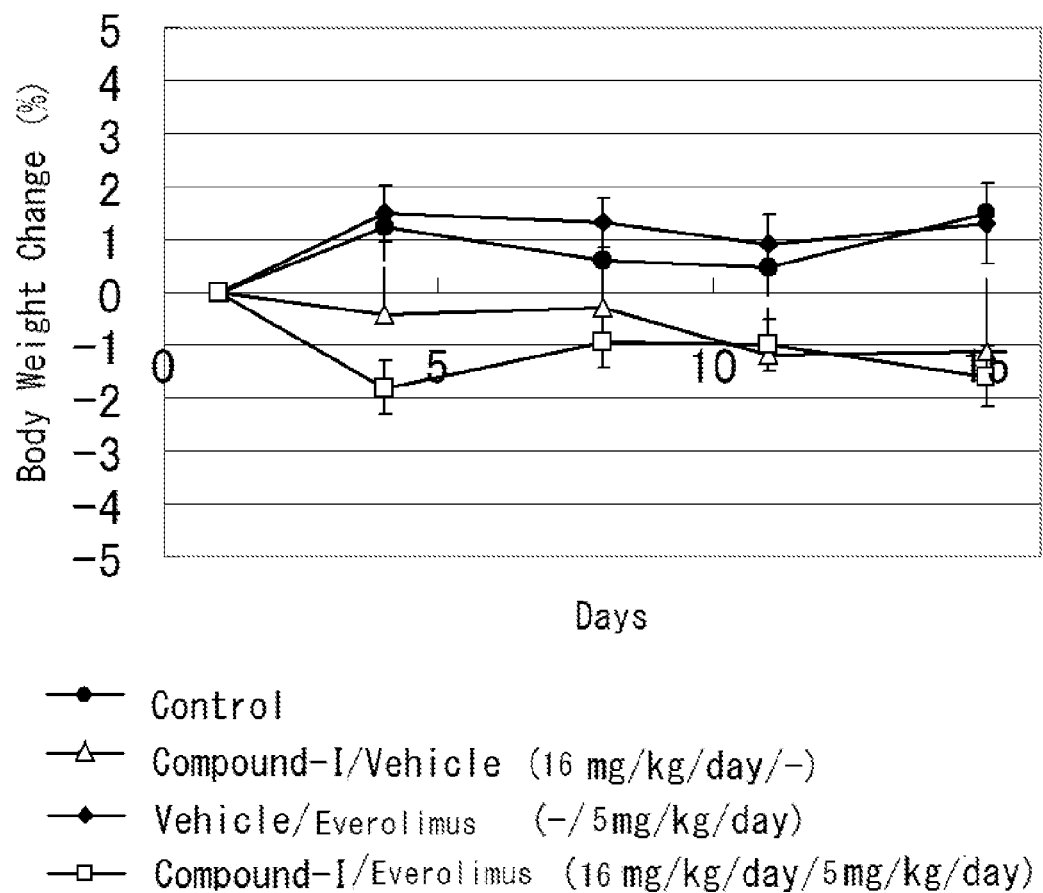
FIG. 14 Body weight changes of nude mice subcutaneously implanted with human stomach cancer cell line NCI-N87 upon combined use of Compound-I at 16 mg/kg/day with everolimus.

The change in the body weight over time was evaluated as an index of toxicity in the same manner as in Test Example 1. FIG. 14 shows the results.

Test Example 8

Potentiation of Antitumor Effect of TS-1

Human stomach cancer cell line (4-1ST) was subcutaneously implanted into the right flank of 6-week-old male BALB/cA Jcl-nu/nu mice, and was used in the same manner as in Test Example 1.

TS-1 was prepared by mixing FT (tegafur; Taiho Pharmaceutical Co., Ltd.), CDHP (gimeracil; Taiho Pharmaceutical Co., Ltd.) and Oxo (oteracil potassium; Taiho Pharmaceutical Co., Ltd.) at a molar ratio of 1:0.4:1, adding a 0.5% (w/v) HPMC aqueous solution to the mixture at an FT concentration of 1.66 mg/mL, and subjecting the mixture to a ultrasonic treatment to obtain an even suspension (an administration liquid having a double concentration of the liquid in the group of 8.3 mg/kg/day dose). The suspension was diluted two-fold with a 0.5% (w/v) HPMC aqueous solution to a concentration of 0.83 mg/mL, thereby yielding an administration liquid to be used for the group of 8.3 mg/kg/day dose. Further, the test liquid of Compound-I was prepared by adjusting its dose to 16 and 24 mg/kg/day.

Figure 15:
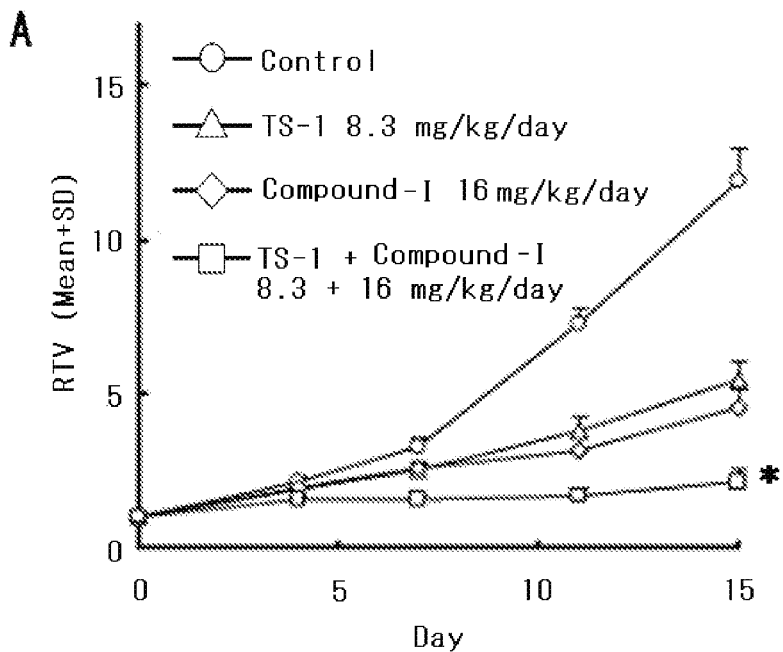
FIG. 15 Effect of combined use of Compound-I, at 16 mg/kg/day (A), and 24 mg/kg/day (B), with TS-1 in nude mice subcutaneously implanted with human stomach cancer cell line 4-1ST.
Figure 15:
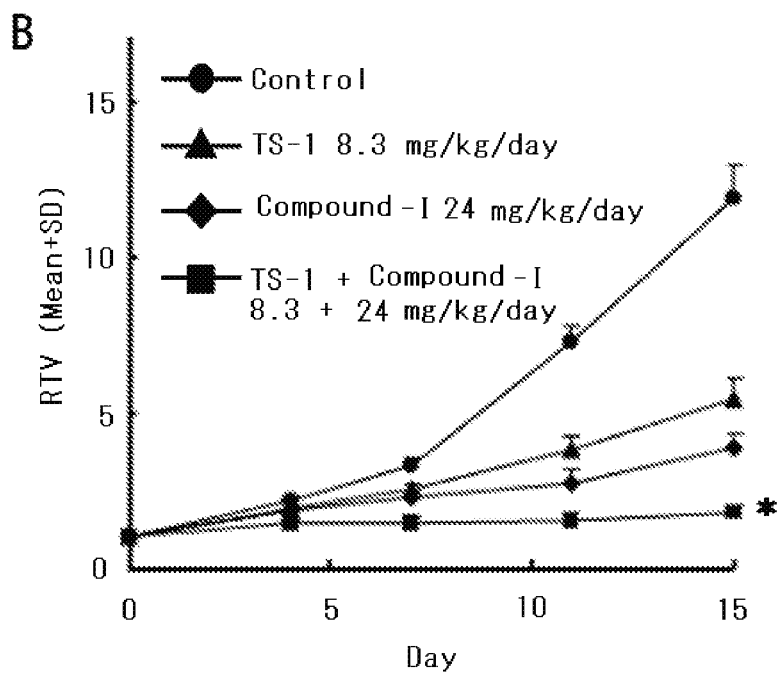

Compound-I and TS-1 were orally administered once a day for 14 days from Day 1. In the combined administration groups, Compound-I at a dose of 16 and 24 mg/kg/day, and TS-1 at a dose of 8.3 mg/kg/day were administered, and the evaluation was performed in the same manner as in Test Example 1. FIGS. 15A and 15B, and Table 17 show the results.

In the same manner as in Test Example 7, the effect of the combined administration was also statistically determined. In the figure and the table, the asterisk represents a result having a statistically significant difference compared with the single-drug administration group.

Figure 16:
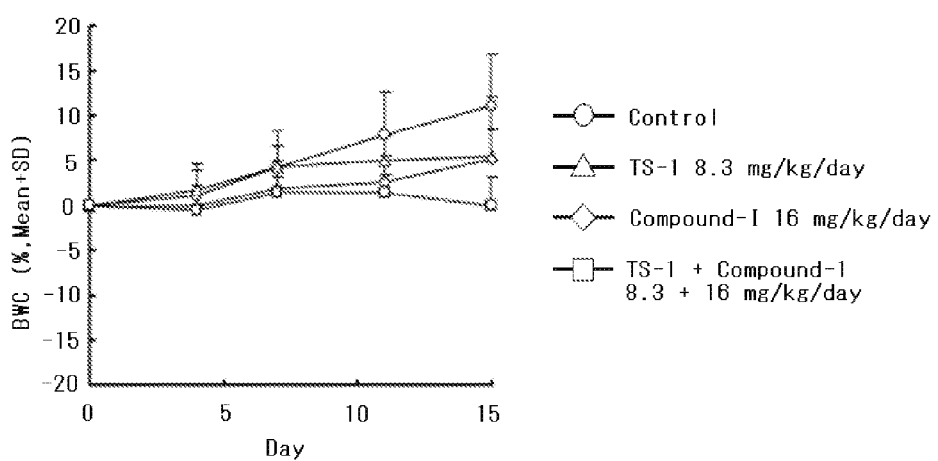
FIG. 16 Body weight changes of nude mice subcutaneously implanted with human stomach cancer cell line 4-1ST upon combined use of Compound-I, at 16 mg/kg/day (A), and 24 mg/kg day (B), with TS-1.
Figure 16:
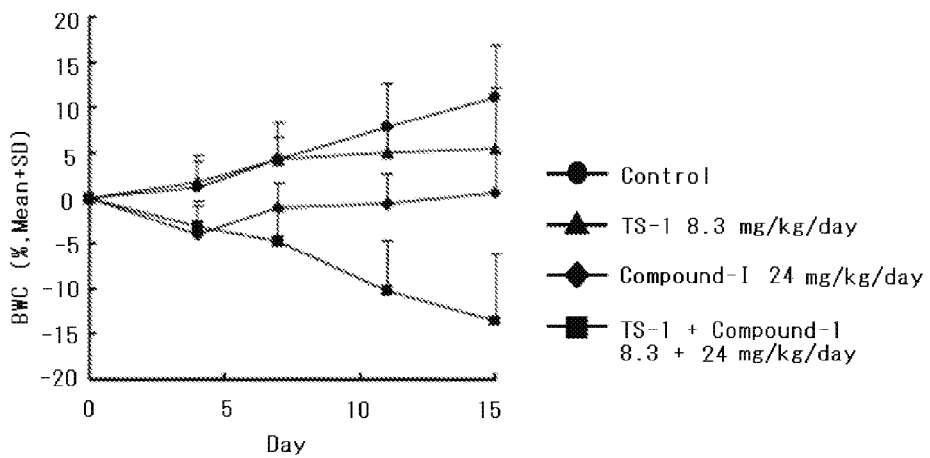

The change in the body weight over time was evaluated as an index of toxicity in the same manner as in Test Example 1. FIGS. 16A and 16B show the results.

TABLE 16

| Group | Dose (mg/kg/day) | Schedule (day) | Route | RTV day 15 Mean ± SD | | T/C (%) |
|---|---|---|---|---|---|---|
| control(Vehicle/Vehicle) | — | day 1-14, 1-14 | p.o./p.o. | 2.78 ± 0.48 | | — |
| compound-I/Vehicle | 16/— | day 1-14, 1-14 | p.o./p.o. | 1.19 ± 0.27 | | 43 |
| Vehicle/Everolimus | —/5 | day 1-14, 1-14 | p.o./p.o. | 1.32 ± 0.11 | | 47.3 |
| compound-I/Everolimus | 16/5 | day 1-14, 1-14 | p.o./p.o. | 0.55 ± 0.11 | ‡ | 19.7 |

‡ overall mamimai
p < 0.01 by closed testing procedure(Intersection-Union test)

TABLE 17

| Drug | Dose (mg/kg/day) | Schedule (day) | Route | RTV day 15 Mean ± SD | | T/C (%) |
|---|---|---|---|---|---|---|
| control(0.5% HPMC) | — | day 1-14 | p.o. | 11.89 ± 1.04 | | — |
| TS-1 | 8.3 | day 1-14 | p.o. | 5.44 ± 0.62 | | 45.8 |
| compound-I | 16 | day 1-14 | p.o. | 4.53 ± 0.59 | | 38.1 |
| compound-I | 24 | day 1-14 | p.o. | 3.83 ± 0.48 | | 32.2 |
| TS-1/compound-I | 8.3/16 | day 1-14 | p.o. | 2.17 ± 0.36 | ‡ | 18.3 |
| TS-1/compound-I | 8.3/24 | day 1-14 | p.o. | 1.76 ± 0.26 | ‡ | 14.8 |

‡ overall mamimai
p < 0.01 by closed testing procedure(Intersection-Union test)

Test Example 9

Potentiation of Cancer Cell Proliferation Inhibitory Effect of Bortezomib

Human multiple myeloma-derived cell line MM.1S or MM.1R was subcultured in RPMI-1640 medium containing 10% fetal bovine serum. MM.1S or MM.1R cells were seeded in a 384-microwell plate (1500 cells/20 µL/well), and cultured overnight in an incubator at 37° C., 5% $CO_2$, and 100% humidity. The plate was taken out from the incubator, and Compound-II was added to the wells after being diluted with RPMI-1640 medium containing a DMSO solvent and 10% fetal bovine serum to final concentrations of 7.8, 15.6, 31.3, 62.5, 125, 250, 500, 1000, and 2000 nM; each concentration was added to 4 wells each (5 µL per well). Bortezomib was added to the wells after being diluted with RPMI-1640 medium containing a DMSO solvent and 10% fetal bovine serum to final concentrations of 7.8, 15.6, 31.3, 62.5, 125, 250, 500, 1000, and 2000 nM; each concentration was added to 4 wells each (5 µL per well). In the combined administration groups, Compound-II and bortezomib were diluted to have all of the combinations of the above final concentrations, and each combination was added to 4 wells each (5 µL per well). As a control group, DMSO diluted with RPMI-1640 medium containing 10% fetal bovine serum was added to 16 wells for control measurement (5 µL per well). The plate was placed back into the incubator, and cultured for three more days. After three days, CellTiter-Glo™ (Promega) was added to the wells (25 µL per well), and the number of cells was counted. The results of the cell proliferation inhibitory effect obtained by the treatment using only Compound-II, the treatment using only bortezomib, and the treatment using the two drugs were analyzed according to the median-effect method disclosed in Adv. Enzyme Regul. 1984; 22:27-55 by Chou and Talalay using CalcuSyn Version 2.1 (Biosoft), thereby obtaining a Combination Index (CI) as the index of the effect of the combined administration. The effect was determined to be competitive when the CI value was 1.2 or more, additive when the CI value was less than 1.2 and not less than 0.85, and synergistic when the CI value was less than 0.85. The table below shows the Combination Index. The CI value was 0.71 to 1.0 for MM.1S, and 0.60 to 1.13 for MM.1S, showing that Compound-II showed an additive or synergistic cell proliferation inhibitory effect when used with bortezomib.

TABLE 18

| Combination Index for the combined use of Compound-II and bortezomib | | | |
|---|---|---|---|
| Cell line (ratio of bortezomib:Compound-II) | Combination Index (CI) | | |
| | ED50 | ED75 | ED90 |
| MM.IS (8:125) | 1.00 | 0.81 | 0.71 |
| MM.IR (1:125) | 1.13 | 0.77 | 0.60 |

Test Example 10

Potentiation of Cancer Cell Proliferation Inhibitory Effect of Erlotinib

Human stomach cancer derived cell line NCI-N87 was subcultured in RPMI-1640 medium containing 10% fetal bovine serum. NCI-N87 cells were seeded in a 96-microwell plate (3750 cells/100 µL/well), and cultured overnight in an incubator at 37° C., 5% $CO_2$, and 100% humidity. A dilution series of Compound-II obtained by diluting it with a 200-fold DMSO solution to final concentrations of 0 (DMSO only), 10, 30, 100, 300, 1000, 3000, and 10000 nM, and a dilution series of erlotinib obtained by diluting it to final concentrations 0.1, 0.3, 1, 3, and 10 times that of Compound-II. The plate was taken out from the incubator, and each of the above DMSO-diluted liquids was diluted to a concentration four times that of the final concentration using RPMI-1640 medium containing 10% fetal bovine serum. In the combined administration groups, Compound-II and erlotinib were added to the wells in all of the combinations of the above final concentrations (50 µL per well). At this point, the total medium amount in the wells was 200 µL. As a control group, DMSO diluted with RPMI-1640 medium containing 10% fetal bovine serum was added to the wells (100 µL per well). The plate was placed back into the incubator, and cultured for three more days. After three days, the plate was taken out at room temperature, and 100 µL of the supernatant was removed. CellTiter-Glo™ (Promega) was added to the wells (50 µL per well), and the number of cells was counted. The results of cell the proliferation inhibitory effect obtained by the treatment using only Compound-II, the treatment using only erlotinib, and the treatment using the two drugs were analyzed in the same manner as in Test Example 9, thereby obtaining a Combination Index (CI) as the index of the effect of the combined administration. The effect was determined to be competitive when the CI value was 1.2 or more, additive when the CI value was less than 1.2 and not less than 0.85, and synergistic when the CI value was less than 0.85. Table 19 below shows the Combination Index. The CI value was 0.25 to 0.52 for NCI-N87 cell line, showing that Compound-II showed a synergistic cell proliferation inhibitory effect when used with erlotinib.

TABLE 19

Combination Index for the combined use of Compound-II
and erlotinib in NCI-N87 cell line

| Cell line (ratio of | Combination Index (CI) | | |
|---|---|---|---|
| Compound-II:erlotinib) | ED50 | ED75 | ED90 |
| NCI-N87 (1:10) | 0.48 | 0.40 | 0.33 |
| NCI-N87 (3:10) | 0.45 | 0.34 | 0.29 |
| NCI-N87 (10:10) | 0.52 | 0.34 | 0.25 |

Test Example 11

Potentiation of Cancer Cell Proliferation Inhibitory Effect of Trastuzumab (Herceptin)

Human stomach cancer cell line (4-1ST) was subcutaneously implanted into the right flank of 6-week-old male BALB/cA Jcl-nu/nu mice, and was used in the same manner as in Test Example 1.

According to the package insert, 7.2 mL of water for injection was added to a vial containing 150 mg of trastuzumab (Roche Pharma) using a sterilized injection syringe. The resulting 21 mg/mL solution was kept in a freezer. At the time of use, the frozen solution was diluted 10.5-fold with 4.75 mL of physiological saline at a trastuzumab concentration of 2.0 mg/mL, to yield a liquid for administration at a trastuzumab dose of 20 mg/kg/day. The test liquids of Compound-I were prepared to enable administration at doses of 16 and 24 mg/kg/day.

Figure 17:
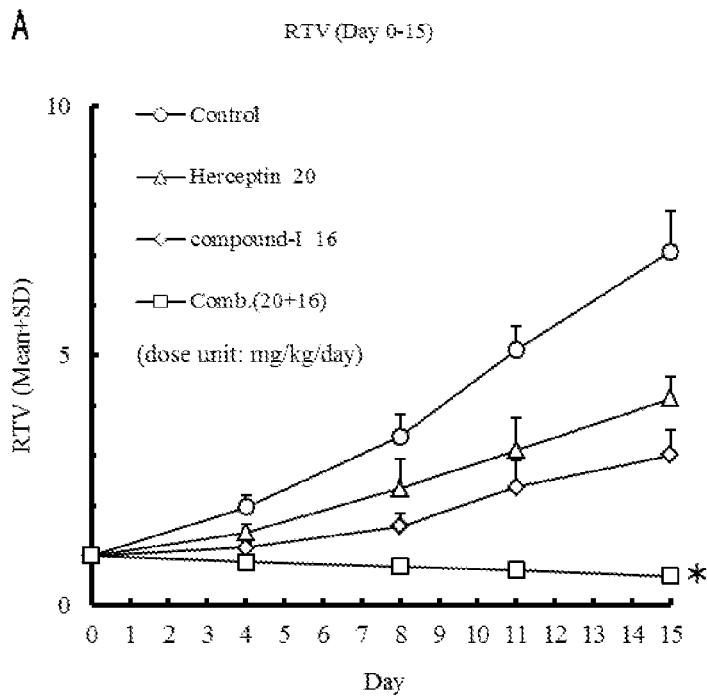
FIG. 17 Effect of combined use of Compound-I, at 16 mg/kg/day (A), and 24 mg/kg/day (B), with trastuzumab in nude mice subcutaneously implanted with human stomach cancer cell line 4-1ST.
Figure 17:
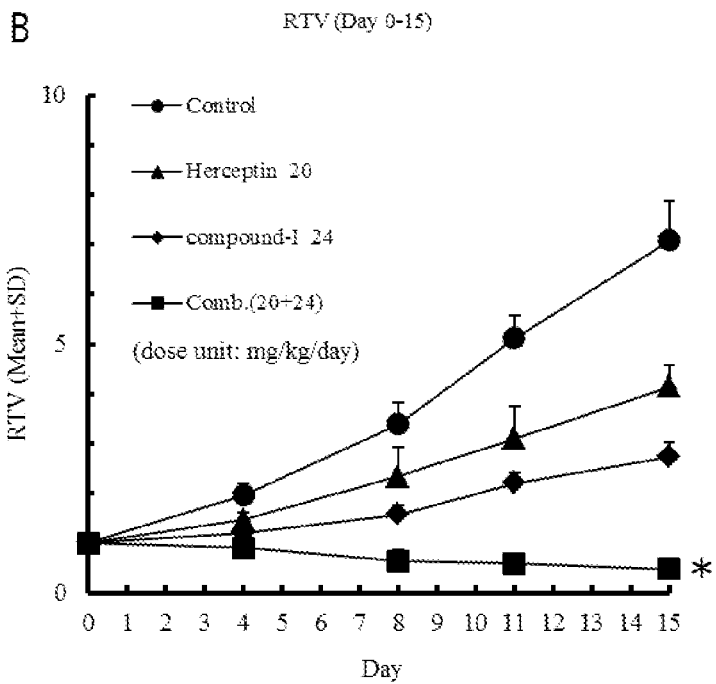

Compound-I and trastuzumab were administered once a day from Day 1 to 14. In the combined administration groups, Compound-I was administrated at a dose of 16 and 24 mg/kg/day, trastuzumab was administrated at a dose of 20 mg/kg/day, and the evaluation was performed in the same manner as in Test Example 1. FIGS. 17A and 17B and Table 20 show the results. In the medium/Compound I administration group, the test liquid was orally administered once a day for consecutive days. In the trastuzumab administration group, the test liquid was intraperitoneally administered once a day for consecutive days.

The effect of the combined administration was statistically determined in the same manner as in Test Example 7. In the figure and the table, the asterisk represents a result having a statistically significant difference compared with the single-drug administration group.

Figure 18:
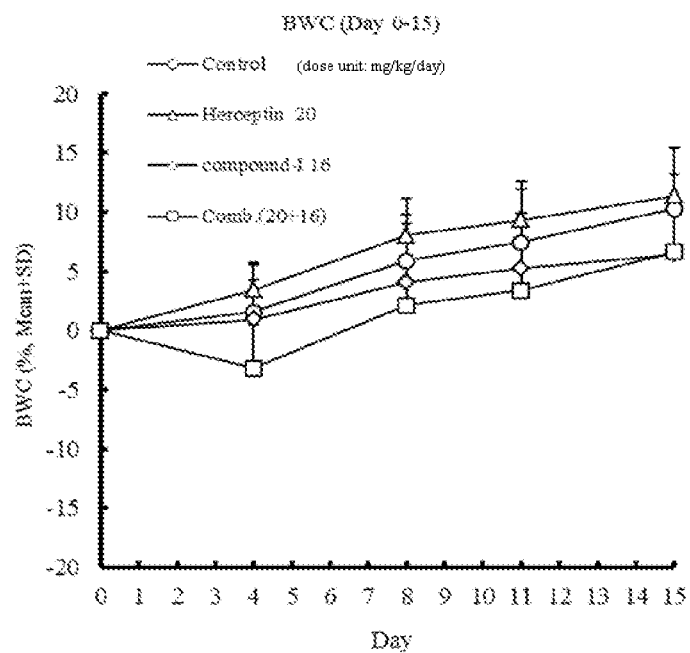
FIG. 18 Body weight changes of nude mice subcutaneously implanted with human stomach cancer cell line 4-1ST upon combined use of Compound-I, at 16 mg/kg/day (A), and 24 mg/kg/day (B), with trastuzumab.
Figure 18:
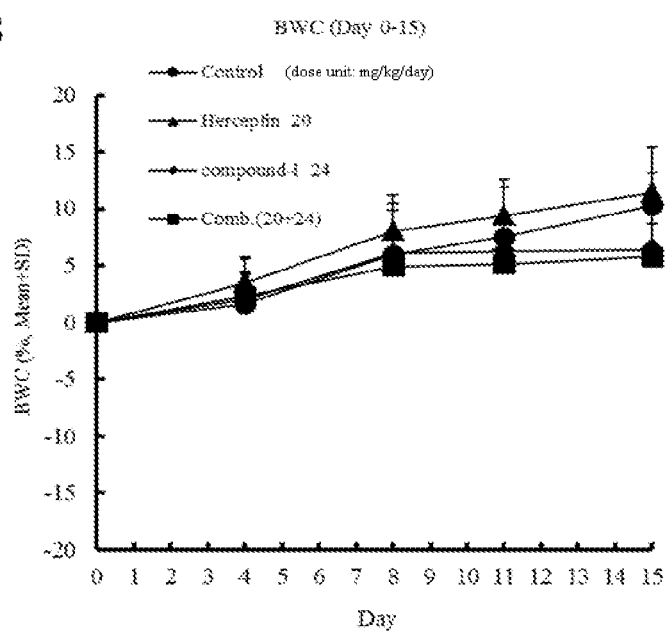

The change in the body weight over time was evaluated as an index of toxicity in the same manner as in Test Example 1. FIGS. 18A and 18B show the results.

TABLE 20

| Drug | Dose (mg/kg/day) | Treatment | RTV[b] (mean ± SD) | TGI[c] (%) |
|---|---|---|---|---|
| Control | — | Day 1~14, p.o. | 7.09 ± 0.80 | — |
| Herceptin | 20 | Day 1, 8, i.p. | 4.15 ± 0.42 | 41.4 |
| compound-I | 16 | Day 1~14, p.o. | 3.01 ± 0.51 | 57.5 |
| compound-I | 24 | Day 1~14, p.o. | 2.74 ± 0.29 | 61.4 |
| Herceptin + compound-I | 20 + 16 | | 0.59 ± 0.16 * | 91.6 |
| Herceptin + compound-I | 20 + 24 | | 0.48 ± 0.11 * | 93.2 |

* overall maximal
p < 0.01 by closed testing procedure (Intersection-Union Test), respectively.

As is clearly shown in FIGS. 1, 3, 5, 7, 9, 11, 13, 15 and 17, imidazooxazine compound (I) or a pharmaceutically acceptable salt thereof significantly potentiated various antitumor agents. The effect was observed even at a low dose of imidazooxazine compound (I), i.e., 8 mg/kg/day (an amount at which the imidazooxazine compound (I) does not exhibit the antitumor effect alone; FIG. 1 and Table 11). In the nude mice group receiving the high dose (24 mg/kg/day) (a dose for producing the maximum effect), significant tumor shrinkage was observed by the combined administration (Tables 11 and 13). Further, the weight reduction was not significantly worsened in the combined administration group compared with the weight reduction by the single administration of each antitumor agent (FIGS. 2, 4, 12, and 14). This revealed that the compound of the present invention potentiates various antitumor agents without potentiating their toxicity.

Further, for example, as shown in the comparison of FIGS. 1 and 3, although the antitumor effect (drug sensitivity) of paclitaxel varies depending on the tumor type, even at the same dose, the potentiation of the effect was observed in all cases by the combined use thereof with imidazooxazine compound (I). More specifically, even for tumors having low sensitivity to paclitaxel, the combined use of paclitaxel and imidazooxazine compound (I) is expected to potentiate the tumor proliferation inhibitory effect of paclitaxel. This indicates that the antitumor spectrum of an antitumor agent is enlarged by the combined use thereof with imidazooxazine compound (I).

More specifically, the combinations of imidazooxazine compound (I) or a pharmaceutically acceptable salt thereof and various antitumor agents showed potentiation of antitumor effect and enlargement in antitumor spectrum without showing a significant increase in toxicity.

Test Example 12

Potentiation of Cancer Cell Proliferation Inhibitory Effect of Metformin

Human ovarian cancer cell line A2780 was subcultured in RPMI-1640 medium containing 10% fetal bovine serum. A2780 cells were seeded in a 96-microwell plate (2000 cells/100 μL/well), and cultured overnight in an incubator at 37° C., 5% $CO_2$, and 100% humidity. Compound-I was diluted with a 200-fold DMSO solution to final concentrations of 0 (DMSO only), 10, 30, 100, 300, 1000, 3000, and 10000 nM, and metformin was diluted with RPMI-1640 medium containing 10% fetal bovine serum to final concentrations 1000, 3333, and 10000 times that of Compound-I. The plate was taken out from the incubator. In the combined administration groups of Compound-I and metformin, Compound-I and metformin were diluted to have all of the combinations of the above final concentrations, and added to the wells. At this point, the total medium amount in the wells was 200 μL. As a control group, DMSO diluted with RPMI-1640 medium containing 10% fetal bovine serum to a final concentration of 0.5% was added to the wells (100 μL per well). The plate was placed back into the incubator, and cultured for three more days. After three days, the plate was taken out at room temperature, and 150 μL of the supernatant was removed. Cell-Titer-Glo™ (Promega) was added to the wells (50 μL per well), and the number of cells was counted. The results of the cell proliferation inhibitory effect obtained by the treatment using only Compound-I, the treatment using only erlotinib, and the treatment using the two drugs were analyzed in the same manner as in Test Example 9, thereby obtaining a Combination Index (CI) as the index of the effect of the combined administration. The effect was determined to be competitive when the CI value was 1.2 or more, additive when the CI value was less than 1.2 and not less than 0.85, and synergistic when the CI value was less than 0.85. The table below shows the Combination Index. The CI value was 0.08 to 0.96 for A2780 cell line, showing that Compound-I showed an additive or synergistic cell proliferation inhibitory effect when used with metformin.

TABLE 21

Combination Index for the combined use of Compound-I and metformin in A2780 cell line

| Cell line (ration of | Combination Index (CI) | | |
|---|---|---|---|
| Compound-I:metformin) | ED50 | ED75 | ED90 |
| A2780 (1:10000) | 0.96 | 0.25 | 0.08 |
| A2780 (3:10000) | 0.66 | 0.21 | 0.10 |
| A2780 (1:1000) | 0.37 | 0.18 | 0.14 |

Test Example 13

Potentiation of Cancer Cell Proliferation Inhibitory Effect of Docetaxel

Human ovarian cancer cell line A2780 was subcultured in RPMI-1640 medium containing 10% fetal bovine serum. A2780 cells were seeded in a 96-microwell plate (2000 cells/150 μL/well), and cultured overnight in an incubator at 37° C., 5% CO$_2$, and 100% humidity. Compound-I was diluted with a 200-fold DMSO solution to final concentrations of 0 (DMSO only), 10, 30, 100, 300, 1000, 3000, and 10000 nM, and docetaxel was diluted with RPMI-1640 medium containing 10% fetal bovine serum to final concentrations 0.01 and 0.03 time that of Compound-I. The plate was taken out from the incubator, and, as combined administration groups of Compound-I and docetaxel, Compound-I and docetaxel were diluted to have all of the combinations of the above final concentrations, and added to the wells. At this point, the total medium amount in the wells was 200 μL. As a control group, DMSO diluted with RPMI-1640 medium containing 10% fetal bovine serum to a final concentration of 0.5% was added to the wells (50 μL per well). The plate was placed back into the incubator, and cultured for three more days. After three days, the plate was taken out at room temperature, and 150 μL of the supernatant was removed. CellTiter-Glo™ (Promega) was added to the wells (50 μL per well), and the number of cells was counted. The results of the cell proliferation inhibitory effect obtained by the treatment using only Compound-I, the treatment using only docetaxel, and the treatment using the two drugs were analyzed in the same manner as in Test Example 9, thereby obtaining a Combination Index (CI) as the index of the effect of the combined administration. The effect was determined to be competitive when the CI value was 1.2 or more, additive when the CI value was less than 1.2 and not less than 0.85, and synergistic when the CI value was less than 0.85. The table below shows the Combination Index. The CI value was 0.33 to 0.67 for A2780 cell line, showing that Compound-I showed an additive or synergistic cell proliferation inhibitory effect when used with docetaxel.

TABLE 22

Combination Index for the combined use of Compound-I and docetaxel in A2780 cell line

| Cell line (ration of | Combination Index (CI) | | |
|---|---|---|---|
| Compound-I:docetaxel) | ED50 | ED75 | ED90 |
| A2780 (100:3) | 0.33 | 0.33 | 0.33 |
| A2780 (100:1) | 0.47 | 0.56 | 0.67 |

The invention claimed is:

1. A method for potentiating one or more antitumor agents, comprising administering an imidazooxazine compound represented by Formula (I), or a pharmaceutically acceptable salt thereof in combination with one or more antitumor agents, wherein said imidazooxazine compound is in an amount effective for potentiating the effect of said one or more antitumor agents, to a patient in need of such treatment,

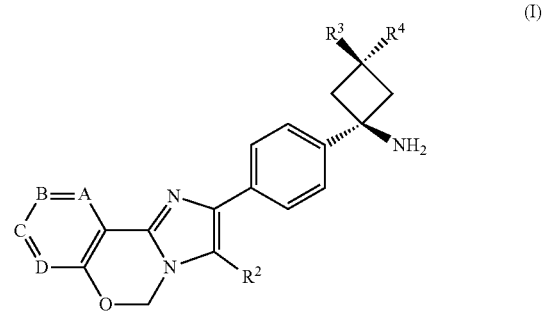

wherein A, B, C, and D represent C—R$^{1a}$, C—R$^{1b}$, C—R$^{1c}$, and C—R$^{1d}$, respectively, or one or two of A, B, C, and D represent an N atom;
at least two of R$^{1a}$, R$^{1b}$, R$^{1c}$, and R$^{1d}$ represent hydrogen, and the other(s) represent(s) halogen; cyano; C$_{1-6}$ alkyl which is unsubstituted or substituted with a hydroxyl group; C$_{1-6}$ alkoxy; carbonyl having, as a substituent, hydroxyl, amino, mono- or di-(C$_{1-6}$ alkyl)amino which is substituted with hydroxyl or unsubstituted mono- or di-(C$_{1-6}$ alkyl)amino, or mono- or di-(C$_{1-6}$ alkoxy) amino; or an unsaturated heterocyclic group;
R$^2$ represents phenyl, pyridyl, or thienyl;
R$^3$ represents hydrogen, methyl, ethyl, or cyclopropyl; and
R$^4$ represents hydrogen or hydroxy.

2. The method according to claim 1, wherein A, B, C, and D represent C—R$^{1a}$, C—R$^{1b}$, C—R$^{1c}$, and C—R$^{1d}$, respectively, or one or two of A, B, C, and D represent an N atom;
at least two of R$^{1a}$, R$^{1b}$, R$^{1c}$, and R$^{1d}$ represent hydrogen, and the other(s) individually represent(s) chlorine, fluorine, cyano, methyl, hydroxymethyl, methoxy, ethoxy, carboxyl, carbamoyl, methylaminocarbonyl, ethylaminocarbonyl, hydroxyethylaminocarbonyl, ethoxyaminocarbonyl, or pyrazolyl;
R$^2$ represents phenyl, pyridyl, or thienyl;
R$^3$ represents hydrogen, methyl, ethyl, or cyclopropyl; and
R$^4$ represents hydrogen or hydroxy.

3. A method for potentiating one or more antitumor agents, comprising administering an imidazooxazine compound of any one of the following (a) to (t), or a salt thereof, as an active ingredient, in combination with one or more antitumor agents, to a patient in need of such treatment,
- (a) trans-3-amino-1-cyclopropyl-3-(4-(10-fluoro-3-phenyl-5H-benzo[e]imidazo[1,2-c][1,3]oxazin-2-yl)phenyl)cyclobutanol,
- (b) trans-3-amino-1-cyclopropyl-3-(4-(10-fluoro-3-(pyridin-4-yl)-5H-benzo[e]imidazo[1,2-c][1,3]oxazin-2-yl)phenyl)cyclobutanol,
- (c) trans-3-amino-1-cyclopropyl-3-(4-(3-phenyl-5H-benzo[e]imidazo[1,2-c][1,3]oxazin-2-yl)phenyl)cyclobutanol,
- (d) trans-3-amino-1-cyclopropyl-3-(4-(10-methoxy-3-phenyl-5H-benzo[e]imidazo[1,2-c][1,3]oxazin-2-yl)phenyl)cyclobutanol,
- (e) trans-3-amino-1-cyclopropyl-3-(4-(9-methoxy-3-phenyl-5H-benzo[e]imidazo[1,2-c][1,3]oxazin-2-yl)phenyl)cyclobutanol,
- (f) trans-3-amino-1-cyclopropyl-3-(4-(8-methoxy-3-phenyl-5H-benzo[e]imidazo[1,2-c][1,3]oxazin-2-yl)phenyl)cyclobutanol,
- (g) trans-3-amino-1-cyclopropyl-3-(4-(3-phenyl-5H-imidazo[1,2-c]pyrido[2,3-e][1,3]oxazin-2-yl)phenyl)cyclobutanol,
- (h) trans-3-amino-1-methyl-3-(4-(3-phenyl-5H-imidazo[1,2-c]pyrido[2,3-e][1,3]oxazin-2-yl)phenyl)cyclobutanol,
- (i) trans-3-amino-1-ethyl-3-(4-(3-phenyl-5H-imidazo[1,2-c]pyrido[2,3-e][1,3]oxazin-2-yl)phenyl)cyclobutanol,
- (j) trans-3-amino-1-cyclopropyl-3-(4-(3-phenyl-5H-imidazo[1,2-c]pyrido[3,4-e][1,3]oxazin-2-yl)phenyl)cyclobutanol,
- (k) trans-3-amino-1-methyl-3-(4-(3-phenyl-5H-imidazo[1,2-c]pyrido[3,4-e][1,3]oxazin-2-yl)phenyl)cyclobutanol,
- (l) trans-3-amino-1-cyclopropyl-3-(4-(3-phenyl-5H-imidazo[1,2-c]pyrido[4,3-e][1,3]oxazin-2-yl)phenyl)cyclobutanol,
- (m) trans-3-amino-1-methyl-3-(4-(3-phenyl-5H-imidazo[1,2-c]pyrido[4,3-e][1,3]oxazin-2-yl)phenyl)cyclobutanol,
- (n) trans-3-amino-1-cyclopropyl-3-(4-(3-phenyl-5H-imidazo[1,2-c]pyrido[3,2-e][1,3]oxazin-2-yl)phenyl)cyclobutanol,
- (o) trans-3-amino-1-cyclopropyl-3-(4-(3-phenyl-5H-imidazo[1,2-c]pyrazino[2,3-e][1,3]oxazin-2-yl)phenyl)cyclobutanol,
- (p) trans-3-amino-3-(4-(9-(hydroxymethyl)-3-phenyl-5H-benzo[e]imidazo[1,2-c][1,3]oxazin-2-yl)phenyl)-1-methylcyclobutanol,
- (q) 2-(4-(trans-1-amino-3-hydroxy-3-methylcyclobutyl)phenyl)-3-phenyl-5H-benzo[e]imidazo[1,2-c][1,3]oxazine-9-carbonitrile,
- (r) trans-3-amino-1-methyl-3-(4-(3-phenyl-9-(1H-pyrazol-5-yl)-5H-benzo[e]imidazo[1,2-c][1,3]oxazin-2-yl)phenyl)cyclobutanol,
- (s) 2-(4-(trans-1-amino-3-hydroxy-3-methylcyclobutyl)phenyl)-N-methyl-3-phenyl-5H-benzo[e]imidazo[1,2-c][1,3]oxazine-8-carboxamide, and
- (t) 2-(4-(trans-1-amino-3-hydroxy-3-methylcyclobutyl)phenyl)-N-ethoxy-3-phenyl-5H-benzo[e]imidazo[1,2-c][1,3]oxazine-8-carboxamide.

4. An antitumor composition comprising an imidazooxazine compound or a pharmaceutically acceptable salt thereof in combination with one or more antitumor agents, wherein said imidazooxazine compound is represented by Formula (I), or a pharmaceutically acceptable salt thereof, in an amount effective for potentiating the effect of said one or more antitumor agents,

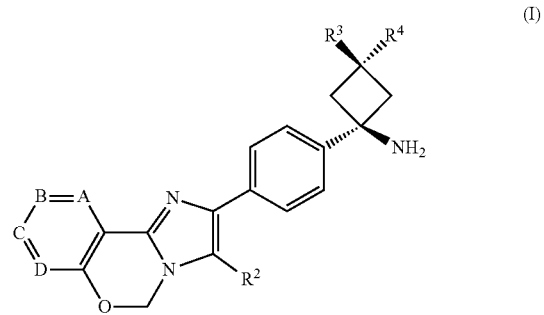

wherein A, B, C, and D represent C—$R^{1a}$, C—$R^{1b}$, C—$R^{1c}$, and C—$R^{1d}$, respectively, or one or two of A, B, C, and D represent an N atom;

at least two of $R^{1a}$, $R^{1b}$, $R^{1c}$, and $R^{1d}$ represent hydrogen, and the other(s) represents halogen; cyano; $C_{1-6}$ alkyl; $C_{1-6}$ alkoxy; carbonyl having, as a substituent, hydroxyl; amino, mono- or di-($C_{1-6}$ alkyl)amino substituted with hydroxyl or unsubstituted mono- or di-($C_{1-6}$ alkyl) amino or mono- or di-($C_{1-6}$ alkoxy)amino; or an unsaturated heterocyclic group;

$R^2$ represents phenyl, pyridyl, or thienyl;
$R^3$ represents hydrogen, methyl, ethyl, or cyclopropyl; and
$R^4$ represents hydrogen or hydroxy.

5. A method for making an antitumor composition, comprising combining an imidazooxazine compound or a pharmaceutically acceptable salt thereof with one or more antitumor agents and a pharmaceutically acceptable carrier, wherein said imidazooxazine compound is represented by Formula (I), or a pharmaceutically acceptable salt thereof, in an amount effective for potentiating the effect of said one or more antitumor agents,

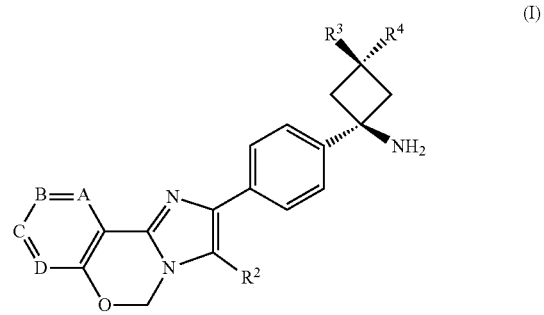

wherein A, B, C, and D represent C—$R^1$, C—$R^{1b}$, C—$R^{1c}$, and C—$R^{1d}$, respectively, or one or two of A, B, C, and D represent an N atom;

at least two of $R^{1a}$, $R^{1b}$, $R^{1c}$, and $R^{1d}$ represent hydrogen, and the other(s) represents halogen; cyano; $C_{1-6}$ alkyl; $C_{1-6}$ alkoxy; carbonyl having, as a substituent, hydroxyl, amino, mono- or di-($C_{1-6}$ alkyl)amino substituted with hydroxyl or unsubstituted mono- or di-($C_{1-6}$ alkyl) amino or mono- or di-($C_{1-6}$ alkoxy)amino; or an unsaturated heterocyclic group;

$R^2$ represents phenyl, pyridyl, or thienyl;

$R^3$ represents hydrogen, methyl, ethyl, or cyclopropyl; and $R^4$ represents hydrogen or hydroxy.

6. The method according to claim 1, wherein the one or more antitumor agents are selected from the group consisting of paclitaxel, carboplatin, lapatinib, irinotecan, doxorubicin, everolimus, bortezomib, erlotinib, trastuzumab (herceptin), metformin, docetaxel, and a combination drug of tegafur, gimeracil, and oteracil potassium.

7. A pharmaceutical composition comprising an imidazooxazine compound or a pharmaceutically acceptable salt thereof, a pharmaceutically acceptable carrier and one or more antitumor agents, wherein said imidazooxazine compound is represented by Formula (I), or a pharmaceutically acceptable salt thereof, in an amount effective for potentiating the effect of said one or more antitumor agents,

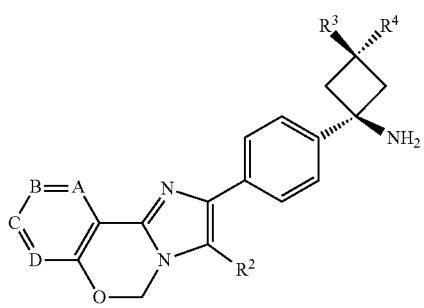

(I)

wherein A, B, C, and D represent C—$R^{1a}$, C—$R^{1b}$, C—$R^{1c}$, and C—$R^{1d}$, respectively, or one or two of A, B, C, and D represent an N atom;

at least two of $R^{1a}$, $R^{1b}$, $R^{1c}$, and $R^{1d}$ represent hydrogen, and the other(s) re resent s halogen; cyano; $C_{1-6}$ alkyl; $C_{1-6}$ alkoxy; carbonyl having, as a substituent, hydroxyl, amino, mono- or di-($C_{1-6}$ alkyl)amino substituted with hydroxyl or unsubstituted mono- or di-($C_{1-6}$ alkyl) amino or mono- or di-($C_{1-6}$ alkoxy)amino; or an unsaturated heterocyclic group;

$R^2$ represents phenyl, pyridyl, or thienyl;

$R^3$ represents hydrogen, methyl, ethyl, or cyclopropyl; and $R^4$ represents hydrogen or hydroxy.

8. A method for treating a malignant tumor in which AKT (serine/threonine-specific kinase) is frequently activated or highly expressed, comprising administering to a patient a combination of a imidazooxazine compound or a pharmaceutically acceptable salt thereof and one or more antitumor agents in an amount effective for treatment of said malignant tumor, wherein said imidazooxazine compound is represented by Formula (I), or a pharmaceutically acceptable salt thereof, in an amount effective for potentiating the effect of said one or more antitumor agents,

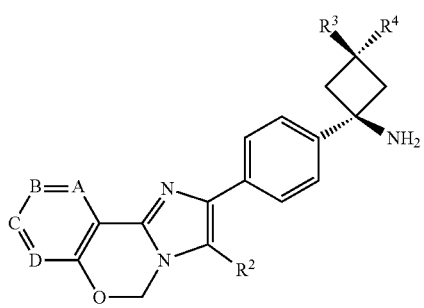

(I)

wherein A, B, C, and D represent C—$R^{1a}$, C—$R^{1b}$, C—$R^{1c}$, and C—$R^{1d}$, respectively, or one or two of A, B, C, and D represent an N atom;

at least two of $R^{1a}$, $R^{1b}$, $R^{1c}$, and $R^{1d}$ represent hydrogen, and the other(s) re resent s halogen; cyano; $C_{1-6}$ alkyl; $C_{1-6}$ alkoxy; carbonyl having, as a substituent, hydroxyl, amino, mono- or di-($C_{1-6}$ alkyl)amino substituted with hydroxyl or unsubstituted mono- or di-($C_{1-6}$ alkyl) amino or mono- or di-($C_{1-6}$ alkoxy)amino; or an unsaturated heterocyclic group;

$R^2$ represents phenyl, pyridyl, or thienyl;

$R^3$ represents hydrogen, methyl, ethyl, or cyclopropyl; and $R^4$ represents hydrogen or hydroxy.

9. A kit for the treatment of malignant tumors, comprising an imidazooxazine compound or a pharmaceutically acceptable salt thereof and one or more antitumor agents wherein said imidazooxazine compound is represented by Formula (I), or a pharmaceutically acceptable salt thereof, in an amount effective for potentiating the effect of said one or more antitumor agents,

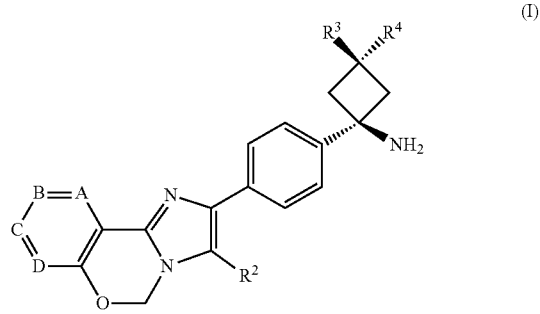

(I)

wherein A, B, C, and D represent C—$R^{1a}$, C—$R^{1b}$, C—$R^{1c}$, and C—$R^{1d}$, respectively, or one or two of A, B, C, and D represent an N atom;

at least two of $R^{1a}$, $R^{1b}$, $R^{1c}$, and $R^{1d}$ represent hydrogen, and the other(s) represent(s) halogen; cyano; $C_{1-6}$ alkyl; $C_{1-6}$ alkoxy; carbonyl having, as a substituent, hydroxyl, amino, mono- or di-($C_{1-6}$ alkyl)amino substituted with hydroxyl or unsubstituted mono- or di-($C_{1-6}$ alkyl) amino or mono- or di-($C_{1-6}$ alkoxy)amino; or an unsaturated heterocyclic group;

$R^2$ represents phenyl, pyridyl, or thienyl;

$R^3$ represents hydrogen, methyl, ethyl, or cyclopropyl; and $R^4$ represents hydrogen or hydroxyl.

10. The antitumor composition according to claim 4, wherein the one or more antitumor agents are selected from the group consisting of paclitaxel, carboplatin, lapatinib, irinotecan, doxorubicin, everolimus, bortezomib, erlotinib, trastuzumab (herceptin), metformin, docetaxel, and a combination drug of tegafur, gimeracil, and oteracil potassium.

11. The method according to claim 1, wherein said $C_{1-6}$ alkyl has hydroxyl group(s) as substituent(s).

12. The method according to claim 8, wherein said malignant tumor in which AKT serine/threonine-specific kinase is frequently activated or highly expressed is a cancer selected from the group consisting of head and neck cancer, esophagus cancer, stomach cancer, colon cancer, rectum cancer, hepatocarcinoma, gallbladder cancer, cholangiocarcinoma, pancreatic cancer, lung cancer, breast cancer, ovarian cancer, cervical cancer, endometrial cancer, renal cancer, bladder cancer, prostate cancer, testicular tumor, osteosarcoma, soft-tissue sarcoma, leukemia, malignant lymphoma, multiple myeloma, skin cancer, and a brain tumor.

* * * * *